United States Patent
Cho et al.

(10) Patent No.: US 11,123,388 B2
(45) Date of Patent: Sep. 21, 2021

(54) COMPOSITION FOR PREVENTING AND TREATING INFLAMMATORY BOWEL DISEASE

(71) Applicant: GENUONE SCIENCES INC., Seoul (KR)

(72) Inventors: Yong-baik Cho, Gyeonggi-do (KR); Seul-ki Kim, Sejong (KR); Sang-Back Kim, Seoul (KR); Jae-hyuck Shin, Seoul (KR); Young-ran Um, Sejong (KR); So-youn Mok, Chungcheongnam-do (KR); Ju-ri Jung, Seoul (KR); Soon-min Lim, Sejong (KR); Chae Shin Seo, Daegu (KR); Hong Koo Cho, Seoul (KR); Bon Am Koo, Seoul (KR); Hyo Jin Jeon, Gyeonggi-do (KR); Han-Seok Choi, Gyeonggi-do (KR); Ye Jin Kim, Incheon (KR)

(73) Assignee: GENUONE SCIENCES INC., Seoul (KR)

( * ) Notice: Subject to any disclaimer, the term of this patent is extended or adjusted under 35 U.S.C. 154(b) by 127 days.

(21) Appl. No.: 15/771,659

(22) PCT Filed: Nov. 4, 2016

(86) PCT No.: PCT/KR2016/012702
§ 371 (c)(1),
(2) Date: Apr. 27, 2018

(87) PCT Pub. No.: WO2017/078486
PCT Pub. Date: May 11, 2017

(65) Prior Publication Data
US 2018/0303888 A1    Oct. 25, 2018

(30) Foreign Application Priority Data

Nov. 6, 2015  (KR) .................. 10-2015-0155745
Sep. 12, 2016 (KR) .................. 10-2016-0117110

(51) Int. Cl.
| | | |
|---|---|---|
| A61K 36/285 | (2006.01) | |
| A61K 36/9068 | (2006.01) | |
| A61K 36/185 | (2006.01) | |
| A23L 33/105 | (2016.01) | |
| A61K 36/28 | (2006.01) | |
| A61P 1/00 | (2006.01) | |
| A61K 9/00 | (2006.01) | |

(52) U.S. Cl.
CPC .......... A61K 36/285 (2013.01); A23L 33/105 (2016.08); A61K 9/0053 (2013.01); A61K 9/0056 (2013.01); A61K 36/185 (2013.01); A61K 36/28 (2013.01); A61K 36/9068 (2013.01); A61P 1/00 (2018.01); *A23V 2002/00* (2013.01); *A61K 2236/331* (2013.01); *A61K 2236/333* (2013.01)

(58) Field of Classification Search
None
See application file for complete search history.

(56) References Cited

U.S. PATENT DOCUMENTS 9,044,502 B2    6/2015  Bian et al.

FOREIGN PATENT DOCUMENTS

| CN | 1435216 A | 8/2003 | |
|---|---|---|---|
| CN | 104095919 A | * 10/2014 | .......... A61K 36/536 |
| CN | 104162124 A | 11/2014 | |
| CN | 104547057 A | * 4/2015 | |
| KR | 2004-0018475 A | 3/2004 | |
| KR | 10-1337389 B1 | 12/2013 | |
| KR | 10-1446396 B1 | 10/2014 | |
| KR | 10-2015-0039958 A | 4/2015 | |
| KR | 10-2015-0119728 A | 10/2015 | |

OTHER PUBLICATIONS

Seo et al., Anti-allergic effects of sesquiterpene lactones from the root of Aucklandia lappa Decne, 2015, Molecular Medicine Reports, 12: 7789-7795.*
Kim et al.; "Effects of Aucklandia lappa in an animal model of Dextran sulfate sodium (DSS)-induced inflammatory bowel disease"; Korean J. Orient. Int. Med. (2013), 34(2), 134-146.
Lowe et al.; "Epidemiology of Crohn's disease in Quebec, Canada", Inflamm Bowel Dis, (2009), 15(3), 429-435.
Toumi et al.; "Beneficial role of the probiotic mixture Ultrabiotique on maintaining the integrity of intestinal mucosal barrier in DSS-induced experimental colitis"; Immunopharmacol Immunotoxicol, (2013) 35(3), 403-409.
Shi et al.; :Inflammatory bowel disease requires the interplay between innate and adaptive immune signals; Cell Res. (2006); 16(1), 70-74.
Mashhadi et al.; "Anti-oxidative and anti-inflammatory effects of ginger in health and physical activity: review of current evidence"; (2013) Int J Prev Med. 4, 36-42.
Shen et al.; "Comparative effects of ginger root (Zingiber officinale Rosc.) on the production of inflammatory mediators in normal and osteoarthrotic sow chondrocytes"; (2005) J Med Food. 8(2), 149-153.

(Continued)

*Primary Examiner* — Terry A McKelvey
*Assistant Examiner* — Catheryne Chen
(74) *Attorney, Agent, or Firm* — Pearne & Gordon LLP

(57) ABSTRACT

Provided is a pharmaceutical composition for preventing or treating inflammatory bowel disease (IBD) comprising a mixed extract of at least two of *Aucklandia lappa* Decne, *Terminalia chebula* Retzius, and *Zingiber officinale* Rosc. as an active ingredient and a method thereof, and more specifically, to a pharmaceutical composition having an inhibitory effect on monocyte adhesion in intestinal epithelial cells, an effect of inhibiting the production of inflammatory cytokines, an effect of ameliorating colitis in an animal model of dextran sodium sulfate (DSS)-induced colitis, and an effect of ameliorating Crohn's disease in an animal model of 2,4,6-trinitrobenzenesulfonic acid (TNBS)-induced Crohn's disease.

13 Claims, 25 Drawing Sheets

(56) References Cited

OTHER PUBLICATIONS

Thomson, et al.; "The use of ginger (Zingiber officinale Rosc.) as a potential anti-inflammatory and antithrombotic agent" Prostaglandins Leukot Essent Fatty Acids. (2002) 67(6), 475-478.

Kim et al.; "Saussurea lappa extract suppresses TPA-induced cell invasion via inhibition of NF-κB-dependent MMP-9 expression in MCF-7 breast cancer cells"; BMC Complement Altern Med. (2014) 14, 170-178.

Choi et al.; "Santamarin, a sesquiterpene lactone isolated from Saussurea lappa, represses LPS-induced inflammatory responses via expression of heme oxygenase-1 in murine macrophage cells. Int Immunopharmacol"; (2012) 13(3), 271-279.

Zhao et al.; "Inhibitory effects of sesquiterpenes from Saussurea lappa on the overproduction of nitric oxide and TNF-alpha release in LPS-activated macrophages"; J Asian Nat Prod Res. (2008) 10(11-12), 1045-1053.

Gokhale et al.; "Preliminary evaluation of anti-inflammatory and anti-arthritic activity of S. lappa, A. speciosa and A. aspera"; Phytomedicine. (2002) 9(5), 433-437.

International Search Report dated Feb. 17, 2017 for corresponding International Application No. PCT/KR2016/012702.

Written Opinion dated Feb. 17, 2017 for corresponding International Application No. PCT/KJR2016/012702.

Naver Blog., "Effects and Side Effects of Aucklandia lappa Decne (Aristolochia contorta, inula helenium, Aucklandia appa Decne", Feb. 17, 2017; Internet URL: http://blog.naver.com/herb_medical/220116377692.

Bag, A. et al., "The development of Terminalia chebula Retz. (Combretaceae) in clinical research" Asian Pacific Journal of Tropical Biomedicine, 2013, vol. 3, No. 3, pp. 244-252.

Kim, Hui Jeong, WOW The Korea Economic Daily TV internet Article, "Food such as Banana, Ginger and plum Used for Treating Bowel Disease, Wisdom of the Ancestors!", Dec. 30, 2014; Internet URL: http://www.wowtv.co.kr/newscenter/news/view.asp?bcode=T30003000&wowcode=W005&artid=A201412300759&compcode=WO.

Chinese Office Action dated Sep. 22, 2020 for corresponding Chinese Application No. 201680078214.8 and English translation.

Jianguo Mu et al., "50 Cases of Ulcerative Colitis Treated with Integrated Traditional Chinese and Western Medicine", Journal of Practical Traditional Chinese Medicine, 22(2), pp. 93-94, Feb. 2016.

Bichen Lui, "Selected Interpretations on Pediatric Classics of Traditional Chinese Medicine", China Medical Science and Technology Press, p. 402, Jun. 2003.

Yi Qian, "Direct Determination on Drug Syndrome in Children", Guangxi Science and Technology Presss, p. 60, Sep. 2015.

Falan Qiu et al., "30 Cases of Senile Chronic Diarrhea Treated with Xiangjiang Powder", China's Naturopathy, 10(5):40, May 2002.

Changfang Yu, "Collection of Chinese Herbal Porridge", China Light Industry Press Ltd., p. 281, Mar. 1991.

Chinese Office Action issued for corresponding Chinese Application No. 201680078214.8 dated May 14, 2021, 14 pages.

* cited by examiner (A) normal (B) DSS-Induced model (C) 5-ADA (D) Aucklandia lappa Dencne
Zinqiber officinale Rosc.

A

B

C

COMPOSITION FOR PREVENTING AND TREATING INFLAMMATORY BOWEL DISEASE

TECHNICAL FIELD

The present invention relates to a use of a mixed extract of *Aucklandia lappa* Decne, *Terminalia chebula* Retzius, and *Zingiber officinale* Rosc., and more specifically, to a composition for preventing, treating, or ameliorating inflammatory bowel disease (IBD) containing a mixed extract of at least two of *Aucklandia lappa* Decne, *Terminalia chebula* Retzius, and *Zingiber officinale* Rosc. as an active ingredient.

BACKGROUND ART

Inflammatory bowel disease (IBD) is an intractable disease that causes chronic inflammation or ulceration in the mucosa of the large intestine and small intestine, and causes diarrhea, melena and repeated recurrence in the long term.

Inflammatory bowel disease is a disease more common in Western people, but has also been increasing rapidly in Korea since the 1980s. The age of onset of inflammatory bowel disease is 15 to 35 years and the disease is reported in all ages, 15% of whom are over 60 years old. Approximately 15% of patients with inflammatory bowel disease have family history in their immediate family.

Inflammatory bowel disease can be caused by environmental, genetic, and immune factors (Kitahora, T. (2012) Familial prevalence of inflammatory bowel disease, Nihon Rinsho, 70 Suppl 1, 44-47; Lowe, A. M., Roy, P. O., M, B. P., Michel, P., Bitton, A., St-Onge, L., & Brassard, P. (2009) Epidemiology of Crohn's disease in Quebec, Canada. Inflamm Bowel Dis, 15(3), 429-435), and the exact etiology of inflammatory bowel disease remains unclear (Toumi, R., Abdelouhab, K., Rafa, H., Soufli, I., Raissi-Kerboua, D., Djeraba, Z., & Touil-Boukoffa, C. (2013). Beneficial role of the probiotic mixture Ultrabiotique on maintaining the integrity of intestinal mucosal barrier in DSS-induced experimental colitis. Immunopharmacol Immunotoxicol, 35(3), 403-409).

The cause of development of inflammatory bowel disease is still unclear, but it is assumed that inflammatory mediators and activation of immune cells are important causes of the disease due to autoimmune diseases, etc. along with environmental or genetic factors.

Inflammatory bowel disease is clinically classified as two diseases, ulcerative colitis and Crohn's disease, which are clinically similar but different from each other in histological findings and endoscopic and immunological aspects. In these inflammatory bowel diseases, the activation of inflammatory mediators and activation of immune cells are known to be important etiological causes.

Continuous or inappropriate activation of the intestinal immune system plays an important role in the pathophysiology of chronic mucosal inflammation, and particularly eventually results in mucosal destruction and ulceration by infiltration of neutrophils, macrophages, lymphocytes, and mast cells.

In the inflammatory response mainly accompanied during the process of development of inflammatory bowel disease, inflammatory response stimulating cytokines such as tumor necrosis factor-α (TNF-α), interleukin-6 (IL-6), and interleukin-8 (IL-8) play major roles.

In particular, TNF-α is highly expressed in the colonic lumen and colonic epithelial cells of patients with ulcerative colitis, and recent studies have shown that TNF-α plays an important role in the pathogenesis of ulcerative colitis. Infliximab, an anti-TNF-α antibody, has been known to be effective not only in the treatment of boils, but also in the treatment of previously untreated Crohn's disease. However, such therapy is expensive and, in some patients, causes side effects such as an infusion response and an infectious complication.

At present, therapeutic agents for inflammatory bowel disease are 5-aminosalicylic acid (5-ASA)-based agents that block the production of prostaglandins (e.g., sulfasalazine, mesalazine, etc.) or steroid-based as immunosuppressants. Immunosuppressants such as azathioprine, 6-mercaptopurine, cyclosporine, etc. have also been used in patients who do not respond to steroid therapy, but there is still no drug to cure inflammatory bowel disease.

Additionally, long-term administration of these drugs can cause side effects, such as leukopenia, skin rash, fever, pancreatitis, hepatitis, hemolytic anemia, and bone marrow suppression due to hypersensitivity as well as nausea, vomiting, indigestion, anorexia, and headache.

Meanwhile, natural extracts and formulations using the same have been used to alleviate and treat various diseases ranging from coughs, colds to parasitic infections and inflammations. Today, more than 60% of anticancer agents used in the market and more than 75% of infectious diseases are of natural origin. This is because natural products are very diverse and provide highly specific physiological activity.

However, no reliable therapies for inflammatory bowel disease have yet been developed. Accordingly, there is a need for the development of effective therapeutic agents for these diseases, and in this regard, natural extracts useful for inflammatory bowel disease are needed.

Under these circumstances, the present inventors have made efforts to develop a composition derived from a mixed extract of natural plants that does not cause side effects and is effective for the treatment of inflammatory bowel disease. As a result, they have discovered that a mixed extract of at least two of *Aucklandia lappa* Decne, *Terminalia chebula* Retzius, and *Zingiber officinale* Rosc. has the excellent effects of inhibiting the production of inflammatory cytokines such as tumor necrosis factor-α (TNF-α) and interleukin-6 (IL-6), inhibiting monocyte infiltration, and effects of recovery of the colon length and weight loss, ameliorating the conditions in diarrhea and melena in an animal model of dextran sodium sulfate (DSS)-induced colitis and in an animal model of 2,4,6-trinitrobenzenesulfonic acid (TNBS)-induced Crohn's disease, and additionally confirmed the effective dose through effects according to the administration dose of a mixed extract of at least two of *Aucklandia lappa* Decne, *Terminalia chebula* Retzius, and *Zingiber officinale* Rosc., thereby completing the present invention.

PRIOR ART DOCUMENTS

Patent Documents

1. Korea Registered Patent No. 10-1337389
2. Korea Registered Patent No. 10-1446396
3. Korea Patent Application Publication No. 10-2004-0018475
4. U.S. Pat. No. 9,044,502 B2

Non-Patent Documents

1. KIM, So-Yeon, PARK, Jae-Woo, RYU, Bong-Ha (2013), Effects of *Aucklandia lappa* in an animal model of Dex- 1. tran sulfate sodium (DSS)-induced inflammatory bowel disease. Korean J. Orient. Int. Med. 34(2), 134-146
2. Kitahora, T. (2012) Familial prevalence of inflammatory bowel disease, Nihon Rinsho, 70, 44-47
3. Lowe, A. M., Roy, P. O., M, B. P., Michel, P., Bitton, A., St-Onge, L., & Brassard, P. (2009) Epidemiology of Crohn's disease in Quebec, Canada. Inflamm Bowel Dis, 15(3), 429-435
4. Toumi, R., Abdelouhab, K., Rafa, H., Soufli, I., Raissi-Kerboua, D., Djeraba, Z., & Touil-Boukoffa, C. (2013) Beneficial role of the probiotic mixture Ultrabiotique on maintaining the integrity of intestinal mucosal barrier in DSS-induced experimental colitis. Immunopharmacol Immunotoxicol, 35(3), 403-409
5. Moreau J. (2014) Crohn's disease and ulcerative colitis. Rev Infirm. 199, 16-18
6. Shi D, Das J, Das G. (2006) Inflammatory bowel disease requires the interplay between innate and adaptive immune signals. Cell Res. 16(1), 70-74
7. Mashhadi N S, Ghiasvand R, Askari G, Hariri M, Darvishi L, Mofid M R. (2013) Anti-oxidative and anti-inflammatory effects of ginger in health and physical activity: review of current evidence. Int J Prev Med. 4, 36-42
8. Shen C L, Hong K J, Kim S W. (2005) Comparative effects of ginger root (*Zingiber officinale* Rosc.) on the production of inflammatory mediators in normal and osteoarthrotic sow chondrocytes. J Med Food. 8(2), 149-153
9. Thomson M, Al-Qattan K K, Al-Sawan S M, Alnaqeeb M A, Khan I, Ali M. (2002) The use of ginger (*Zingiber officinale* Rosc.) as a potential anti-inflammatory and antithrombotic agent. Prostaglandins Leukot Essent Fatty Acids. 67(6), 475-478
10. Kim H R, Kim J M, Kim M S, Hwang J K, Park Y J, Yang S H, Kim H J, Ryu D G, Lee D S, Oh H, Kim Y C, Rhee Y J, Moon B S, Yun J M, Kwon K B, Lee Y R. (2014) *Saussurea lappa* extract suppresses TPA-induced cell invasion via inhibition of NF-κB-dependent MMP-9 expression in MCF-7 breast cancer cells. BMC Complement Altern Med. 14, 170-178
11. Choi H G, Lee D S, Li B, Choi Y H, Lee S H, Kim Y C (2012) Santamarin, a sesquiterpene lactone isolated from *Saussurea lappa*, represses LPS-induced inflammatory responses via expression of heme oxygenase-1 in murine macrophage cells. Int Immunopharmacol. 13(3), 271-279
12. Zhao F, Xu H, He E Q, Jiang Y T, Liu K. (2008) Inhibitory effects of sesquiterpenes from *Saussurea lappa* on the overproduction of nitric oxide and TNF-alpha release in LPS-activated macrophages. J Asian Nat Prod Res. 10(11-12), 1045-1053
13. Gokhale A B, Damre A S, Kulkami K R, Saraf M N. (2002) Preliminary evaluation of anti-inflammatory and anti-arthritic activity of *S. lappa, A. speciosa* and *A. aspera*. Phytomedicine. 9(5), 433-437

DISCLOSURE

Technical Problem

A main object of the present invention is to provide various uses of a mixed extract containing at least two of *Aucklandia lappa* Decne, *Terminalia chebula* Retzius, and *Zingiber officinale* Rosc.

An object of the present invention is to provide a pharmaceutical composition for preventing or treating inflammatory bowel disease containing a mixed extract of at least two of *Aucklandia lappa* Decne, *Terminalia chebula* Retzius, and *Zingiber officinale* Rosc. as an active ingredient, and a preparation method thereof.

Another object of the present invention is to provide a health functional food for preventing or ameliorating inflammatory bowel disease containing a mixed extract of at least two of *Aucklandia lappa* Decne, *Terminalia chebula* Retzius, and *Zingiber officinale* Rosc. as an active ingredient.

Additionally, still another object of the present invention is to provide an effective dose of a mixed extract containing at least two of *Aucklandia lappa* Decne, *Terminalia chebula* Retzius, and *Zingiber officinale* Rosc., for the purpose of a pharmaceutical composition or heath functional food for preventing, treating, or ameliorating inflammatory bowel disease containing the mixed extract as an active ingredient.

Technical Solution

—To solve the above problems,
in an embodiment, the present invention provides a pharmaceutical composition for preventing or treating inflammatory bowel disease containing a mixed extract of at least two of *Aucklandia lappa* Decne, *Terminalia chebula* Retzius, and *Zingiber officinale* Rosc. as an active ingredient.

In particular, for example, when the mixed extract is a mixture of *Aucklandia lappa* Decne and *Terminalia chebula* Retzius, the mixed extract may contain *Aucklandia lappa* Decne and *Terminalia chebula* Retzius in a 1:1 weight ratio; when the mixed extract is a mixture of *Aucklandia lappa* Decne and *Zingiber officinale* Rosc., the mixed extract may contain *Aucklandia lappa* Decne and *Zingiber officinale* Rosc. in a 1:1 weight ratio; when the mixed extract is a mixture of *Zingiber officinale* Rosc. and *Terminalia chebula* Retzius, the mixed extract may contain *Zingiber officinale* Rosc. and *Terminalia chebula* Retzius in a 1:1 weight ratio; and when the mixed extract is a mixture of *Aucklandia lappa* Decne, *Terminalia chebula* Retzius, and *Zingiber officinale* Rosc., the mixed extract may contain *Aucklandia lappa* Decne, *Terminalia chebula* Retzius, and *Zingiber officinale* Rosc. in a 2:2:1 weight ratio.

The mixed extract may be a crude extract, a polar solvent soluble extract, or a non-polar solvent soluble extract of *Aucklandia lappa* Decne, *Terminalia chebula* Retzius, and *Zingiber officinale* Rosc. The crude extract may be an extract which is solubilized in a solvent selected from water including distilled water, methanol, ethanol, butanol, or a mixed solvent thereof, and the polar solvent soluble extract may be an extract which is solubilized in a solvent selected from water, ethanol, butanol or a mixed solvent thereof, and the non-polar solvent soluble extract may be an extract solubilized in hexane, chloroform, dichloromethane or ethyl acetate.

In a preferred embodiment, the mixed extracts of the present invention may be extracted using water, C1-C4 lower alcohol, or a mixture thereof as a solvent, and in particular, a hot-water extract or ethanol extract may be used, and most preferably 50% to 100% ethanol extract may be used.

The extract of the present invention may be a mixed extract obtained by mixing the *Aucklandia lappa* Decne and the *Terminalia chebula* Retzius or the *Zingiber officinale* Rosc. followed by extracting the mixture, or the mixed extract may be an extract in which an *Aucklandia lappa* Decne extract extracted from *Aucklandia lappa* Decne, a *Terminalia chebula* Retzius extract extracted from *Terminalia chebula* Retzius or a *Zingiber officinale* Rosc. extract extracted from *Zingiber officinale* Rosc. are mixed.

Additionally, the extract of the present invention may be a mixed extract obtained by mixing the *Aucklandia lappa* Decne and the *Terminalia chebula* Retzius, and the *Zingiber officinale* Rosc. followed by extracting the mixture, or the mixed extract may be an extract in which an *Aucklandia lappa* Decne extract extracted from *Aucklandia lappa* Decne, a *Terminalia chebula* Retzius extract extracted from *Terminalia chebula* Retzius, and a *Zingiber officinale* Rosc. extract extracted from *Zingiber officinale* Rosc. are mixed.

Meanwhile, the mixture may further contain an extract of as *Paeonia lactiflora* Pall, RHEI RHIZOMA, Euryales Semen, Magnoliae Cortex, Cinnamomi Cortex Spissus, Cimicifugae Rhizoma, Bupleuri Radix, Amomi Fructus, Atractylodis Rhizoma Alba, *Coix lacryma-jobi* L. var. *mayuen* Stapf seed, etc. in addition to *Aucklandia lappa* Decne, *Terminalia chebula* Retzius, and *Zingiber officinale* Rosc.

In particular, a mixed extract containing at least two of *Aucklandia lappa* Decne, *Terminalia chebula* Retzius, and *Zingiber officinale* Rosc. can be extracted at 20° C. to 120° C. for 1 to 15 hours, for example, at 60° C. to 120° C. for 1 to 6 hours.

The mixed extract can prevent and treat inflammatory bowel disease by inhibiting the production of at least one of inflammatory mediators (i.e., IL-6 and TNF-α).

The inflammatory bowel disease may include Crohn's disease, ulcerative colitis, intestinal Behcet's disease, intestinal tuberculosis and enteritis, diarrhea, etc. Ulcerative colitis is a chronic disease that causes inflammation in the large intestine and forms ulcers, which causes hemorrhagic diarrhea, severe pain in the abdomen, and seizure accompanied by fever. The exact cause of ulcerative colitis is not known, but ulcerative colitis is presumed to be caused by autoimmune diseases, etc. along with environmental or genetic factors. Crohn's disease, which is also known as regional enteritis, granulomatous ileitis or ileocolitis, is chronic inflammation of the wall that occurs in any part of the digestive tract.

In the present invention, the mixed extract may have at least one effect among the effects of recovery of the colon length and weight loss, and ameliorating the conditions in diarrhea and melanain in an animal model of dextran sodium sulfate (DSS)-induced colitis and in an animal model of 2,4,6-trinitrobenzenesulfonic acid (TNBS)-induced Crohn's disease.

Additionally, in another specific embodiment, the present invention provides a health functional food for preventing or ameliorating inflammatory bowel disease containing a mixed extract of at least two of *Aucklandia lappa* Decne, *Terminalia chebula* Retzius, and *Zingiber officinale* Rosc., and a use thereof.

The health functional food may be prepared in the form of, for example, powders, granules, tablets, capsules, syrups or drinks, etc.

In still another specific embodiment, the present invention provides an effective dose for a pharmaceutical composition or health functional food for preventing, treating, or ameliorating inflammatory bowel disease containing a mixed extract of at least two of *Aucklandia lappa* Decne, *Terminalia chebula* Retzius, and *Zingiber officinale* Rosc. as an active ingredient.

An effective amount of the mixed extract having an excellent anti-inflammatory effect may be at 0.1 wt % to 50 wt % of the extract relative to the total weight of the composition. Preferably, the mixed extract may be at a concentration of 50 mg/kg to 400 mg/kg, and most preferably, 200 mg/kg to 400 mg/kg.

As described above, the present invention includes all of the various uses which utilizes an effective amount exhibiting the anti-inflammatory function of the mixed extract of at least two of *Aucklandia lappa* Decne, *Terminalia chebula* Retzius, and *Zingiber officinale* Rosc., and more specifically, the effects of inhibiting the production of inflammatory cytokines (i.e., tumor necrosis factor-α (TNF-α) and interleukin-6 (IL-6)), inhibiting the infiltration of monocytes, recovery of the colon length and weight loss, ameliorating the conditions in diarrhea and melanain in an animal model of dextran sodium sulfate (DSS)-induced colitis and in an animal model of 2,4,6-trinitrobenzenesulfonic acid (TNBS)-induced Crohn's disease, and an excellent anti-inflammatory effect.

Advantageous Effects of the Invention

The composition containing a mixed extract of *Aucklandia lappa* Decne, *Terminalia chebula* Retzius, and *Zingiber officinale* Rosc. according to the present invention has an excellent anti-inflammatory effect and an effect of ameliorating colitis, while having almost no toxicity, and is thus expected to be effectively used as an active ingredient as a composition for a pharmaceutical drug, processed food, functional food, food additive, functional drink, or drink additive, etc. for prevention and treatment of an inflammatory disease, particularly, inflammatory bowel disease.

BEST MODE FOR CARRYING OUT THE INVENTION

Figure 1:
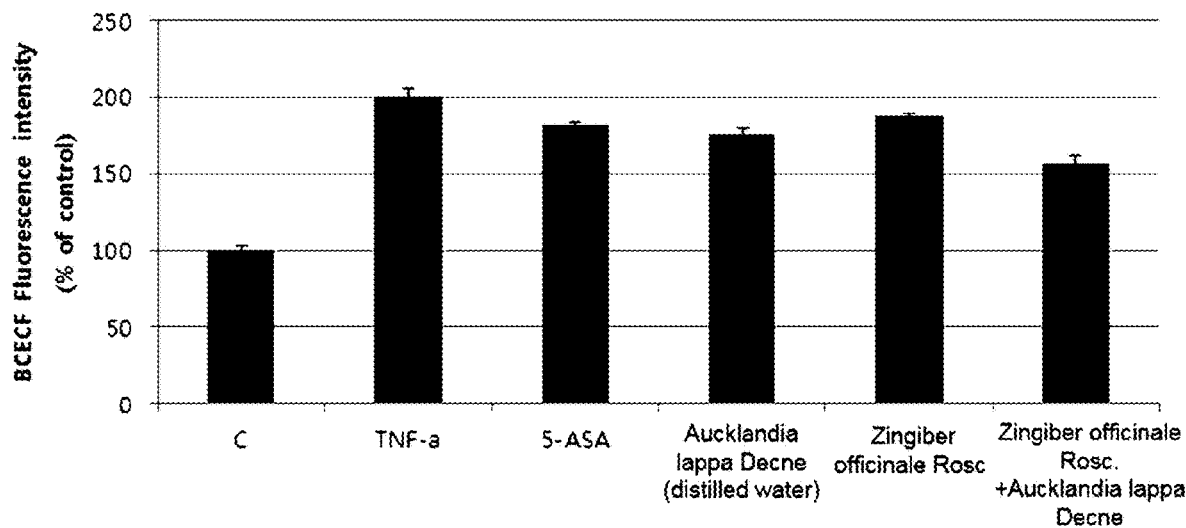
FIG. 1 shows a graph illustrating the inhibitory effect of a mixed extract containing *Aucklandia lappa* Decne and *Zingiber officinale* Rosc. on monocyte adhesion in intestinal epithelial cells.

The terms used in the present invention are defined as follows.

The term "extract" refers to a preparation which is prepared by squeezing a herbal medicine with an appropriate leachate and evaporating the leachate to concentrate, and the extract may be an extract obtained by extraction treatment, a diluted or concentrated solution of the extract, a dried product obtained by drying the extract, and a crude product or purified product thereof, but the extract is not limited thereto. The extract may be prepared using common extraction methods, isolation and purification methods known in the art. The extraction method may include boiled-water extraction, hot-water extraction, cold-immersion extraction, reflux cooling extraction, or ultrasonic extraction, but the extraction method is not limited thereto. As used herein, fractions are also included in the extract.

The term "crude extract" refers to an extract solubilized in a solvent selected from water including distilled water, C1-C4 lower alcohol such as methanol, ethanol, butanol, etc., or a mixed solvent thereof, preferably a mixed solvent of water and ethanol, and more preferably a 50% to 100% ethanol.

The term "polar solvent soluble extract" includes an extract soluble in a solvent selected from water, methanol, ethanol, butanol, or a mixed solvent thereof, and preferably water or ethanol.

The term "non-polar solvent soluble extract" includes an extract soluble in a solvent selected from hexane, chloroform, dichloromethane, or ethyl acetate, preferably hexane, dichloromethane, or ethyl acetate, and more preferably, hexane or ethyl acetate.

The term "carrier" is defined as a compound that facilitates the addition of a compound into a cell or tissue. For example, dimethylsulfoxide (DMSO) is a commonly used carrier that facilitates the introduction of many organic compounds into cells or tissues of an organism.

The term "diluent" is defined as a compound which not only stabilizes the biologically active form of a subject compound but also a compound that is diluted in water to dissolve the compound. Salt dissolved in a buffer solution is used as a diluent in the art. A commonly used buffer solution is phosphate buffered saline because it mimics the salt in a state of the human solution. A buffered diluent rarely modifies the biological activity of a compound because buffer salts can control the pH of a solution at low concentrations.

The term "subject" or "patient" refers to any single individual requiring treatment, including humans, cows, dogs, guinea pigs, rabbits, chickens, insects, etc., and additionally, any subject participating in a clinical trial study that does not show any clinical findings of disease, or a subject participating in epidemiological studies or a subject used as the control group.

The term "tissue or cell sample" refers to an aggregate of similar cells obtained from the tissue of a subject or patient. The source of supply of the tissue or cell sample may be a solid tissue from fresh, frozen and/or preserved organ or tissue sample or biopsy or aspirate; blood or any blood component; and a cell at any time-point of pregnancy or development of the subject. Tissue samples may also be primary or cultured cells or cell lines.

The term "administration" refers to providing a composition to a subject in any suitable manner.

The term "effective amount" refers to an appropriate amount that provides an advantageous or desired clinical or biochemical result. The effective amount may be administered once or more times. For the purpose of the present invention, the effective amount is an amount suitable to temporarily alleviate, ameliorate, stabilize, reverse, slow down, or delay the progression of a disease state. If the beneficial animal is capable of enduring the administration of a composition or is suitable for the administration of the composition to the animal, the composition is considered as "pharmaceutically or physiologically acceptable". In a case where the amount administered is of physiological significance, it can be said that the preparation was administered in "a therapeutically an effective amount". In a case where the preparation has resulted in a physiologically detectable change in the recipient, the preparation is of physiological significance.

The term "treating", unless specified otherwise, refers to reversing, alleviating, inhibiting, or preventing the disease or disorder to which the term applies, or one or more symptoms of the disease or disorder. As used herein, the term "treatment" refers to the act of treating when defined the term "treating" is defined as above.

The term "health functional food" refers to a food having improved functionality of a general food by adding an extract of one specific embodiment of the present invention to the general food. Functionality can be divided into physical and physiological functionalities. When the extract of the present invention is added to a general food, the physical properties and physiological functions of the general food will be improved, and the present invention collectively defines the food of such enhanced function as "health functional food" in a comprehensive manner.

The term "about" refers to an amount, level, value, number, frequency, percent, dimension, size, quantity, weight, or length that varies by the extent of 30%, 25%, 20%, 25%, 10%, 9%, 8%, 7%, 6%, 5%, 4%, 3%, 2%, or 1%, with respect to reference amount, level, value, number, frequency, percent, dimension, size, quantity, weight, or length.

All of the technical terms used herein, unless defined otherwise, is used in the sense that it is generally understood by those of ordinary skill in the field to which the present invention pertains. Additionally, although preferred methods or samples are described in the present specification, similar or equivalent ones are also included in the scope of the present invention. The contents of all of the publications cited herein are incorporated in the present invention by reference.

Hereinafter, the present invention will be described in detail.

The present invention relates to the use of a mixed extract containing at least two of *Aucklandia lappa* Decne, *Terminalia chebula* Retzius, and *Zingiber officinale* Rosc., and to the specific physiological activities and functions that the mixed extract containing at least two of *Aucklandia lappa* Decne, *Terminalia chebula* Retzius, and *Zingiber officinale* Rosc. possess.

[Effective Material]

*Aucklandia lappa* Decne is a perennial herb that belongs to the family of Asteraceae/Compositae, whose flowering period is from July to September and fertility period is from August to October. It grows in relatively high mountains and its origin is India, and in China it grows in Yunnan, Gwangseong, and Sacheon provinces. *Aucklandia lappa* Decne is also called in various names, such as *Aquilaria agallocha*, *Aristolochia contorta*, rhizome of *Aucklandia lappa* Decne, South *Aucklandia lappa* Decne, Broad *Aucklandia lappa* Decne, *Saussurea lappa* CLARKE, *Vladimiria denticulata*, *Dolomiaea souliei*, etc.

Since *Aucklandia lappa* Decne has a warm drug property, it shows good therapeutic effects for abdominal pain caused by the cold abdomen, symptoms of a false sense of satiety, vomiting, diarrhea, etc., is effective in dysentery, and is also known that it has effects of increasing the function of the large intestine, facilitating excretion of the urine, and stopping the pain.

*Zingiber officinale* Rosc. is a dried ginger root, which is a perennial herb of tropical Asia origin belonging to the family of Zingiberaceae and the genera of Zingiberaceae. The herbs of the family of Zingiberaceae mostly found in the tropical regions and there are 1,400 species of about 47 genera in the world. As for the herbs of the genera of Zingiberaceae, about 50 species are distributed in East Asia, India, and Malaysia, and *Zingiber mioga* and ginger of the genera of Zingiberaceae are grown in Korea. Wild ginger of the genera of *Hedychium coronarium* J Konig is grown, and *Alpinia japonica* (Thunb.) Miq. of the genera of *Alpinia* is naturally grown in the forests of southern islands of Korea. *Zingiber officinale* Rosc. is also called dry ginger, homogeneous ginger, white ginger, and live ginger.

*Zingiber officinale* Rosc. is spicy, temperate, and has no toxicity, acts on the lungs, stomach, and spleen meridian, and also acts on the heart, liver, and gall bladder meridians. It has the effects of emitting bad energy, releasing cold energy, stopping vomiting, and flowing the phlegm, and can treat cold, wind-cold pathogen, vomiting, retention of phlegm, asthma, cough, feeling of stomach swelling, and diarrhea. Additionally, *Zingiber officinale* Rosc. is known to helps vitalize energy, promote blood circulation, remove cold energy and wind energy, detoxify and perform anti-inflammatory action, remove bad teeth odor, stop pain, and relieve eczema due to dampness.

*Terminalia chebula* Retzius is a mature fruit of a *Terminalia chebula* Retzius tree. The *Terminalia chebula* Retzius trees are tropical tall trees native to India, Myanmar, Malaysia, Sichuan province of China., etc. and in its juice, yellow pigment which is a myrovalan is extracted and is also used as furniture wood. *Terminalia chebula* Retzius is also called in various names, such as *Terminalia chebula* RETZ, *Terminalia chebula* (Gaertner) *RETZ*, etc.

*Terminalia chebula* Retzius has a slight peculiar odor, has drug properties of bitterness, a bit of sourness, astringency, and warmness. It has the effects of lowering the level of energy, removing long-lasting phlegm and coughing, and is effective for dyspnea, lasting diarrhea, dysentery, leukorrhea, rectal prolapse, helping digestion, improving appetite, and relaxing the fetus in the uterus. In addition, reportedly, *Terminalia chebula Retzius* has pharmacological actions of contraction, antidiarrheic, and inhibition of bacteria such as *Pseudomonas aeruginosa*.

In an aspect, the present invention utilizes extracts or fractions in which at least two of *Aucklandia lappa* Decne, *Terminalia chebula* Retzius, and *Zingiber officinale* Rosc. are combined.

The extracts or fractions can be extracted or fractionated from various regions of *Aucklandia lappa Decne, Terminalia chebula* Retzius, *Zingiber officinale* Rosc.

The fractions of *Aucklandia lappa* Decne, *Terminalia chebula* Retzius, *Zingiber officinale* Rosc. may be obtained as a fraction of each solvent through the process of fractionation of each extract of *Aucklandia lappa* Decne, *Terminalia chebula* Retzius, *Zingiber officinale* Rosc. in an organic solvent from a polar solvent to a non-polar solvent. Suitable solvents for the fractionation may be water, ethanol, methanol, hexane, chloroform, dichloromethane, ethyl acetate, butanol, or a mixed solvent thereof.

The extracts of *Aucklandia lappa* Decne, *Terminalia chebula* Retzius, *Zingiber officinale* Rosc. of the present invention may be prepared by methods known in the art, modified methods thereof, or by the methods of the present invention.

For example, the extracts may be extracted by cold-immersion extraction, hot-water extraction, ultrasonic extraction, reflux cooling extraction, or heat extraction. According to an embodiment of the present invention, the extract of the present invention may be extracted by hot-water extraction or reflux cooling extraction, and may be repeatedly extracted 1 to 10 times, 1 to 8 times, or 1 to 6 times.

Additionally, the extracts or fractions of *Aucklandia lappa* Decne, *Terminalia chebula* Retzius, *Zingiber officinale* Rosc. may be prepared in the form of powders by an additional process such as distillation under reduced pressure, freeze-drying, or spray drying, etc. Additionally, the extracts or fractions may also be obtained as further purified fractions using various chromatographies such as silica gel column chromatography, thin layer chromatography, high performance liquid chromatography, etc.

Accordingly, in the present invention, the extracts of *Aucklandia lappa* Decne, *Terminalia chebula* Retzius, *Zingiber officinale* Rosc. relates to a concept that includes all of the extracts, fractions, purified products, dilutions thereof, concentrates thereof, or dried products thereof obtained at each step of extraction, fractionation, or purification.

In an embodiment, the extract may be prepared by the following method:

i) a step of performing an extraction by independently or simultaneously adding an extraction solvent to at least two materials of *Aucklandia lappa* Decne, *Terminalia chebula* Retzius, and *Zingiber officinale* Rosc.;

ii) a step of performing a filtration of the extracts of step i); and iii) a step of drying the filtrates of step ii).

In step i), as the extraction solvent, any solvent acceptable in the art may be used, and water or an organic solvent may be used. The extraction solvent is preferably water, alcohol, or a mixture thereof. As the alcohol, C1-C4 lower alcohols are preferably used, and ethanol is more preferably used as the lower alcohol.

For example, various kinds of solvents such as distilled water, alcohols having 1 to 4 carbon atoms including methanol, ethanol, propanol, isopropanol, butanol, etc., acetone, ether, benzene, chloroform, ethyl acetate, methylene chloride, hexane, cyclohexane, etc. may be used alone or in combination, but the solvent is not limited thereto.

The extraction solvent may be used at a concentration of 50% to 100%, 50% to 95%, 50% to 90%, 50% to 85%, 50% to 80%, 50% to 75%, 50% to 70%, 50% to 65%, or 50% to 60%, and preferably, 50% to 60%.

As the extraction method, it is preferable to use shaking extraction, Soxhlet extraction, or reflux extraction, but the extraction method is not limited thereto. The extraction is preferably performed by adding 1 to 10 volumes of the extraction solvent based on the amount of *Aucklandia lappa* Decne and *Terminalia chebula Retzius, Aucklandia lappa* Decne and *Zingiber officinale* Rosc., or *Zingiber officinale* Rosc. and *Terminalia chebula* Retzius. The extraction is preferably performed at a temperature of 20° C. to 120° C., but the temperature is not limited thereto. The extraction may be performed, without limitation, for 1 to 20 hours, preferably 1 to 15 hours, and more preferably 1 to 6 hours.

In the above method, the drying method of step iii) may include drying under reduced pressure, vacuum drying, boiling drying, spray drying, or freeze drying.

In a specific embodiment, in a case where a mixed extract containing at least two of *Aucklandia lappa* Decne, *Terminalia chebula* Retzius, and *Zingiber officinale* Rosc. (e.g., a mixed extract of *Aucklandia lappa* Decne and *Terminalia chebula* Retzius, a mixed extract of *Aucklandia lappa* Decne and *Zingiber officinale* Rosc., and a mixed extract of *Zingiber officinale* Rosc. and *Terminalia chebula* Retzius), preferably, *Aucklandia lappa* Decne and *Terminalia chebula* Retzius, *Aucklandia lappa* Decne and *Zingiber officinale* Rosc, and *Zingiber officinale* Rosc. and *Terminalia chebula* Retzius are mixed in a weight ratio of 1 to 3:1 to 3, more preferably, *Aucklandia lappa* Decne:*Terminalia chebula* Retzius, *Aucklandia lappa* Decne:*Zingiber officinale* Rosc., or *Zingiber officinale* Rosc.:*Terminalia chebula* Retzius are mixed in a weight ratio of 1:1, and a solvent selected from water including distilled water, C1-C4 lower alcohol such as methanol, ethanol, butanol, etc., or a mixed solvent thereof, preferably a mixed solvent of water and ethanol (e.g., 50% to 100% ethanol) is added in an amount of about 1 to about 30 volumes (w/v %), preferably 5 to 15 volumes (w/v %) relative to the mixed weight, and extracted at a temperature of about 20° C. to about 120° C., preferably 60° C. to about 100° C., for 1 to 15 hours, preferably 1 to 6 hours, by cold-immersion extraction, hot-water extraction, ultrasonic extraction, reflux extraction, or heat extraction, etc., preferably reflux extraction, and then filtered and dried, and thereby a combined crude extract containing *Aucklandia lappa* Decne:*Terminalia chebula* Retzius, *Aucklandia lappa*

Decne:*Zingiber officinale* Rosc., or *Zingiber officinale* Rosc.:*Terminalia chebula* Retzius.

In another specific embodiment, in a case where a mixed extract containing all of *Aucklandia lappa* Decne, *Terminalia chebula* Retzius, and *Zingiber officinale* Rosc. is prepared, each of the mixtures of *Aucklandia lappa* Decne:*Terminalia chebula* Retzius:*Zingiber officinale* Rosc. may be mixed in a weight ratio of 1 to 3:1 to 3:1 to 3. In a specific embodiment, *Aucklandia lappa* Decne:*Terminalia chebula* Retzius:*Zingiber officinale* Rosc. may be mixed in a ratio of 1:1:1, 2:2:1, 2:1:1, 1:2:1, or 1:1:2. In a preferred embodiment, *Aucklandia lappa* Decne:*Terminalia chebula* Retzius:*Zingiber officinale* Rosc. may be mixed in a ratio of 2:2:1 or 2:1:1, and more preferably, *Aucklandia lappa* Decne:*Terminalia chebula* Retzius:*Zingiber officinale* Rosc. may be mixed in a ratio of 2:2:1.

In another embodiment, with respect to the mixed extract containing at least two of *Aucklandia lappa* Decne, *Terminalia chebula* Retzius, and *Zingiber officinale* Rosc. of the present invention, a mixed crude extract containing at least two extracts of *Aucklandia lappa* Decne, *Terminalia chebula* Retzius, and *Zingiber officinale* Rosc. of the present invention can be obtained by adding a solvent selected from water including distilled water, C1-C4 lower alcohol such as methanol, ethanol, butanol, etc., or a mixed solvent thereof, preferably a mixed solvent of water and ethanol (e.g., 50% to 100% ethanol) in an amount of about 1 to about 30 volumes (w/v %), preferably 5 to 15 volumes (w/v %) relative to each weight thereof; extracting at a temperature of about 20° C. to about 120° C., preferably 60° C. to about 100° C., for 1 to 15 hours, preferably 1 to 6 hours, by cold-immersion extraction, hot-water extraction, ultrasonic extraction, reflux extraction, or heat extraction, etc., preferably reflux extraction, respectively; filtering; and then mixing each extract in a volume ratio explained above, followed by drying.

In an embodiment of the present invention, a mixed extract containing *Aucklandia lappa* Decne and *Terminalia chebula* Retzius extracts or *Aucklandia lappa* Decne and *Zingiber officinale* Rosc. extracts; and a mixed extract containing *Aucklandia lappa* Decne, *Terminalia chebula* Retzius, and *Zingiber officinale* Rosc. extracts were obtained.

Optionally, the extracts of the present invention may further contain an extract of at least material selected from the group consisting of *Paeonia lactiflora* Pall, Bupleuri Radix, Cimicifugae Rhizoma, RHEI RHIZOMA, Euryales Semen, Magnoliae Cortex, Cinnamomi Cortex Spissus, Amomi Fructus, Atractylodis Rhizoma Alba, *Coix lacryma-jobi* L. var. *ma-yuen* Stapf seed, etc.

Accordingly, the present invention includes a method for preparing a mixed extract containing at least two of *Aucklandia lappa* Decne, *Terminalia chebula* Retzius, and *Zingiber officinale* Rosc.

The preparation methods described above are merely exemplary methods and these methods can be appropriately modified and used by various methods based on the technologies in the art. For example, non-exemplified extraction methods according to the present invention can be successfully performed by modifications apparent to those skilled in the art.

It will be obvious to those of ordinary skill in the art can confirm the specific reaction conditions for the preparation of the mixed extracts containing *Aucklandia lappa* Decne and *Terminalia chebula* Retzius, *Aucklandia lappa* Decne and *Zingiber officinale* Rosc., or *Zingiber officinale* Rosc. and *Terminalia chebula* Retzius, or the mixed extract containing *Aucklandia lappa* Decne, *Terminalia chebula* Retzius, and *Zingiber officinale* Rosc. According to the present invention through the explanations described later, and thus the detailed explanations thereof will be omitted herein.

[Inflammatory Bowel Disease]

The present invention relates to the prevention, treatment, and/or improvement of functions of mixed extracts containing at least two of *Aucklandia lappa* Decne, *Terminalia chebula* Retzius, and *Zingiber officinale* Rosc., which were prepared above.

In the present invention, inflammatory disease refers to any condition that is characterized by local or systemic bioprotective responses due to external physiochemical stimuli or infections of external infectious sources such as bacteria, fungi, viruses, various allergens, or other causes. These responses may be due to activation of various inflammatory mediators and immune cells, accompanied by a series of complex physiological responses, such as activation of related enzymes (e.g., iNOS, COX-2, etc.) secretion of mediators (e.g., secretion of NO, TNF-$\alpha$, IL-6, IL-1$\beta$, and PGE2), infiltration of body fluids, cell migration, tissue destruction, etc.), and be manifested externally by symptoms such as erythema, pain, swelling, fever, deterioration or loss of certain functions of the body, etc.

Since these inflammatory diseases may have acute, chronic, ulcerative, allergic, or necrotic properties, it does not matter whether acute, chronic, ulcerative, allergic or necrotic as long as any disease is included in such inflammatory diseases.

Additionally in the present invention, the inflammatory diseases may include inflammatory bowel disease.

The term "inflammatory bowl disease (IBD)" refers to a chronic inflammatory disease of unknown etiology that invades the digestive tract, which is an intractable disease that causes diarrhea, melena, and recurrence for a long period of time.

Inflammatory bowel disease may largely be divided into, commonly called, ulcerative colitis (UC) and Crohn's disease (CD). Although the clinical features of the two diseases are different, both diseases have a chronic progress, and are referred to as inflammatory bowel disease because the causes and pathophysiologies of these diseases are not known.

Inflammatory bowel disease is conventionally divided into ulcerative colitis and Crohn's disease, but intestinal Behcet's disease, an intestinal disease relatively common in Korea, may belong to inflammatory bowel disease. Behcet's disease, in addition to oral ulcers, genital ulcers, and ocular symptoms, may invade many organs such as skin, blood vessels, gastrointestinal tract, central nervous system, heart, and lungs, etc.

The terms "Crohn's disease (CD)" and "ulcerative colitis (UC)" are chronic inflammatory bowel diseases whose etiologies are unknown.

Unlike ulcerative colitis, Crohn's disease can affect any part of the intestine. The most prominent aspect of Crohn's disease is the enlargement of granular reddish purple edemas on the intestinal wall. As inflammation develops, these granulomas often lose their local boundaries and integrate with surrounding tissues. The main clinical features of Crohn's disease are diarrhea and bowel obstruction. As is the case with ulcerative colitis, the course of Crohn's disease may be persistent, recurrent, mild, or severe. However, unlike ulcerative colitis, Crohn's disease cannot be cured by ablating the intestinal segment that causes the disease. Most patients with Crohn's disease require surgerical treatment at some point, but subsequent medical treatment is common because subsequent recurrence is common.

The "ulcerative colitis (UC)" invades the colon. The progress of the disease may be continuous, recurrent, mild, or severe. The earliest lesion is inflammatory infiltration with abscess formation at the base of the crypts of Lieberkuhn. The adhesion of these dilated and ruptured crypts tends to cause ulceration by separating the underlying mucosa from the blood supply. Symptoms of this disease include frequent and loose feces consisting mainly of blood, pus, and mucus, along with spasm, pain in the lower abdomen, rectal bleeding, and sparse stool particles. Acute, severe, or chronic and continuous ulcerative colitis may require the entire colonic resection. The clinical features of UC may be highly variable, and the onset of the disease may be insidious or sudden, and may accompany diarrhea, tenesmus, and recurrent rectal bleeding. Due to the fulminant onset of the disease in the entire colon, toxic megacolon, which is life-threatening, may occur. Signs other than the intestine may include arthritis, pyoderma gangrenosum, uveitis, and nodular erythema.

Accordingly, the inflammatory bowel disease, which is intended to be treated, prevented, and ameliorated using a mixed extract containing at least two of *Aucklandia lappa* Decne, *Terminalia chebula* Retzius, and *Zingiber officinale* Rosc., includes, for example, at least one selected from the group consisting of Crohn's disease, ulcerative colitis, intestinal Behcet's disease, intestinal tuberculosis, and diarrhea.

Through embodiments of the present invention, it was observed that the mixed extract containing at least two of *Aucklandia lappa* Decne, *Terminalia chebula* Retzius, and *Zingiber officinale* Rosc. has an effect of inhibiting monocyte adhesion in intestinal epithelial cells; an effect of inhibiting production of LPS-induced inflammatory cytokines (i.e., TNF-α and IL-6); and an effect of improving recovery of the colon length and weight loss, and conditions of diarrhea and melena in an animal model of dextran sodium sulfate (DSS)-induced colitis and in an animal model of trinitrobenzene sulfonic acid (TNBS)-induced Crohn's disease, and thereby confirming the specific functions as follows.

(i) The mixed extract containing at least two of *Aucklandia lappa* Decne, *Terminalia chebula* Retzius, and *Zingiber officinale* Rosc. of the present invention has an effect of inhibiting monocyte infiltration on intestinal mucose.

It is known that infiltration of many monocytes is observed in the intestinal mucosa of patients with inflammatory bowel disease (IBD). Monocytes, also called mononuclear leukocytes, are a type of phagocytes present in the blood that can differentiate into macrophages or dendritic cells and play a role in controlling the homeostasis and immune and inflammatory responses of tissues. The infiltration of these monocytes eventually causes mucosal destruction and ulceration, resulting in dysfunction and damage of the intestinal mucosa. Accordingly, the inhibition of monocyte infiltration into the intestinal mucosa may be an important factor in preventing or treating inflammation and ulcers in the mucosa.

In an embodiment of the present invention, it was confirmed that the mixed extract containing at least two of *Aucklandia lappa* Decne, *Terminalia chebula* Retzius, and *Zingiber officinale* Rosc. has an excellent effect of inhibiting monocyte adhesion in intestinal epithelial cells.

(ii) The mixed extract containing at least two of *Aucklandia lappa* Decne, *Terminalia chebula* Retzius, and *Zingiber officinale* Rosc. of the present invention has an effect of inhibiting the production of inflammatory cytokines.

It is thought that monocytes and lymphocytes are involved in mucosal damage in the lesions of inflammatory bowel disease (IBD) patients, and TNF-α, IL-6, etc., which are inflammatory cytokines produced from these cells, cause intestinal inflammation or ulceration and thereby cause intestinal dysfunction and damage.

TNF-α is a factor which induces neutrophils to the site of inflammation at the beginning of an inflammatory response, causing and aggravating acute inflammatory responses, whereas IL-6 is a representative inflammatory cytokine which is synthesized and secreted by various factors and plays an important role in the development and progression of acute or chronic inflammatory diseases.

In an embodiment of the present invention, it was confirmed that the mixed extract containing at least two of *Aucklandia lappa* Decne, *Terminalia chebula* Retzius, and *Zingiber officinale* Rosc. has an effect of inhibiting the production of LPS-induced inflammatory cytokines (i.e., TNF-α and IL-6) of macrophages.

(iii) The mixed extract containing at least two of *Aucklandia lappa* Decne, *Terminalia chebula* Retzius, and *Zingiber officinale* Rosc. of the present invention has an effect of improvement in an animal model of DSS inflammatory bowel disease and in an animal model of TNBS Crohn's disease.

In an embodiment of the present invention, an animal model of DSS-induced inflammatory bowel disease and an animal model of TNBS-induced Crohn's disease were prepared, and the effects of the mixed extract containing at least two of *Aucklandia lappa* Decne, *Terminalia chebula* Retzius, and *Zingiber officinale* Rosc. on the improvement of colitis and Crohn's disease were observed using these animals, and as a result, it was confirmed that the colon length of the animal models was recovered and also excellent effect of improving the levels of loss of body weight, diarrhea, and melena represented through disease activity index (DAI). Additionally, as a result of confirming the state of oxidative stress in immune diseases, the treatment with the mixed extract treatment showed an inhibition of MPO activity, thus confirming an excellent effect of suppressing oxidative stress.

(iv) in an embodiment, when the mixed extract containing at least two of *Aucklandia lappa* Decne, *Terminalia chebula* Retzius, and *Zingiber officinale* Rosc. is an extract obtained by 50% ethanol extraction or in a particular mixing ratio of at least two materials, the mixed extract showed an excellent effect of cell proliferation and inhibiting the production of nitric oxide (NO).

Extraction solvents may be important for extracting components useful for treating inflammatory bowel disease in natural materials, and selection of an appropriate extraction solvent may be a significant technical characteristic because there may be differences in the amount of active ingredients extracted and the extraction of unwanted components, depending on the extraction solvent.

In an embodiment of the present invention, as a result of confirming cytotoxicity and the effect of inhibiting NO production of a mixed extract extracted by varying the concentrations of ethanol in the extraction solvent, it was confirmed that 50% ethanol extract showed no cytotoxicity and promoted cell proliferation, and 76% ethanol extract inhibited NO production.

Additionally, in the case of a mixed extract, there may be a variety of differences in active ingredients obtained and effects obtained according to the blending ratio of each natural material or herbal material. Therefore, the discovery of the blending ratios that can maximize the effect while minimizing toxicity may also be a technically significant characteristic.

In an embodiment of the present invention, it was confirmed that the mixed extract according to the blending ratio (w/w) of *Aucklandia lappa* Decne and *Terminalia chebula* Retzius, or *Zingiber officinale* Rosc. has the effect of inhibiting the production of NO, which is a major cause of cytotoxicity and inflammation, and the effect of inhibiting the infiltration of monocytes, which causes ulceration, and confirmed that the mixed extract shows an excellent effect when *Aucklandia lappa* Decne:*Terminalia chebula Retzius*, or *Zingiber officinale* Rosc. are mixed at about 1:1 ratio.

In another embodiment of the present invention, it was confirmed that a mixed extract according to the blending ratio (w/w) of *Aucklandia lappa* Decne, *Terminalia chebula* Retzius, and *Zingiber officinale* Rosc. has the effect of inhibiting the infiltration of monocytes which cause ulceration, the effect of inhibiting the production of inflammatory cytokines, and the effect of ameliorating colitis in an animal model of DSS inflammatory bowel disease and in an animal model of TNBS Crohn's disease, and it was confirmed that the mixed extract shows an excellent effect when *Aucklandia lappa* Decne:*Terminalia chebula Retzius*:*Zingiber officinale* Rosc. are mixed at about 2:2:1 ratio.

(v) in an embodiment of the present invention, the effect of the mixed extract of at least two of *Aucklandia lappa* Decne and *Terminalia chebula* Retzius, or *Zingiber officinale* Rosc. on the improvement of colitis in an animal model of DSS inflammatory bowel disease and in an animal model of TNBS Crohn's disease, according to an effective administration dose was examined.

As a result of confirming the effects of the mixed extract on the administration dose, both the animal model of DSS inflammatory bowel disease and the animal model of TNBS Crohn's disease showed the recovery of the colon length, disease activity index (DAI), and the colon weight per colon length along with the increase of the administration dose, and the best effect of ameliorating colitis was observed when the mixed extract was administered at a concentration of 400 mg/kg.

As such, the present invention includes all of the various uses of the mixed extract containing at least two of *Aucklandia lappa* Decne, *Terminalia chebula* Retzius, and *Zingiber officinale* Rosc for utilizing the functions of prevention, treatment, and/or amelioration of inflammatory bowel disease.

[Pharmaceutical Composition]

In a specific embodiment, the present invention relates to a pharmaceutical composition for preventing or treating inflammatory bowel disease containing a mixed extract of at least two of *Aucklandia lappa* Decne, *Terminalia chebula* Retzius, and *Zingiber officinale* Rosc as an active ingredient.

The effects of preventing and treating inflammatory bowel disease defined in the present invention are characterized in that the effects act through the inhibition of the infiltration of monocytes in the intestinal mucosa, inhibition of the production of inflammatory cytokines (i.e., TNF-α and IL-6), recovery of colon length, weight loss due to colitis, diarrhea and melena reduction.

Additionally, the present invention provides a method for treating and preventing inflammatory diseases including administering the pharmaceutical composition to a subject with inflammatory bowel disease.

The pharmaceutical composition for preventing and treating inflammatory diseases containing the mixed extracts of the present invention is preferably contained in an amount of 0.1 wt % to 50 wt % relative to the total weight of the composition. More preferably, the mixed extract is used at a concentration of 50 mg/kg to 400 mg/kg, and most preferably 200 mg/kg to 400 mg/kg.

The pharmaceutical composition containing a mixed extract of the present invention may further contain appropriate carriers, excipients, and diluents conventionally used in the preparation of pharmaceutical compositions.

Additionally, the composition containing the mixed extract may be formulated or used in combination with a medicament such as steroidal drugs, antihistamines, antiinflammatory agents, and antibiotics, etc. which have already been used.

The pharmaceutical composition containing the mixed extract may each be formulated in the form of an oral preparation such as powders, granules, tablets, capsules, suspensions, emulsions, syrups, aerosols, etc.; external preparations; suppositories; and sterilized injection solutions, according to a conventional method. In the present invention, the pharmaceutical composition can be preferably formulated into a formulation for oral administration.

As the carrier, excipient, and diluent which can be contained in the composition containing the extract of the present invention may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil.

In the case of formulation, a diluent or excipient such as a filler, an extender, a binder, a humectant, a disintegrant, a surfactant, etc. is usually used.

Solid formulations for oral administration may include tablets, pills, powders, granules, capsules, etc., and such a solid preparation may be prepared by mixing at least one excipient (e.g., starch, calcium carbonate, sucrose or lactose, gelatin, etc.) in the above compound. Additionally, in addition to a simple excipient, lubricants such as magnesium stearate and talc are also used. Liquid preparations for oral administration may include suspensions, solutions for internal use, emulsions, syrups, etc. In addition to water and liquid paraffin which are commonly used a diluent, various excipients such as humectants, sweeteners, flavoring agents, preservatives, etc. may be included.

Formulations for parenteral administration may include sterile aqueous solutions, non-aqueous solutions, suspensions, emulsions, freeze-dried preparations, and suppositories. Examples of the non-aqueous solutions and suspending agents may include propylene glycol, polyethylene glycol, vegetable oil such as olive oil, injectable ester such as ethyl oleate, etc. As the base of suppositories, Witepsol, macrogol, Tween 61, cacao butter, laurinium, glycerogelatin, etc. may be used.

The composition of the present invention may be administered orally or parenterally, and the composition is preferably administered orally, but the administration method is not particularly limited thereto.

The amount of the composition of the present invention to be used may vary depending on the age, sex, and body weight of the patient, but may be in the range of 0.0001 mg/kg to 400 mg/kg. The administration dose may also be increased or decreased depending on the administration route, severity of disease, sex, weight, age, etc. The composition may be administered once a day, or divided into several doses. Accordingly, the administration dose shall not limit the scope of the present invention in any manner.

In an embodiment of the present invention, the effect according to an effective administration dose of the mixed extract containing at least two of *Aucklandia lappa* Decne, *Terminalia chebula* Retzius, and *Zingiber officinale* Rosc. in ameliorating colitis in an animal model of DSS inflammatory bowel disease and in an animal model of TNBS Crohn's disease was confirmed. As a result, it was confirmed that both the animal model of DSS inflammatory bowel disease and the animal model of TNBS Crohn's disease showed the recovery of the colon length, disease activity index (DAI), and the colon weight per colon length to normal levels along with the increase of the administration dose, and the best effect of ameliorating colitis was observed when the mixed extract was administered at a concentration of 400 mg/kg.

The pharmaceutical composition may be administered to mammals such as rats, mice, domestic animals, humans, etc. by various routes. All of administration methods may be expected, for example, intravenous, intraperitoneal, intramuscular, intraarterial, oral, intracardiac, intramedullary, intrathecal, transdermal, intestinal, subcutaneous, sublingual, or topical administration, but the administration methods are not limited.

The pharmaceutical dosage forms of the composition of the present invention may also be used in the form of a pharmaceutically acceptable salt, and it may also be used alone or in combination with other pharmaceutically active compounds as well as in suitable aggregates. Additionally, the pharmaceutical composition of the present invention may be used alone or in combination with methods which use surgery, radiation therapy, hormone therapy, chemotherapy, or biological response modifiers, for the prevention or treatment of inflammatory bowel disease or related complications.

[Health Functional Food]

Meanwhile, in another specific embodiment, the present invention relates to a health functional food for preventing or ameliorating inflammatory bowel disease containing a mixed extract containing at least two of *Aucklandia lappa* Decne, *Terminalia chebula* Retzius, and *Zingiber officinale* Rosc., as an active ingredient.

Functionality may be divided into physical and physiological functionalities, and when the mixed extracts of the present invention containing at least two of *Aucklandia lappa* Decne, *Terminalia chebula* Retzius, and *Zingiber officinale* Rosc. is added to general foods, the physical properties and physiological functionality of general foods will be improved. For example, a health functional food for preventing or ameliorating Crohn's disease, ulcerative colitis, intestinal Behcet's disease, intestinal tuberculosis and enteritis, diarrhea, etc., containing mixed extracts of *Aucklandia lappa* Decne and *Terminalia chebula* Retzius, *Aucklandia lappa* Decne and *Zingiber officinale* Rosc., or *Zingiber officinale* Rosc. and *Terminalia chebula* Retzius can be prepared. In addition, functional foods, etc. can be prepared using the same.

That is, a compound or pharmaceutically acceptable salt thereof containing the mixed extract of at least two of *Aucklandia lappa* Decne, *Terminalia chebula* Retzius, and *Zingiber officinale* Rosc. may be used as a food ingredient or as an additive and adjuvant in the preparation of various functional foods and health functional foods.

In the present invention, the kind of the food is not particularly limited. Examples of the foods in which the mixed extract of at least two of *Aucklandia lappa* Decne, *Terminalia chebula* Retzius, and *Zingiber officinale* Rosc. can be added may include various foods, powders, granules, tablets, capsules, syrups, beverages, gums, chocolates, candies, snacks, teas, vitamin complexes, etc., and may include all of the health functional foods in the conventional sense.

The health beverage composition of the present invention does not have any particular limitations on liquid ingredients other than containing the mixed extract as an essential ingredient in the indicated ratios and may contain various flavoring agents or natural carbohydrates, etc. as an additional ingredient such as conventional beverages. Examples of the natural carbohydrates are monosaccharides, for example, disaccharides such as glucose, fructose, etc., and polysaccharides such as maltose, sucrose, etc., for example, conventional sugars such as dextrin, cyclodextrin, etc., and sugar alcohols such as xylitol, sorbitol, erythritol, etc. As a flavoring agent other than those described above, natural flavors (thaumatin, *stevia* extracts (e.g., rebaudioside A, glycyrrhizin, etc.) and synthetic flavors (saccharin, aspartame, etc.) can be advantageously used. The ratio of the natural carbohydrate is generally about 1 g to 20 g, preferably about 5 g to 12 g per 100 mL of the composition of the present invention.

In addition to the above, the composition of the present invention may contain various nutrients, vitamins, minerals (electrolytes), flavoring agents such as synthetic flavoring agents and natural flavoring agents, coloring agents and thickening agents (cheese, chocolate, etc.), pectic acid and its salts, alginic acid and its salts, organic acids, protective colloidal thickening agents, pH adjusting agents, stabilizers, preservatives, glycerin, alcohols, carbonating agents used in carbonated beverages, etc. In addition, the compositions of the present invention may contain flesh for the production of natural fruit juices, fruit juice drinks, and vegetable drinks. These components may be used independently or in combination. The ratio of such additives is not so critical, but the ratio is generally selected in the range of about 0 to about 20 parts by weight per 100 parts by weight of the composition of the present invention.

Additionally, since the mixed extracts of the present invention is of herbal drug components containing at least two of *Aucklandia lappa* Decne, *Terminalia chebula* Retzius, and *Zingiber officinale* Rosc., the mixed extract can be safely used even for long-term use for the treatment, improvement, and prevention of diseases.

As described above, the present invention includes all of the various uses which utilizes an effective amount of the mixed extract of at least two of *Aucklandia lappa* Decne, *Terminalia chebula* Retzius, and *Zingiber officinale* Rosc. exhibiting the effect of inhibiting the adhesion ability of monocytes to the intestinal epithelial cells, inhibiting the production of LPS-induced inflammatory cytokines (i.e., TNF-α and IL-6), recovery of colon length, ameliorating the conditions of weight loss, diarrhea, and melena in an animal model of dextran sodium sulfate (DSS)-induced colitis and in an animal model of 2,4,6-trinitrobenzenesulfonic acid (TNBS)-induced Crohn's disease, and an excellent anti-inflammatory effect.

MODES FOR CARRYING OUT THE INVENTION

Hereinafter, the present invention will be described in more detail with reference to Examples. It should be obvious to those skilled in the art that these embodiments are for illustrative purposes only and that the scope of the present invention is not construed as being limited by these examples.

Experimental Materials
1. Materials and Sample Extraction

At least two of *Aucklandia lappa* Decne (5 g), *Zingiber officinale* Rosc. (5 g) and *Terminalia chebula* Retzius (5 g) were mixed, respectively, and 50% aqueous ethanol solution (100 mL), which was 10 volumes of the sample weight, was added thereto, and subjected to reflux extraction at 95° C. for 2 hours, and the obtained extract was filtered, freeze-dried, and stored in a refrigerator in a powder state, and used as samples for the experiment. A mixed extract of *Aucklandia lappa* Decne and *Zingiber officinale* Rosc., a mixed extract of *Aucklandia lappa* Decne and *Terminalia chebula* Retzius, a mixed extract of *Zingiber officinale* Rosc. and *Terminalia chebula* Retzius, and a mixed extract of *Aucklandia lappa* Decne, *Zingiber officinale* Rosc. and *Terminalia chebula* Retzius were prepared to perform the experiment.

2. Reagents and Instruments (1) Reagents for Measurement of Inhibitory Effect on Monocyte Adhesion in Intestinal Epithelial Cells and Instruments Human intestinal epithelial cell line HT-29 cells (American Type Culture Collections, Rockville, Mass., USA), human monocyte cell line U937 cells (ATCC, Rockville, Mass., USA), bovine fetal serum (FBS), penicillin/streptomycin, 2',7'-bis(2-carboxyethyl)-5(6)-carboxyfluorescein acetoxymethyl ester (BCECF/AM), 5-aminosalicylic acid (5-ASA), and a microplate reader (TECAN, Gr, Austria) for measurement were used.

(2) Reagents for Measurement of Anti-Inflammation and Instruments

Macrophages (American Type Culture Collections, Rockville, Mass., USA), 5-aminosalicylic acid (5-ASA), dexamethasone, TNF-α ELISA kit (R&D Systems, USA), IL-6 ELISA kit (R&D Systems, USA), and a microplate reader (TECAN, Gr, Austria) for measurement were used.

(3) Reagents for Preparation of DSS Animal Model

C57BL/6 female mice (17 g to 19 g, 6-week old, DBL Co., Ltd. (Eumseong, Korea)), 5-aminosalicylic acid (5-ASA), Carboxymethyl Cellulose (CMC), and Dextran sodium sulfate (DSS) were used.

(4) Reagents for Preparation of TNBS Animal Model

ICR female mice (17 g to 19 g, 6-week old, DBL Co., Ltd. (Eumseong, Korea)), 5-aminosalicylic acid (5-ASA), and 2,4,6-trinitro-benzene sulfonic acid (TNBS) were used.

Experimental Method
1. Cell Viability Test (Cytotoxicity Test)

Cells were plated in a certain number according to the purpose of the test. After 24 hours, the medium was replaced with a medium not containing FBS, cultured for 24 hours, and the cells were treated with prepared extracts to be tested. Ater 24 hour treatment with the materials, the medium was removed and the cells were treated with 3-(4,5-dimethylthiazol-2-yl)-2,5-diphenyl tetrazolium bromide (MTT) reagent (5 mg/mL) in an amount of 40 μL/well, and further cultured for 4 hours. After 4 hours, the medium was removed, and dimethylsulfoxide (DMSO, Amresco, 0231-500ML) was added 1 mL each, shook for 10 minutes, and collected 200 μL from the 96-well, and the absorbance was measured at 540 nm. With respect to the level of cytotoxicity, the solvent in which the materials were dissolved was expressed as a percentage based on the absorbance intensity of the control group.

2. Effect of Inhibition of NO Production

Human intestinal epithelial cell line HT-29 cells (American Type Culture Collections, Rockville, Mass., USA) were cultured in Dulbecco's Modified Eagle's Medium (DMEM) along with 10% Fatal bovine serum (FBS), 1% Antibiotic-Antimycotic (GIBCO, Cat No. 15240-062) in 100 mm/60.1 cm$^2$ culture dish at 37° C., 5% $CO_2$ conditions. When the HT-29 cells grew to a confluency of 80% or higher, the cells were dispensed into a 6-well plate at a concentration of $10^5$ cells/well, cultured to a confluency of 80% or higher, and the medium was removed and replaced with a fresh medium containing an extract prepared to an appropriate concentration, and further cultured for 48 hours. The supernatant of cell was collected and used as a sample for the test. The test analysis was performed using the Total NO/Nitrite/Nitrate ELISA kit (R&D systems, Cat. #KGE001) according to the manufacturer's manual. Briefly, the test was performed in the following sequence: the cell culture which was grown after treatment with the sample was dispensed into a 96-well plate in an amount of 50 μL/well, treated with Griess Reagent, reacted at room temperature for 10 minutes, and the absorbance was measured at 540 nm.

3. Effect of Inhibiting Monocyte Adhesion Ability in Intestinal Epithelial Cells Human intestinal epithelial cell line HT-29 cells (American Type Culture Collections, Rockville, Mass., USA) and human monocyte cell line U937 cells (ATCC, Rockville, Mass., USA) were cultured in RPMI 1640 containing fetal bovine serum (FBS) and 1% penicillin/streptomycin, and the cell line was maintained under the environment of 95% air and 5% $CO_2$ at 37° C.

The monocytes-intestinal epithelial cells adhesion was measured using U937 cells, which were labeled with 2',7'-bis(2-carboxyethyl)-5(6)-carboxyfluorescein acetoxymethyl ester (BCECF/AM, 10 μg/mL), at 37° C. for 30 minutes. The HT-29 cells ($2 \times 10^6$ cells/well), which were cultured in a 48-well plate for 24 hours, were simultaneously treated with a extract (100 μg/mL) while treating with TNF-α (100 ng/mL), and cultured for 24 hours.

In particular, 20 mM 5-aminosalicylic acid (5-ASA) was used as the positive control. Then, HT-29 cells were co-cultured along with U937 cells ($5 \times 10^5$ cells/well), which were labeled with BCECF/AM at 37° C. for 30 minutes. Unattached U937 cells were removed and washed twice with PBS. The HT-29 cells to which U937 cells were attached were dissolved using 0.1% Triton X-100 which was dissolved in 0.1 mol/L Tris. The fluorescence of these lysates was measured using the luminance at 485 nm and 520 nm using a microplate reader (TECAN, Gr, Austria).

4. Effect of Inhibiting TNF-α Production

The macrophages (American Type Culture Collections, Rockville, Mass., USA) cultured in a 24-well plate were pretreated with LPS (1 μg/mL) for 1 hour, treated with a extract (100 μg/mL), 20 mM 5-ASA (100 μg/mL) and 20 μM dexamethasone, and cultured for 24 hours, and the supernatant of cell was used for the experiment. First, capture antibody of TNF-α was added into a 96-well ELISA plate and allowed to react overnight. The plate was washed 6 times with 1×PBS (PBS-T) containing 0.05% Tween-20, and blocked with 1× assay diluent solution containing 2% BSA at room temperature for 1 hour. The plate was washed 6 times with 1×PBS-T and the supernatant or TNF-α standard protein was added thereto and allowed to react at room temperature for 2 hours. The plate was again was washed 6 times with 1×PBS-T, detection antibody was added thereto, and allowed to react at room temperature for 2 hours. The plate was again was washed 6 times with 1×PBS-T, avidin-HRP solution was added thereto, and allowed to react at room temperature for 30 minutes. The plate was again was washed 6 times with 1×PBS-T, a TMB substrate solution was added thereto and allowed to react at room temperature for final 30 minutes, and a reaction stopping solution (1 M H$_3$PO$_4$) was added thereto to stop the reaction. With respect to the levels of reactions of the plate, the absorbance was measured at 450 nm using a microplate reader (TECAN, Gr, Austria).

5. Effect of Inhibiting IL-6 Production

The macrophages (American Type Culture Collections, Rockville, Mass., USA) cultured in a 24-well plate were pretreated with LPS (1 μg/mL) for 1 hour, treated with a extract (50 μg/mL), 20 mM 5-ASA (50 μg/mL) and 20 μM dexamethasone, and cultured for 24 hours, and the supernatant was used for the experiment. First, capture antibody of IL-6 was added into a 96-well ELISA plate and allowed to react overnight. The plate was washed 6 times with 1×PBS (PBS-T) containing 0.05% Tween-20, and blocked with 1× assay diluent solution containing 2% BSA at room temperature for 1 hour.

The plate was washed 6 times with 1×PBS-T and the supernatant or IL-6 standard protein was added thereto and allowed to react at room temperature for 2 hours.

The plate was again was washed 6 times with 1×PBS-T, detection antibody was added thereto, and allowed to react at room temperature for 2 hours. The plate was again was washed 6 times with 1×PBS-T, avidin-HRP solution was added thereto, and allowed to react at room temperature for 30 minutes. The plate was again was washed 6 times with 1×PBS-T, a TMB substrate solution was added thereto and allowed to react at room temperature for final 30 minutes, and a reaction stopping solution (1 M H$_3$PO$_4$) was added thereto to stop the reaction. With respect to the levels of reactions of the plate, the absorbance was measured at 450 nm using a microplate reader (TECAN, Gr, Austria).

6. Effect of Inhibiting Oxidative Stress Through Measurement of Myeloperoxidase (MPO) Activity 200 μL of lysis buffer was added to 100 mg of colon tissue collected at the time of autopsy and homogenized and the supernatant obtained by centrifugation at 10,000 rpm for 20 minutes was used. First, capture antibody of MPO was added into a 96-well ELISA plate and allowed to react overnight. The plate was washed 6 times with 1×PBS (PBS-T) containing 0.05% Tween-20, and blocked with 1× assay diluent solution containing 2% BSA at room temperature for 1 hour. The plate was washed 6 times with 1×PBS-T and cell culture or MPO standard protein was added thereto and allowed to react at room temperature for 2 hours. The plate was again was washed 6 times with 1×PBS-T, detection antibody was added thereto, and allowed to react at room temperature for 2 hours. The plate was again was washed 6 times with 1×PBS-T, streptavidin-HRP solution was added thereto, and allowed to react at room temperature for 30 minutes. The plate was again was washed 6 times with 1×PBS-T, a TMB substrate solution was added thereto and allowed to react at room temperature for final 30 minutes, and a reaction stopping solution (1 M H$_3$PO$_4$) was added thereto to stop the reaction. With respect to the levels of reactions of the plate, the absorbance was measured at 450 nm using a microplate reader (TECAN, Gr, Austria).

7. Effect of Ameliorating Colitis in DSS Animal Model

To construct an experimental model of inflammatory bowel disease, 6-week old C57BL/6 female mice (17 g to 19 g) were purchased from DBL Co., Ltd. (Eumseong, Korea), and the mice were given ad libitum access to solid feeds and water and allowed to adapt to a controlled environment with constant humidity (50%), constant temperature (22° C.), and 12-hour light-dark cycle for 1 week. After 1 week of adaptation, the mice were divided into a normal control group, a colitis-induced group, a control drug-treated group (5-ASA 200 mg/kg), and an extract-treated group. The control drug (5-ASA) and extracts were dissolved in 0.5% carboxymethyl cellulose (CMC), and then orally administered once daily for 7 days along with 3% dextran sodium sulfate (DSS), and the normal control group and the colitis-induced group were orally administered with 0.5% CMC. The colitis-induced group, the control drug-treated group, and the extract-treated group were given ad libitum access to 3% DSS for 1 week, and the normal control group was given ad libitum access to water. Then, the mice were sacrificed on the 8th day, and each of their colons was excised from the cecum to the region immediately before the anus, and the length and external appearance of the excised colon were examined to determine the degree of weight loss, diarrhea, and melena, and the results were scored according to the criteria.

8. Effect of Ameliorating Crohn's Disease in TNBS Animal Model

To construct an experimental model of inflammatory bowel disease, 7-week old ICR female mice (25 g to 27 g) were purchased from DBL Co., Ltd. (Eumseong, Korea), and the mice were given ad libitum access to solid feeds and water and allowed to adapt to a controlled environment with constant humidity (50±10%), constant temperature (22±2° C.), and 12-hour light-dark cycle for 1 week. After 1 week of adaptation, the animals were divided into a normal control group, a colitis-induced group, a control drug-treated group (5-ASA 200 mg/kg), and an extract-treated group (200 mg/kg). The mice were fasted for 24 hours before injection of TNBS. The mice in the colitis-induced group, the control drug-treated group, and the extract-treated group were weakly anesthetized with ether, and TNBS (0.5 mg) dissolved in 50% ethanol was injected into the anus at a depth of 2 cm to 3 cm using a PE sonde. After the injection, the head was turned downward for about 1 minute, and the tail was raised so that the injected solution did not flow out through the anus, so that the drug was absorbed into the intestines as much as possible. The control drug (5-ASA) and extracts were dissolved in 0.5% carboxymethyl cellulose (CMC), and orally administered once daily for 5 days. The normal control group and the colitis-induced group were orally administered with 0.5% CMC. After 5 days of oral administration, mice were fasted until the next day and sacrificed. Each of their colons was was excised from the cecum to the region immediately before the anus, and the length and external appearance of the excised colon were examined to determine the degree of weight loss, constipation, and intestinal edema, and the results were scored according to the criteria.

Example 1: Confirmation of Effects on Mixed Extracts of *Aucklandia lappa* Decne and *Zingiber officinale* Rosc 1-1: Effect of Inhibiting Infiltration of Monocytes The effect of the mixed extract of the present invention containing *Aucklandia lappa* Decne and *Zingiber officinale* Rosc. on inhibiting the infiltration of monocytes were confirmed.

As a result, fluorescent-labeled U937 cell adhesion to the HT-29 intestinal epithelial cells was significantly increased by TNF-α stimulus, and it was inhibited by 18.93% by the control drug (5-ASA). In the case of a single extract of *Aucklandia lappa* Decne (distilled water) and *Zingiber officinale* Rosc., the inhibitory effect was shown to be 25.21% and 12.36%, respectively. However, in the case of the mixed extract of the present invention, the inhibitory rate was 44.15% thus confirming that the mixed extracts of the present invention has an effect being equal to or higher compared to that of the control drug (Table 1, FIG. 1). Additionally, the mixed extract of the present invention showed a higher effect compared to those of a single extract of *Zingiber officinale* Rosc. and a single extract of *Aucklandia lappa* Decne (distilled water). Through these results it was confirmed that the extract inhibited monocyte infiltration more effectively than the control drug.

TABLE 1

| Category | Concentration | Effect of inhibiting adhesion (%) |
| --- | --- | --- |
| 5-ASA (positive control) | 20 mM | 18.93 |
| *Aucklandia lappa* Decne (distilled water) | 100 μg/mL | 25.21 |
| *Zingiber officinale* Rosc. | 100 μg/mL | 12.36 |
| *Aucklandia lappa* Decne + *Zingiber officinale* Rosc. | 100 μg/mL | 44.15 |

1-2: Effect of Inhibiting Inflammatory Cytokine Production

An attempt was made to confirm the effect of the mixed extract of the present invention containing *Aucklandia lappa* Decne and *Zingiber officinale* Rosc. on the inhibition of the production of inflammatory cytokines.

(1) Effect of Inhibition of TNF-α Production

As a result of examining the TNF-α concentration, it was confirmed that TNF-α expression levels were significantly lower in the sample and the control group compared to the group treated with LPS alone. In the case of 5-ASA used as the control group, it was shown to inhibit TNF-α production by 11.09%, and dexamethasone was shown to inhibit TNF-α production by 38.46%.

Figure 2:
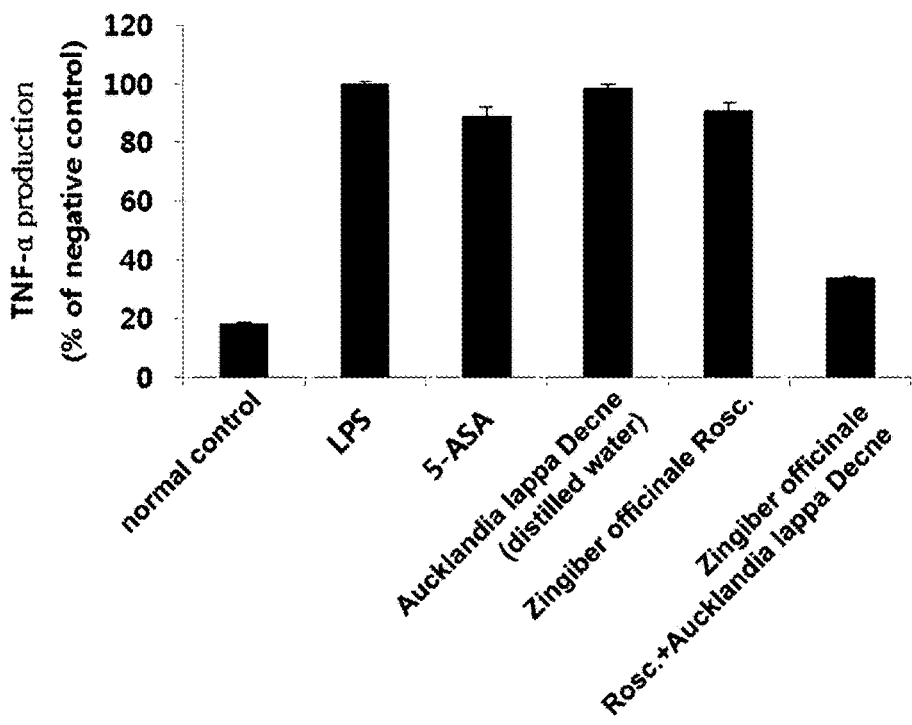
FIG. 2 shows a graph illustrating the inhibitory effect of a mixed extract containing *Aucklandia lappa* Decne and *Zingiber officinale* Rosc. on TNF-α production.

In the case of a single extract of *Aucklandia lappa* Decne (distilled water) and a single extract of *Zingiber officinale* Rosc., the inhibitory effect was shown to be 8.76% and 18.87%, respectively, whereas the extract of the present invention was shown to inhibit TNF-α production by 65.9% (Table 2, FIG. 2).

TABLE 2

| Category | Concentration | Effect of inhibiting TNF-α (%) |
| --- | --- | --- |
| 5ASA | 20 mM | 11.09 |
| Dexamethasone | 20 μM | 38.46 |
| *Aucklandia lappa* Decne (distilled water) | 100 μg/mL | 8.76 |
| *Zingiber officinale* Rosc. | 100 μg/mL | 18.87 |
| *Aucklandia lappa* Decne + *Zingiber officinale* Rosc. | 100 μg/mL | 65.90 |

(2) Effect of Inhibition of IL-6 Production

Additionally, as a result of examining the IL-6 concentration, it was confirmed that IL-6 expression levels were significantly lower in the sample and the control group compared to the group treated with LPS alone. In the case of 5-ASA used as the control group, it was shown to inhibit IL-6 production by 52.78%, and dexamethasone was shown to inhibit IL-6 production by 49.89%.

Figure 3:
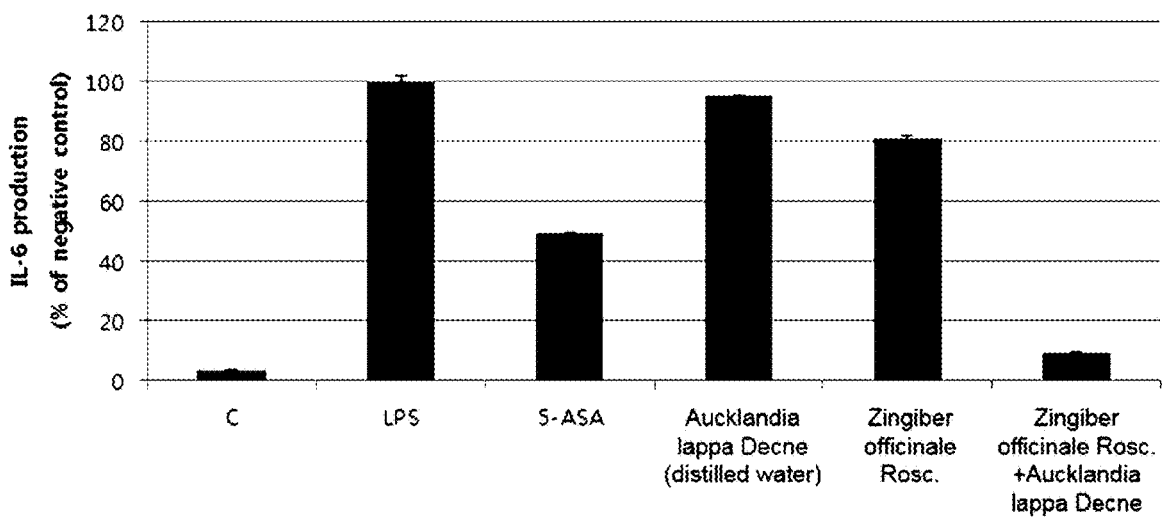
FIG. 3 shows a graph illustrating the inhibitory effect on IL-6 production of a mixed extract containing *Aucklandia lappa* Decne and *Zingiber officinale* Rosc.

In the case of a single extract of *Aucklandia lappa* Decne (distilled water) and a single extract of *Zingiber officinale* Rosc., the inhibitory effect was shown to be 5.40% and 19.53%, respectively, whereas the extract of the present invention was shown to inhibit IL-6 production by 94.05% (Table 3, FIG. 3).

TABLE 3

| Category | Concentration | Effect of inhibiting IL-6 (%) |
| --- | --- | --- |
| 5ASA | 20 mM | 52.78 |
| dexamethasone | 20 μM | 49.89 |
| *Aucklandia lappa* Decne (distilled water) | 100 μg/mL | 5.40 |
| *Zingiber officinale* Rosc. | 100 μg/mL | 19.53 |
| *Aucklandia lappa* Decne + *Zingiber officinale* Rosc. | 100 μg/mL | 94.05 |

From these results, it was confirmed that the inhibitory effect of the extract of the present invention on inflammatory cytokines was greater than that of the control group. Additionally, the inhibitory effect of the mixed extract of the present invention was shown to be higher than those of a single extract of *Zingiber officinale* Rosc. and a single extract of *Aucklandia lappa* Decne (distilled water). From these results it was confirmed, as a result of in vitro experiment on inhibition of cytokine production with respect to IBD, that the mixed extracts of the present invention was shown to have an excellent anti-inflammatory effect.

1-3: Effect of Ameliorating Colitis in DSS Animal Model

The mixed extract of the present invention containing *Aucklandia lappa* Decne and *Zingiber officinale* Rosc. was shown to have the effects of treating and ameliorating colitis in an animal model of DSS inflammatory bowel disease.

Figure 4:
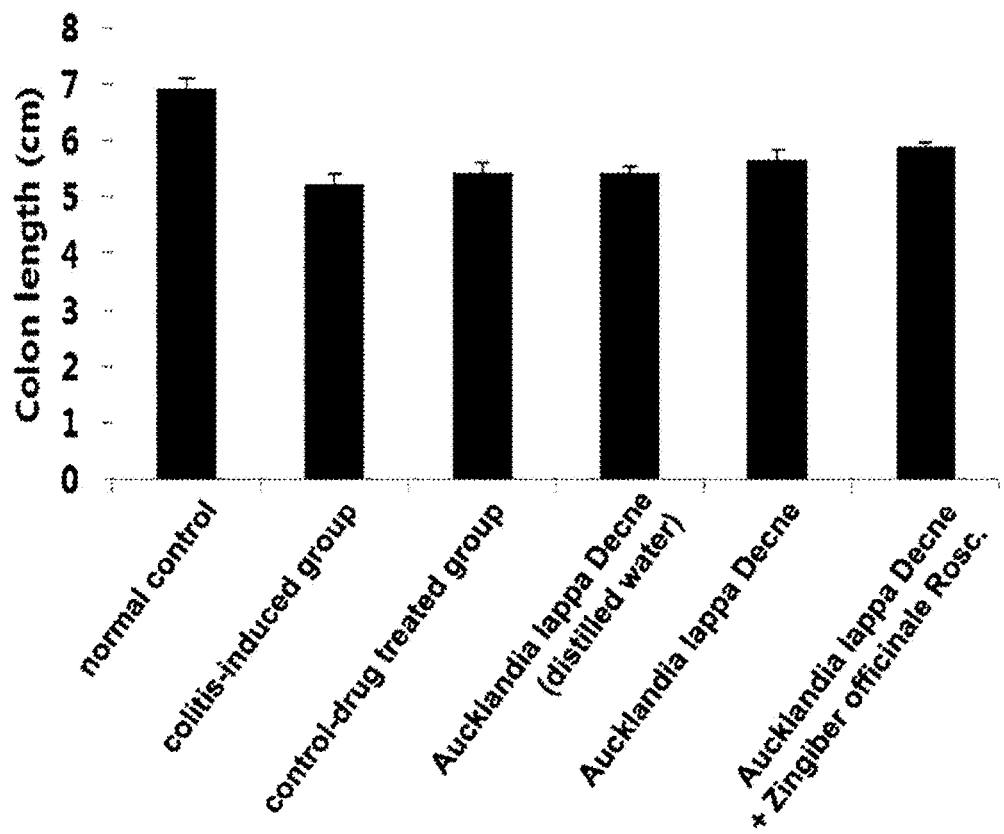
FIG. 4 shows a graph illustrating the effect of recovering the colon length of a mixed extract containing *Aucklandia lappa* Decne and *Zingiber officinale* Rosc. in an animal model of dextran sodium sulfate (DSS)-induced colitis.

From the results of examining the colon length, it was confirmed that the colon length in the colitis-induced group was shown to be about 1.7 cm shorter than that in the normal group. In the control drug-treated group, the colon length was increased by 3.6% compared to the colitis-induced group. The single extract of *Aucklandia lappa* Decne showed an increase in the colon length by 8.22% compared to the colitis-induced group, whereas the group treated with the mixed extract of the present invention showed an increase of the colon length by 12.8% compared to the colitis-induced group (Table 5, FIG. 4).

Figure 5:
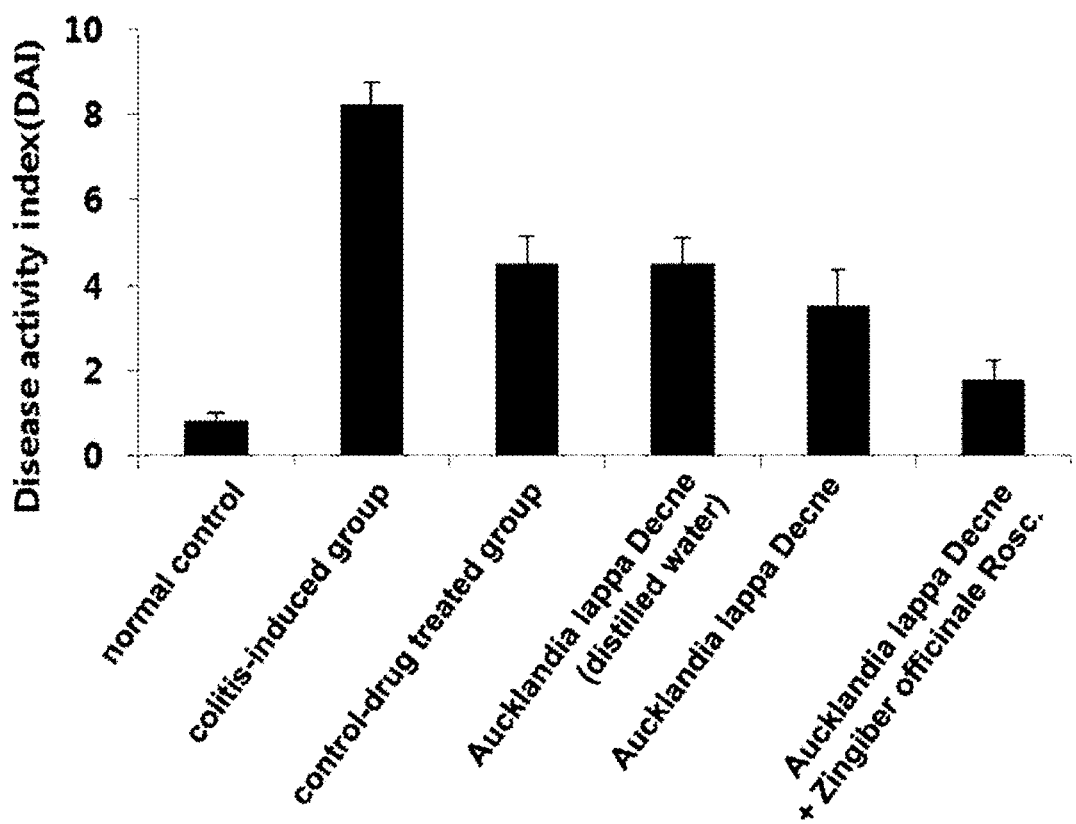
FIG. 5 shows a graph illustrating the disease activity index (DAI) with respect to ameliorating loss of body weight, the conditions in diarrhea and melanain by a mixed extract containing *Aucklandia lappa* Decne and *Zingiber officinale* Rosc. in an animal model of DSS-induced colitis.

Additionally, as a result of expressing the disease activity index by observing the external appearances (Table 4), diarrhea and melena were discovered in the colitis-induced group thus showing a higher score of 8.25, whereas the control drug-treated group showed an effect of improvement by 45% compared to the colitis-induced group. In the case of a single extract of *Aucklandia lappa* Decne, the effect was by about 57.57% compared to the colitis-induced group, whereas the group treated with the mixed extracts of the present invention showed an effect of improvement equal to or higher than the control drug-treated group and groups treated with a single extract (Table 5, FIG. 5).

TABLE 4

| Score | Weight Loss (%) | Concentration of Feces | Degree of Bleeding |
| --- | --- | --- | --- |
| 0 | None | Moderate | None |
| 1 | 1-5 | | |
| 2 | 5-10 | Diluted | Potential Bleeding |
| 3 | 10-20 | | |
| 4 | >20 | Diarrhea | Heavy Bleeding |

TABLE 5

| Category | Colon Length | DAI |
| --- | --- | --- |
| Normal Control Group | 6.9 | 0.83 |
| Colitis-induced Group | 5.23 | 8.25 |
| Control drug-treated Group | 5.42 | 4.50 |
| Aucklandia lappa Decne (distilled water) | 5.42 | 4.50 |
| Aucklandia lappa Decne | 5.66 | 3.50 |
| Aucklandia lappa Decne + Zingiber officinale Rosc. | 5.90 | 1.75 |

In addition, as a result of obtaining and examining the intestinal mucosal tissues by immunostaining, it was confirmed that the DSS animal showed more empty space due to necrosis of the intestinal mucosa compared to the intestinal mucosa of normal animals.

Figure 6:
FIG. 6 shows images illustrating the effect of recovering intestinal mucosa by a mixed extract containing *Aucklandia lappa* Decne and *Zingiber officinale* Rosc. in an animal model of DSS-induced colitis.
Figure 6:
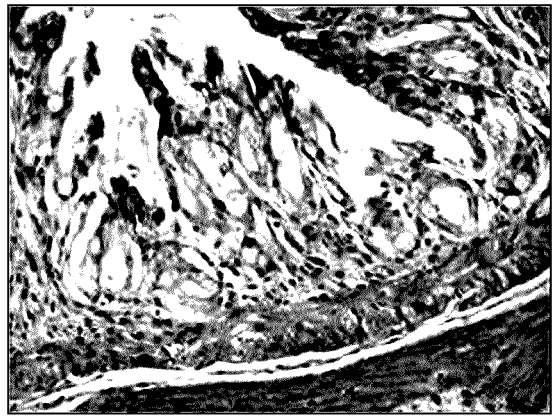
Figure 6:
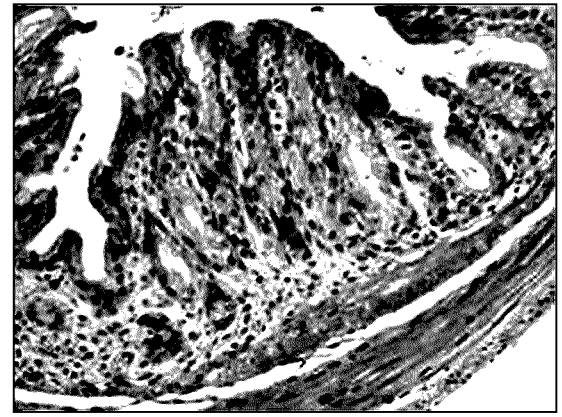
Figure 6:
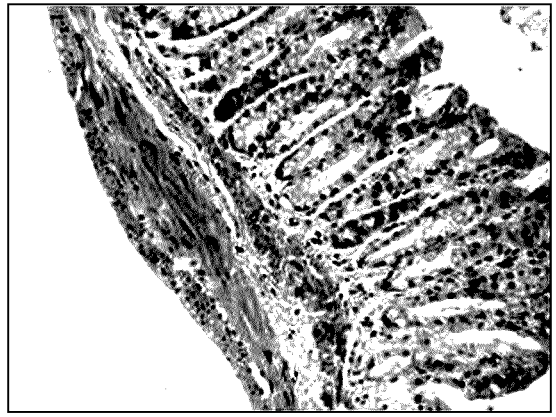

When the control group was administered, it was confirmed that the intestinal mucosa was partially restored, however, when compared with the normal group, a part of the intestinal mucosa was still not recovered. In contrast, when a mixed extract of the present invention was administered, it was confirmed that the intestinal mucosa was recovered to a degree similar to that of the normal group, and thus it was found that the mixed extracts of the present invention has an excellent effect on the recovery of the damaged intestinal mucosa (FIG. 6).

Additionally, as a result of myeloperoxidase (WO) activity assay to determine the status of oxidative stress in immune diseases, in the colitis-induced group, the MPO activity level was about 0.85, but MPO activity was decreased by 17.6% and 23.5% in the control drug-treated group and the group treated with a single extract of Aucklandia lappa Decne, respectively.

Figure 7:
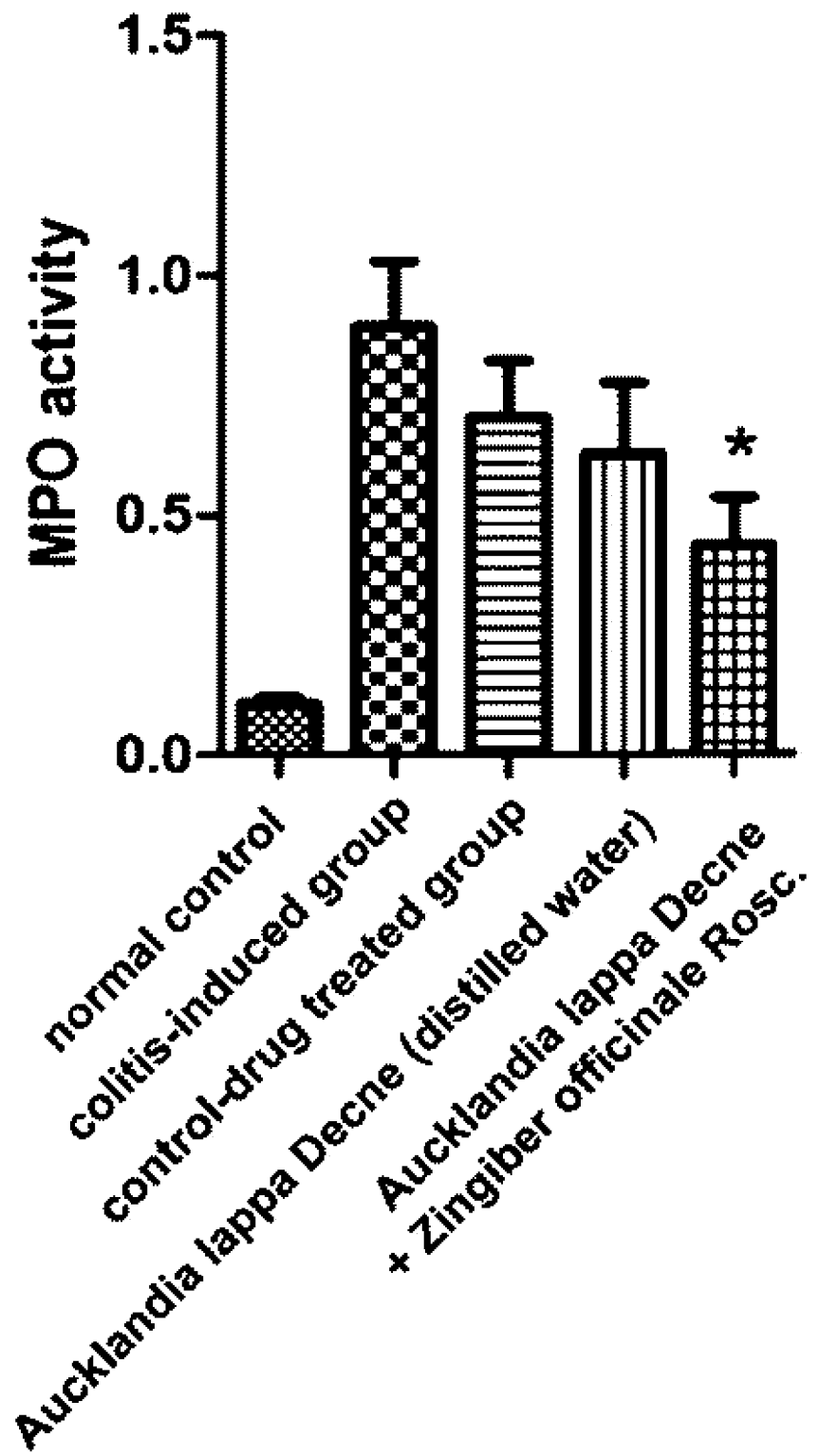
FIG. 7 shows a graph illustrating the effect of reducing myeloperoxidase (MPO) activity by a mixed extract containing *Aucklandia lappa* Decne and *Zingiber officinale* Rosc.

The mixed extracts of the present invention showed an effect of reducing the MPO activity by about 52.9% compared with the colitis-induced group, confirming that the mixed extracts of the present invention has more excellent effect of inhibiting oxidative stress than the single extract of the control group and the group treated with a single extract of Aucklandia lappa Decne (FIG. 7).

Through these results, it was confirmed that the mixed extract of the present invention containing Aucklandia lappa Decne and Zingiber officinale Rosc. exhibits an excellent anti-inflammatory effect and an effect of ameliorating colitis, and thus can be effectively used for the prevention and treatment of inflammatory bowel disease.

Furthermore, in order to identify the conditions of a mixed extract which show more optimal effect, the effects were examined by changing solvent concentrations and mixing ratios.

1-4: Cytotoxicity Test of Mixed Extracts of Aucklandia lappa Decne and Zingiber officinale Rosc. According to Solvent Concentrations (1) MTT Assay The cytotoxicity of the mixed extract of the present invention containing Aucklandia lappa Decne and Zingiber officinale Rosc. was compared according to ethanol concentration contained in the solvent.

Figure 8:
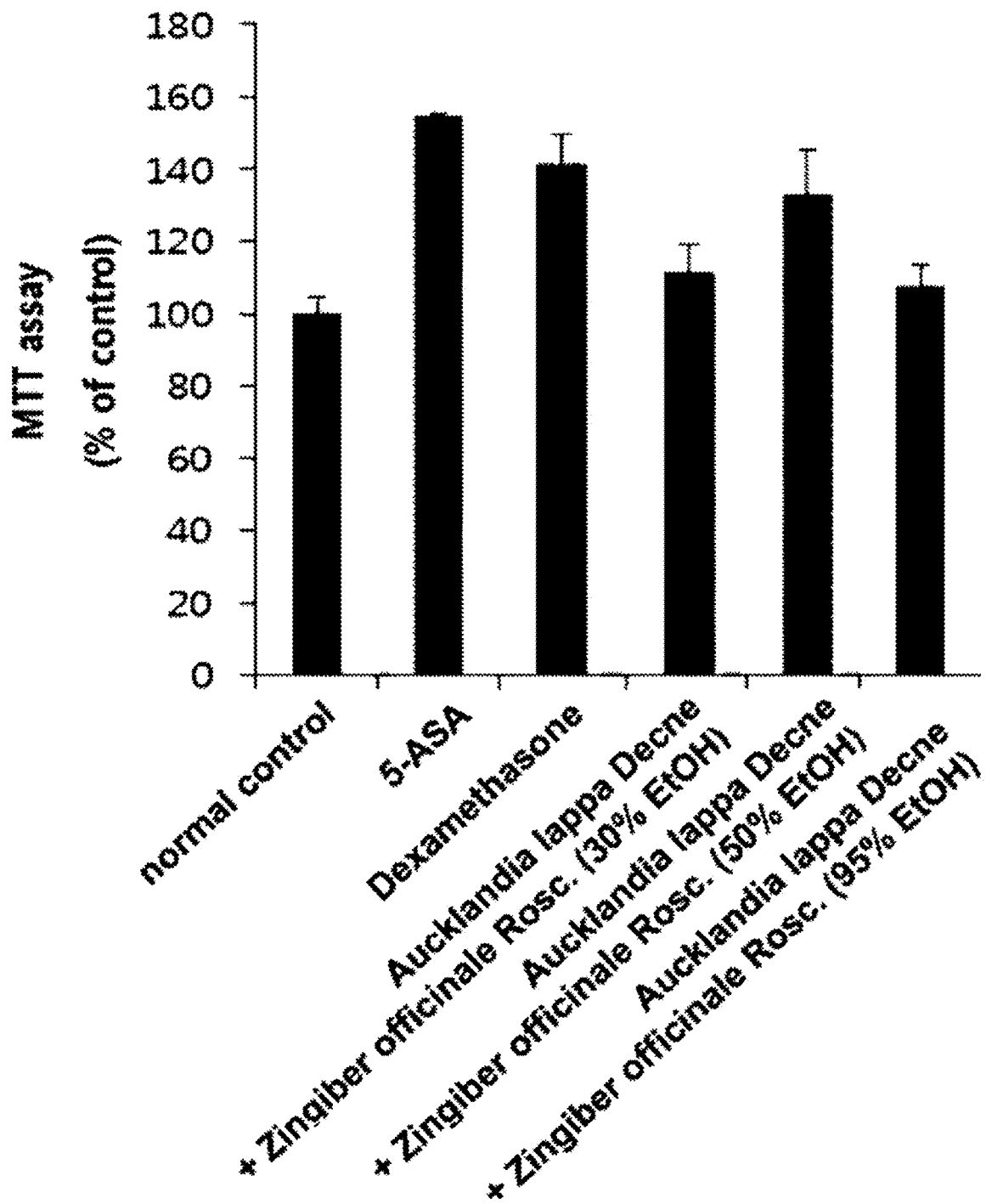
FIG. 8 shows a graph illustrating the results of cytoxicity assay (MTT assay) of a mixed extract containing *Aucklandia lappa* Decne and *Zingiber officinale* Rosc. according to an ethanol concentration of the solvent used for the mixed extract.

As a result, it was confirmed that the 30%, 50%, and 95% ethanol extracts showed no cytotoxicity. In particular, the 50% ethanol extract showed an increase in cell viability by about 330% as compared with the control, and promoted the proliferation of cells (FIG. 8).

It was confirmed that there was no significant difference in cytotoxicity according to ethanol concentration. Among them, 50% ethanol extract promoted cell proliferation, and it was thus confirmed to be effective for cell proliferation in the case of deficiency such as cell death due to inflammation.

(2) Effect of Inhibiting NO Production

Furthermore, the effects of the mixed extract of the present invention containing Aucklandia lappa Decne and Zingiber officinale Rosc. on the inhibition of NO production were compared according to ethanol concentration contained in the solvent.

Figure 9:
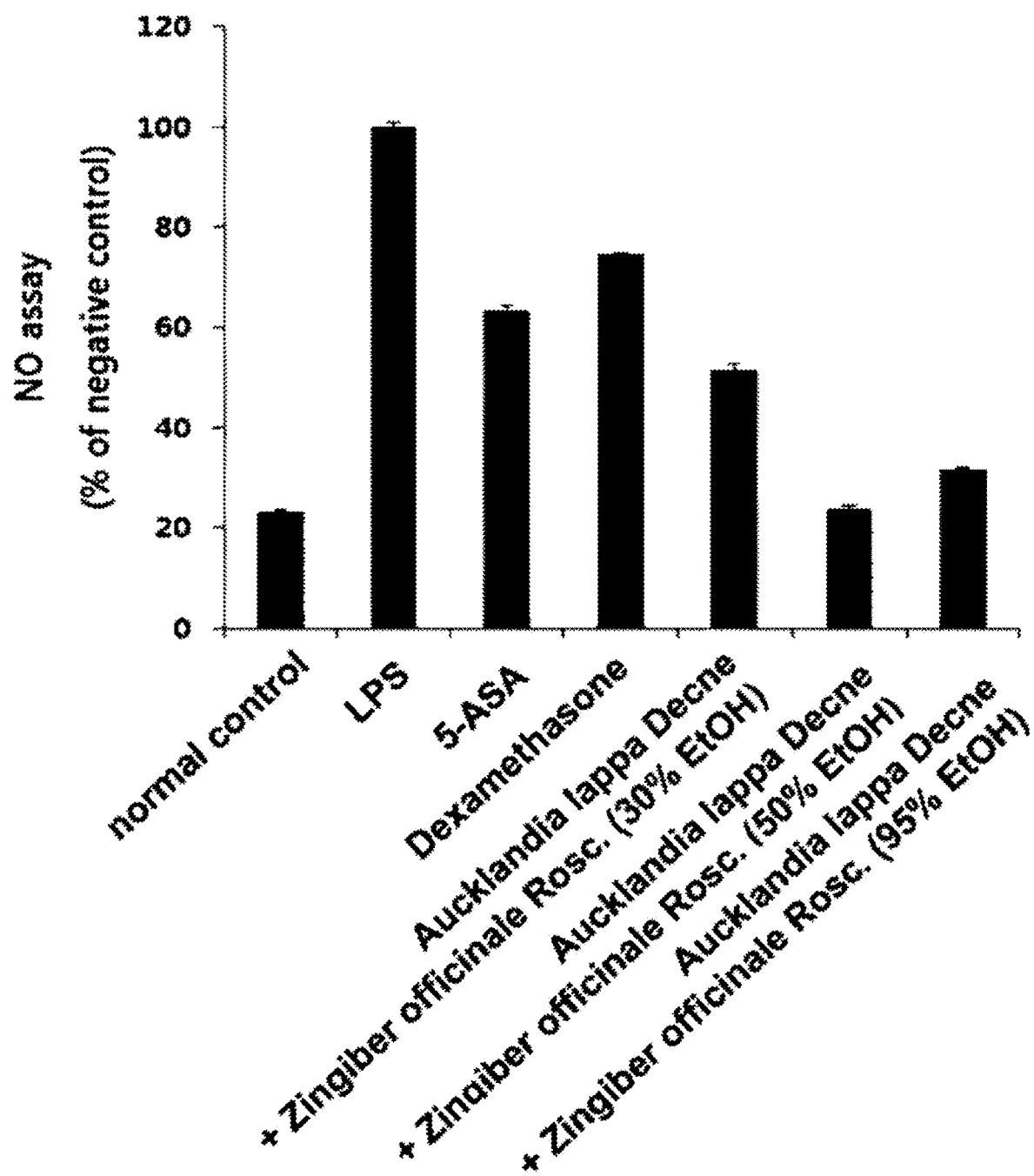
FIG. 9 shows a graph illustrating the inhibitory effect on NO production of a mixed extract containing *Aucklandia lappa* Decne and *Zingiber officinale* Rosc. according to an ethanol concentration of the solvent used for the mixed extract.

As a result, it was confirmed that the 30% ethanol extracts showed an inhibitory effect of 48% against NO production, and the 50% ethanol extract and the 95% ethanol extract showed an inhibitory effect of 76% and 68% against NO production, respectively. These results confirm that the mixed extracts of the present invention has a more excellent inhibitory effect against NO production compared to the 37% inhibitory effect by the control group (5-ASA) (FIG. 9).

Through these results, it was confirmed that the inhibitory effect according to ethanol concentration on NO production was more excellent than that of the positive control group. In particular, the 50% ethanol extract showed the most excellent inhibitory effect against NO production.

According to the results of Example 1-4, the mixed extract of Aucklandia lappa Decne and Zingiber officinale Rosc. extracted using 50% ethanol solvent, which was confirmed to promote cell proliferation without cytotoxicity and exhibited the most excellent inhibitory effect against NO production, was used in the subsequent Examples so as to confirm its effect.

1-5: Cytotoxicity Test of According to Blending Ratio of Aucklandia lappa Decne and Zingiber officinale Rosc.

In order to examine the blending ratio which results in the most excellent effect of the mixed extract of the present invention containing Aucklandia lappa Decne and Zingiber officinale Rosc., the cytotoxicity of each mixed extract was confirmed by varying the blending ratio of Aucklandia lappa Decne and Zingiber officinale Rosc.

Figure 10:
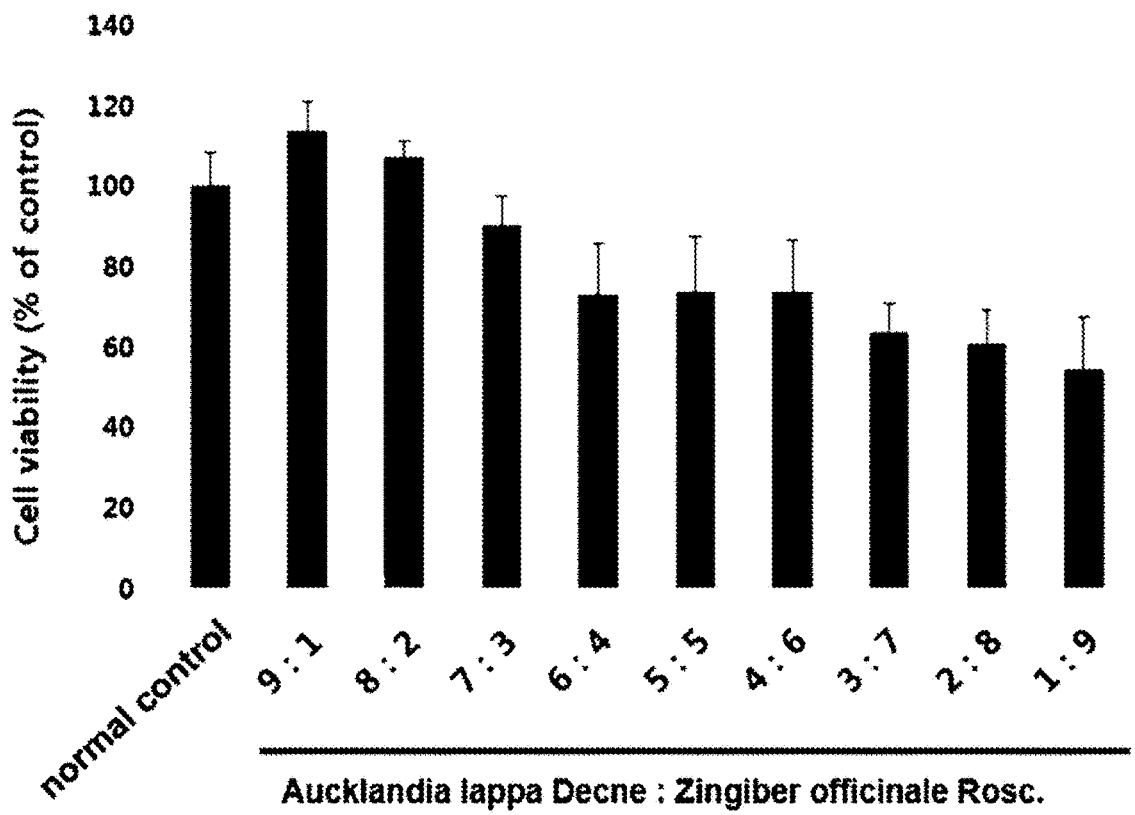
FIG. 10 shows the measurement results of cell viability according to the blending (mixing) ratio of *Aucklandia lappa* Decne and *Zingiber officinale* Rosc.

As a result, it was confirmed that the cytotoxicity was increased as the ratio of Zingiber officinale Rosc. increased (FIG. 10). In particular, when the ratio of Aucklandia lappa Decne:Zingiber officinale Rosc. was in the range of 3:7 to 1:9, the cell viability was shown to be only 60%, whereas when the ratio of Aucklandia lappa Decne:Zingiber officinale Rosc. was in the range of 9:1 to 4:6, the cell viability was shown to be 70% or higher.

Additionally, the effect of each of the mixed extracts against NO production was examined by varying the blending ratio of Aucklandia lappa Decne and Zingiber officinale Rosc.

Figure 11:
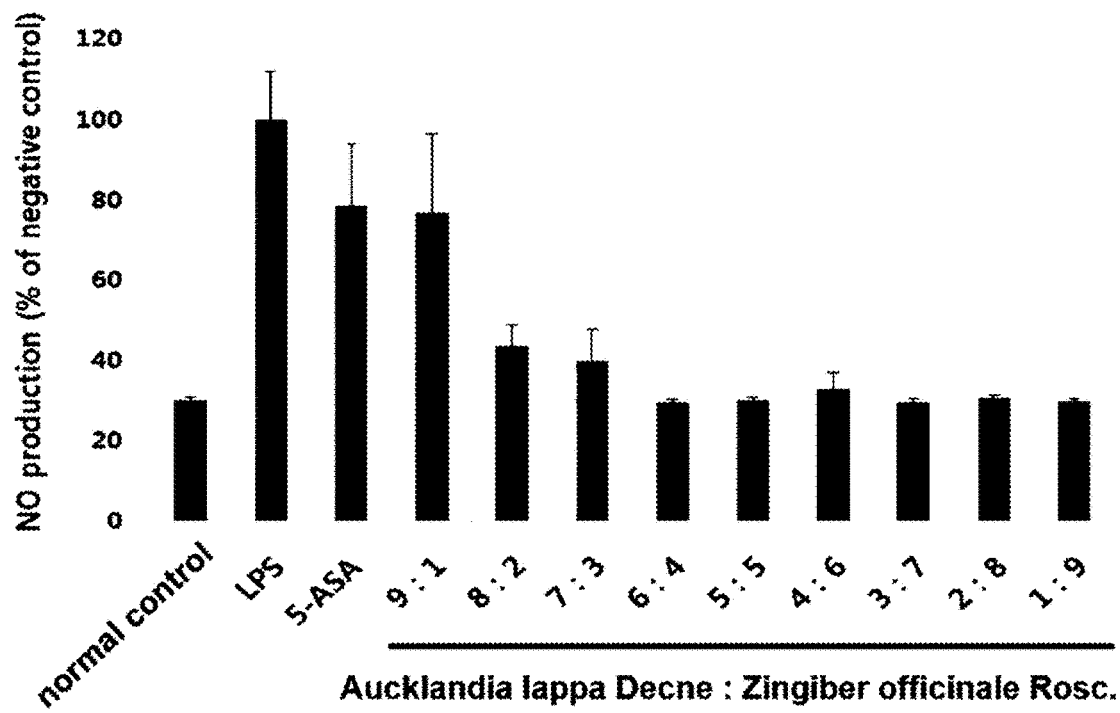
FIG. 11 shows the measurement results of the inhibitory effect on NO production according to the blending (mixing) ratio of *Aucklandia lappa* Decne and *Zingiber officinale* Rosc.

In the mixed extracts, the inhibitory effect against NO production was increased as the ratio of Zingiber officinale Rosc. Among them, when the ratio of Aucklandia lappa Decne:Zingiber officinale Rosc. was in the range of 6:4 to 1:9, the inhibitory effect against NO production was confirmed to be 70% or higher (FIG. 11). In particular, preferably, when the ratio of Aucklandia lappa Decne:Zingiber officinale Rosc. was 6:4 or 5:5, it was confirmed that NO production, which is important in inflammation, was inhibited.

1-6: Inhibitory Effect on Monocyte Adhesion in Intestinal Epithelial Cells According to Blending Ratio of Aucklandia lappa Decne and Zingiber officinale Rosc.

In order to examine the blending ratio which results in the most excellent effect of the mixed extract of the present invention containing Aucklandia lappa Decne and Zingiber officinale Rosc., the effect of each mixed extract on the inhibition of infiltration of monoxytes was confirmed by varying the blending ratio of *Aucklandia lappa* Decne and *Zingiber officinale* Rosc.

Figure 12:
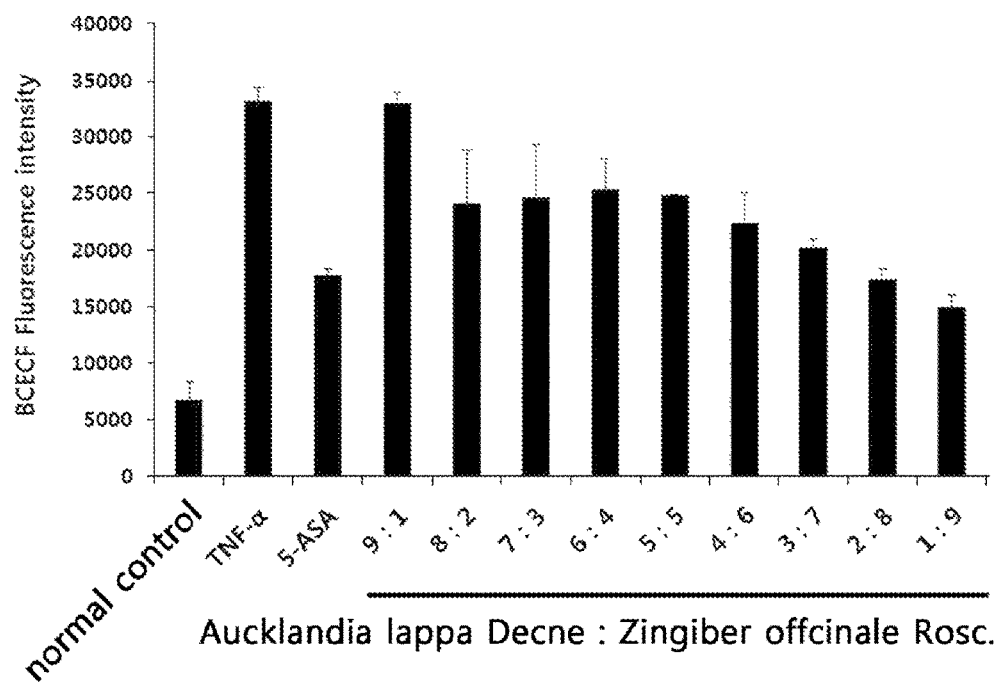
FIG. 12 shows a graph illustrating the inhibitory effect on monocyte adhesion according to the blending (mixing) ratio of *Aucklandia lappa* Decne and *Zingiber officinale* Rosc. in intestinal epithelial cells.

As shown in FIG. 12, in a case of mixed extract where the blending ratio of *Aucklandia lappa* Decne and *Zingiber officinale* Rosc. was varied, it was confirmed that the infiltration of monoxytes was inhibited as the ratio of *Zingiber officinale* Rosc. increased. It was also confirmed that when the ratio of *Aucklandia lappa* Decne:*Zingiber officinale* Rosc. was 5:5, the inhibitory effect was 25.06%, where when the ratio of *Aucklandia lappa* Decne:*Zingiber officinale* Rosc. was 6:4, the inhibitory effect was 32.5%.

The blending ratio, in which no cytotoxicity was shown but most excellent effects of inhibiting NO production and inhibiting the infiltration of monocytes, was when the ratio of *Aucklandia lappa* Decne:*Zingiber officinale* Rosc. was 6:4 or 5:5 (i.e., 1:1).

Example 2: Confirmation of Effect of Mixed Extract of *Aucklandia lappa* Decne and *Terminalia chebula* Retzius Meanwhile, the present inventors have performed the following experiment using a mixed extract of *Aucklandia lappa* Decne and *Terminalia chebula* retzius.

2-1: Inhibitory Effect on Monocyte Adhesion in Intestinal Epithelial Cells

In the present invention, the effect of mixed extract of *Aucklandia lappa* Decne and *Terminalia chebula* Retzius on infiltration of monocytes was confirmed.

Figure 13:
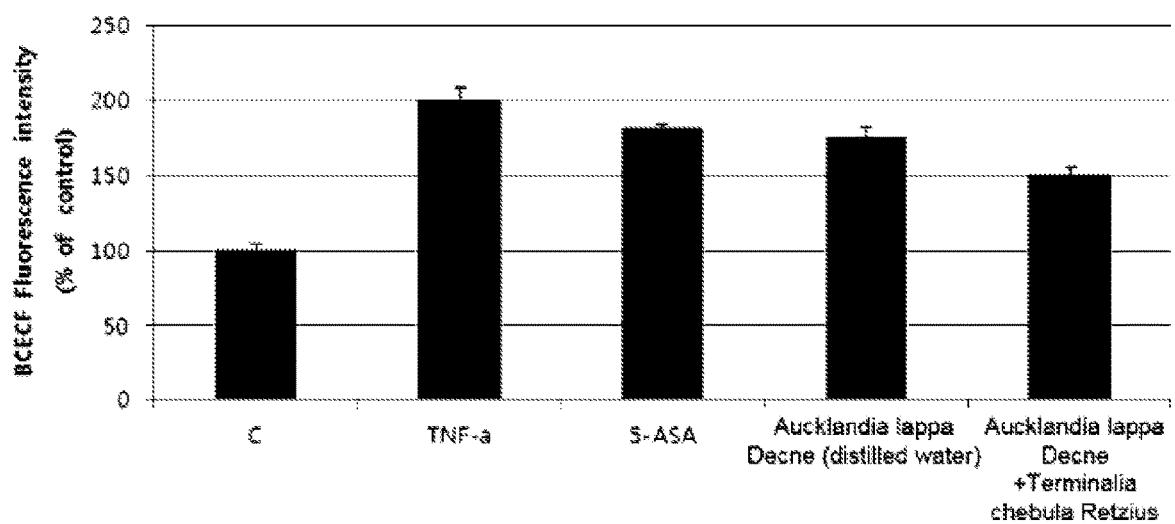
FIG. 13 shows a graph illustrating the inhibitory effect on monocyte adhesion in intestinal epithelial cells of a mixed extract containing *Aucklandia lappa* Decne and *Terminalia chebula* Retzius.

The fluorescent-labeled U937 cell adhesion to the HT-29 intestinal epithelial cells was significantly increased by TNF-α stimulus, and the cell adhesion was inhibited by 19.94% by the control drug (5-ASA). In the case of a single extract of *Aucklandia lappa* Decne (distilled water), the inhibitory effect was shown to be 15.21%. However, in the case of the mixed extract of the present invention, the inhibitory rate was 21.18% thus confirming that the mixed extracts of the present invention has an effect being equal to or higher compared to that of the control drug (Table 6, FIG. 13).

Additionally, the mixed extract of the present invention was shown to have more excellent effect compared to the single extract of *Aucklandia lappa* Decne (distilled water). Through these results, it was confirmed that the mixed extract effectively inhibit the infiltration of monocytes comparable to that of the control drug.

TABLE 6

| Category | Concentration | Effect of Inhibiting Adhesion (%) |
| --- | --- | --- |
| 5-ASA (positive control) | 20 mM | 18.93 |
| *Aucklandia lappa* Decne (distilled water) | 100 μg/mL | 25.21 |
| *Aucklandia lappa* Decne + *Terminalia chebula* Retzius | 100 μg/mL | 49.36 |

2-2: Effect of Inhibiting Production of Inflammatory Cytokines (1) Effect of Inhibiting TNF-α Production As a result of examining the effect of the mixed extract of *Aucklandia lappa* Decne and *Terminalia chebula* Retzius of the present invention on the inhibition of TNF-α production, it was confirmed that the expression levels of TNF-α were significantly reduced in the sample and the control drug-treated group compared to the group treated with LPS alone. In the case of 5-ASA, which was used as the control drug, it inhibited TNF-α production by 11.09% and dexamethasone inhibited TNF-α production by 38.46%.

Figure 14:
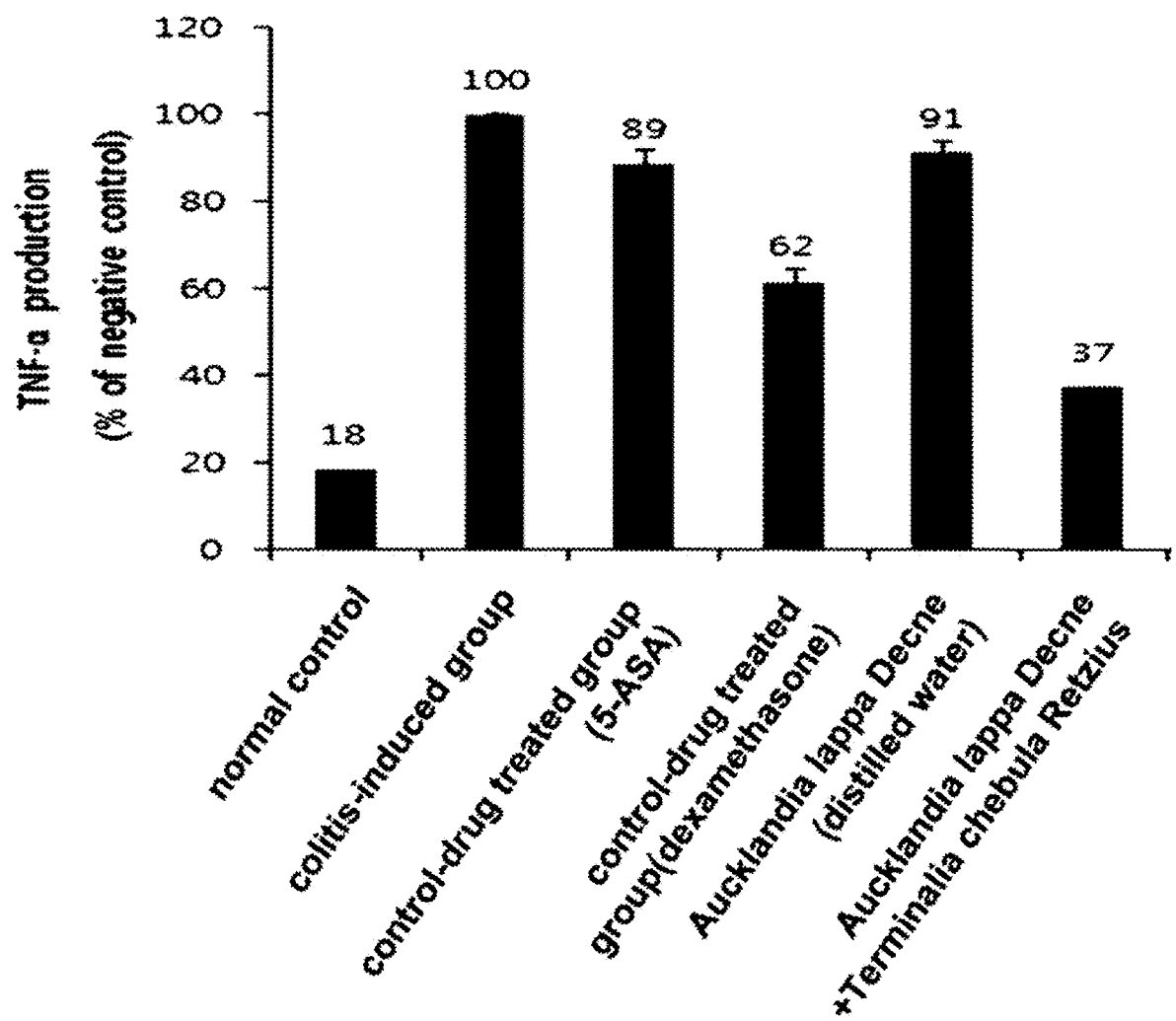
FIG. 14 shows a graph illustrating the inhibitory effect on LPS-induced production of TNF-α (i.e., an inflammatory cytokine) of a mixed extract containing *Aucklandia lappa* Decne and *Terminalia chebula* Retzius.

The single extract of *Aucklandia lappa* Decne (distilled water) respectively showed an inhibitory effect of 8.76%, where the mixed extract of the present invention showed an inhibitory effect against TNF-α production by 62.71% (Table 7, FIG. 14).

TABLE 7

| Category | Concentration | Effect of Inhibiting TNF-α (%) |
| --- | --- | --- |
| 5-ASA (positive control) | 20 mM | 11.09 |
| Dexamethasone (positive control) | 20 μM | 38.46 |
| *Aucklandia lappa* Decne (distilled water) | 100 μg/mL | 8.76 |
| *Aucklandia lappa* Decne + *Terminalia chebula* Retzius | 100 μg/mL | 62.71 |

(2) Effect of Inhibiting IL-6 Production

As a result of further examining the IL-6 concentrations, it was confirmed that the expression levels of IL-6 was significantly reduced in the sample and the control drug group compared to the group treated with LPS alone. In the case of 5-ASA, which was used as the control drug, it inhibited IL-6 production by 67.68% and dexamethasone inhibited IL-6 production by 49.89%.

Figure 15:
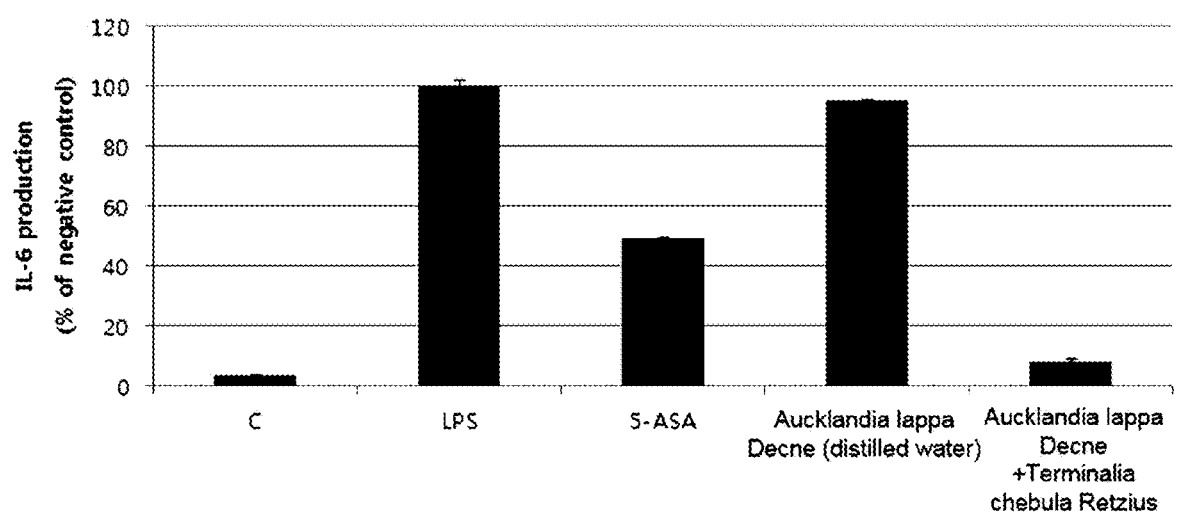
FIG. 15 shows a graph illustrating the inhibitory effect on LPS-induced production of IL-6 (i.e., an inflammatory cytokine) of a mixed extract containing *Aucklandia lappa* Decne and *Terminalia chebula* Retzius.

The single extract of *Aucklandia lappa* Decne (distilled water) respectively showed an inhibitory effect of 7.48%, where the mixed extract of the present invention showed an inhibitory effect against TNF-α production by 95.19% (Table 8, FIG. 15).

TABLE 8

| Category | Concentration | Effect of Inhibiting IL-6 (%) |
| --- | --- | --- |
| 5-ASA (positive control) | 20 mM | 52.78 |
| Dexamethasone (positive control) | 20 μM | 49.89 |
| *Aucklandia lappa* Decne (distilled water) | 100 μg/mL | 5.40 |
| *Aucklandia lappa* Decne + *Terminalia chebula* Retzius | 100 μg/mL | 95.08 |

2-3: Effect of Ameliorating Colitis in DSS Animal Model

An attempt was made to examine the effect of mixed extract of *Aucklandia lappa* Decne and *Terminalia chebula* Retzius of the present invention on the treatment and amelioration of colitis in an animal model of DSS inflammatory bowel disease.

Figure 16:
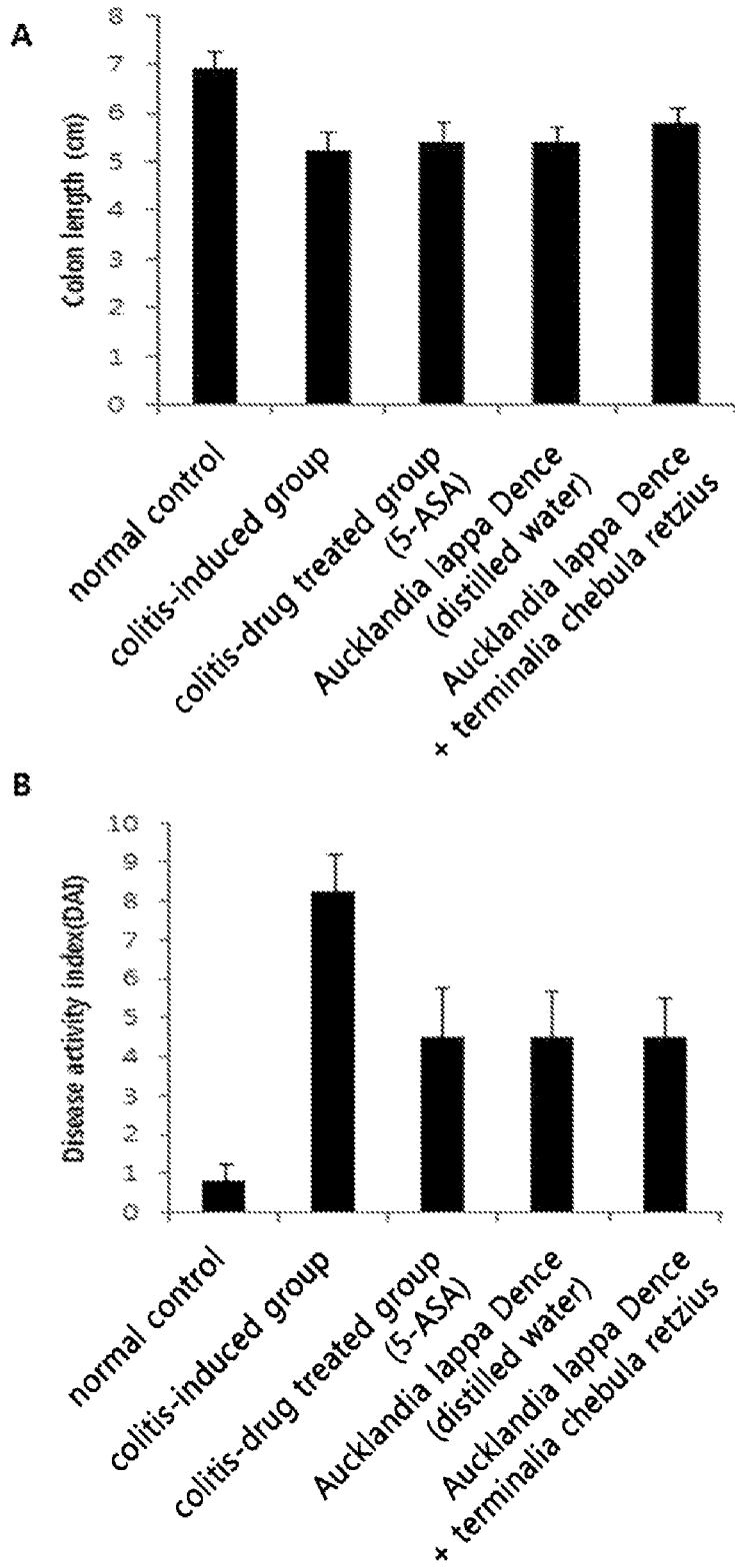
FIG. 16 shows a graph illustrating the effect of a mixed extract containing *Aucklandia lappa* Decne and *Terminalia chebula* Retzius in an animal model of DSS-induced colitis.

From the results of examining the colon length, it was confirmed that the colon length in the colitis-induced group was shown to be about 1.7 cm shorter than that in the normal group. In the control drug-treated group, the colon length was increased by 3.6% compared to the colitis-induced group. The single extract of *Aucklandia lappa* Decne showed an increase in the colon length by 8.22% compared to the colitis-induced group, whereas the group treated with the mixed extract of the present invention showed an increase of the colon length by 10.5% compared to the colitis-induced group (Table 9, FIG. 16 A).

TABLE 9

| Category | Colon Length (cm) | DAI |
| --- | --- | --- |
| Normal Control Group | 6.9 | 67.68 |
| Colitis-induced Group | 5.23 | 49.89 |
| Control drug-treated Group | 5.42 | 7.48 |
| *Aucklandia lappa* Decne (distilled water) | 5.42 | 95.19 |
| *Aucklandia lappa* Decne + *Terminalia chebula* Retzius | 5.78 | 4.5 |

Additionally, as a result of expressing the disease activity index by observing the external appearances, diarrhea and melena were discovered in the colitis-induced group thus showing a higher score of 8.25, whereas the control drug-treated group showed an effect of improvement by 45% compared to the colitis-induced group. The mixed extract of the present invention showed an effect of improvement by 45% compared to the colitis-induced group thus showing an equivalent effect of improvement to that of the control drug-treated group (Table 9, FIG. 16 B).

Figure 17:
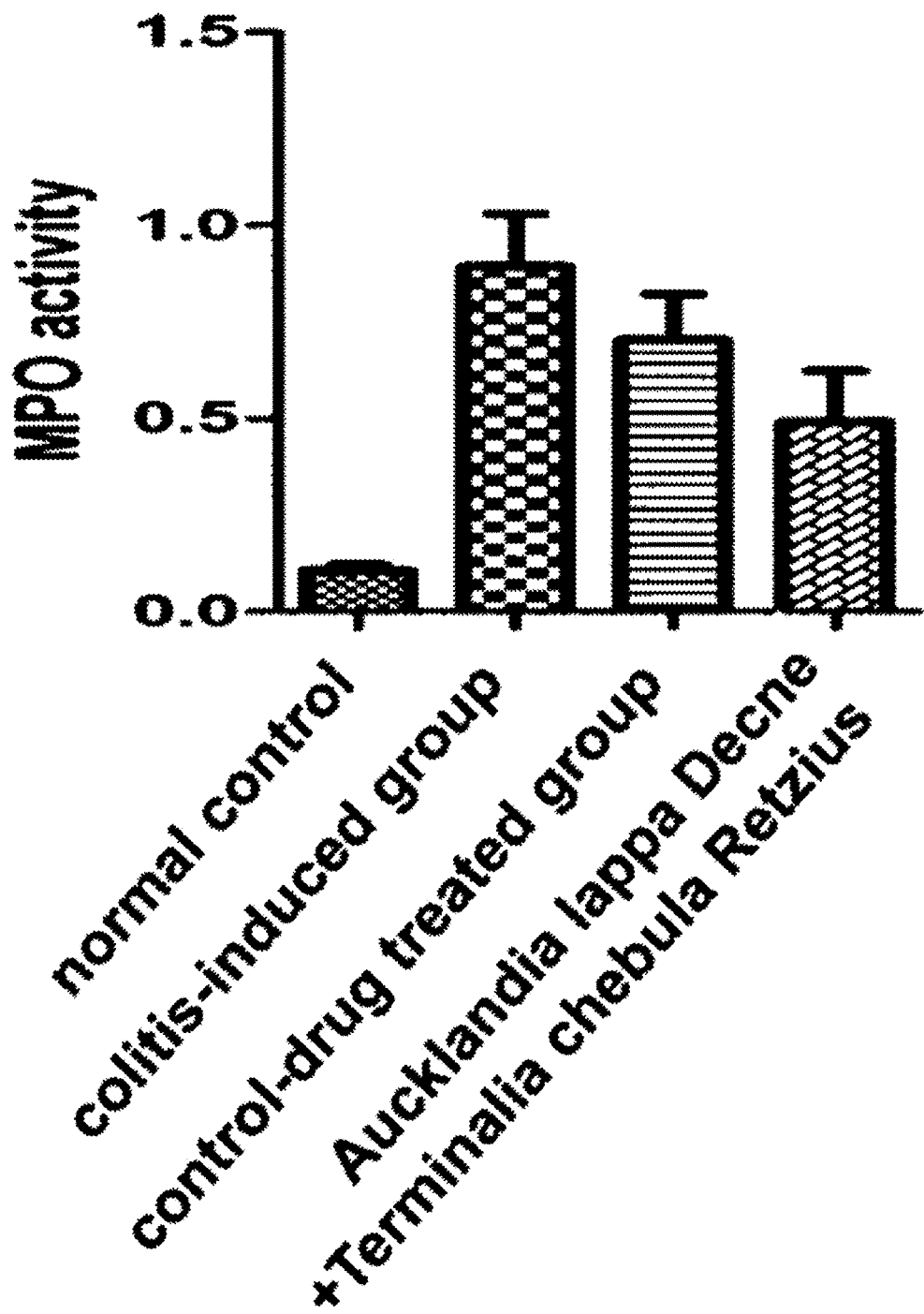
FIG. 17 shows a graph illustrating the activity of myeloperoxidase (MPO) on the inhibition of infiltration of inflammatory cells into intestinal tissue in an animal model of DSS-induced colitis by a mixed extract containing *Aucklandia lappa* Decne and *Terminalia chebula* Retzius.

As a result of myeloperoxidase (MPO) activity assay to determine the status of oxidative stress in immune diseases, in the colitis-induced group, the MPO activity level was about 0.9, but MPO activity was decreased by 22% in the control drug-treated group. The group treated with a mixed extract of the present invention showed an effect of reduced MPO activity by about 50% thus showing a more excellent effect of inhibiting oxidative stress (FIG. 17).

2-4: Effect of Ameliorating Crohn's Disease in TNBS Animal Model

ICR female mice (17 g to 19 g, 6-week old, DBL Co., Ltd. (Eumseong, Korea), 5-aminosalicylic acid (5-ASA), and 2,4,6-trinitro-benzene sulfonic acid (TNBS) were used.

The effect of mixed extract of *Aucklandia lappa* Decne and *Terminalia chebula* Retzius of the present invention on the treatment and amelioration of Crohn's disease in TNBS Crohn's animal model was examined.

As a result of examining the weight of colon per colon length, it was confirmed that the Crohn's disease-induced group had about 37 mg/cm thus showing an increase of about 4 mg/cm to 5 mg/cm compared to the normal group. The control drug-treated group showed almost no difference compared to that of the Crohn's disease-induced group, and this result confirms that the control drug is not effective in reducting the thickened intestinal wall.

In contrast, in the case of a mixed extract of *Aucklandia lappa* Decne and *Terminalia chebula retzius* of the present invention, it was confirmed that the weight of colon per colon length was reduced by about 16% compared to that of the Crohn's disease-induced group, and this result confirmed that the mixed extract of the present invention is effective in reducting the thickened intestinal wall due to Crohn's disease (FIG. 18A).

Figure 18:
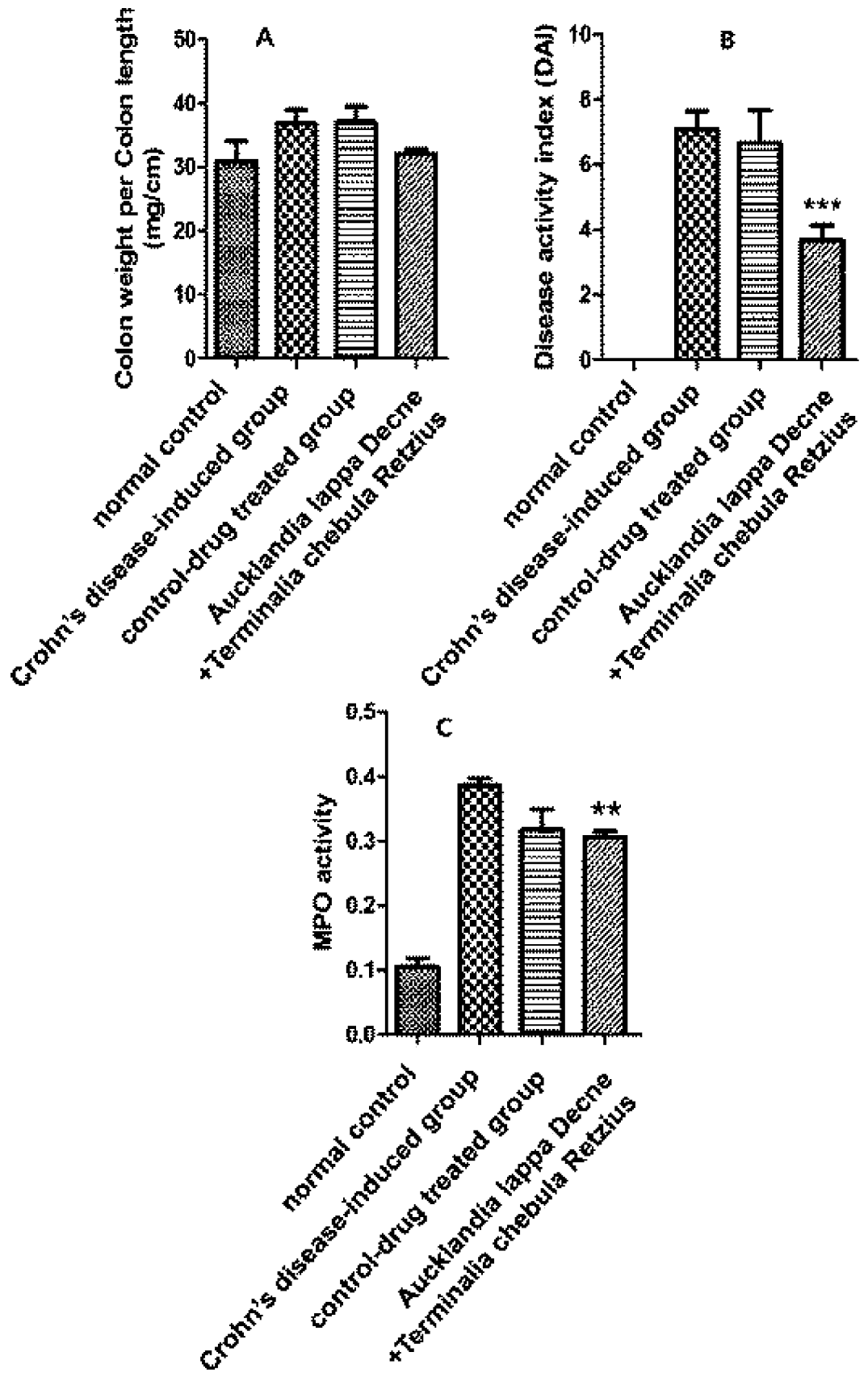
FIG. 18 shows graphs illustrating the effects of a mixed extract containing *Aucklandia lappa* Decne and *Terminalia chebula* Retzius in an animal model of 2,4,6-trinitrobenzenesulfonic acid (TNBS)-induced Crohn's disease.

Additionally, as a result of expressing the disease activity index by observing the external appearances, diarrhea and melena were discovered in the Crohn's disease-induced group thus showing a higher score of 7, whereas the control drug-treated group showed a slight effect of improvement by 7% compared to the Crohn's disease-induced group. However, the mixed extract of the present invention showed an effect of improvement by 45% compared to the Crohn's disease-induced group thus showing a more excellent effect of improvement to that of the control drug-treated group (FIG. 18 B).

As a result of myeloperoxidase (MPO) activity assay to determine the status of oxidative stress in immune diseases, in the Crohn's disease-induced group, the MPO activity level was about 0.38, but MPO activity was decreased by 15% in the control drug-treated group. The group treated with a mixed extract of the present invention showed an effect of reduced MPO activity by about 21% compared to the Crohn's disease-induced group thus showing an effect of inhibiting oxidative stress equal to or higher than the control drug-treated group (FIG. 18 C).

Through these results, it was confirmed that the mixed extract of *Aucklandia lappa* Decne and *Terminalia chebula* Retzius of the present invention shows excellent anti-inflammatory effect and an effect of ameliorating Crohn's disease, and thus, the mixed extract can be effectively used for the prevention or treatment of inflammatory bowel disease.

Example 3: Confirmation of Effect of Mixed Extract of *Zingiber officinale* Rosc. And *Terminalia chebula* Retzius Meanwhile, the present inventors have performed the following experiment using a mixed extract of *Zingiber officinale* Rosc. and *Terminalia chebula* Retzius.

3-1: Inhibitory Effect on Monocyte Adhesion in Intestinal Epithelial Cells

In the present invention, the effect of mixed extract of *Zingiber officinale* Rosc. and *Terminalia chebula* Retzius on inhibiting the infiltration of monocytes was confirmed.

Figure 19:
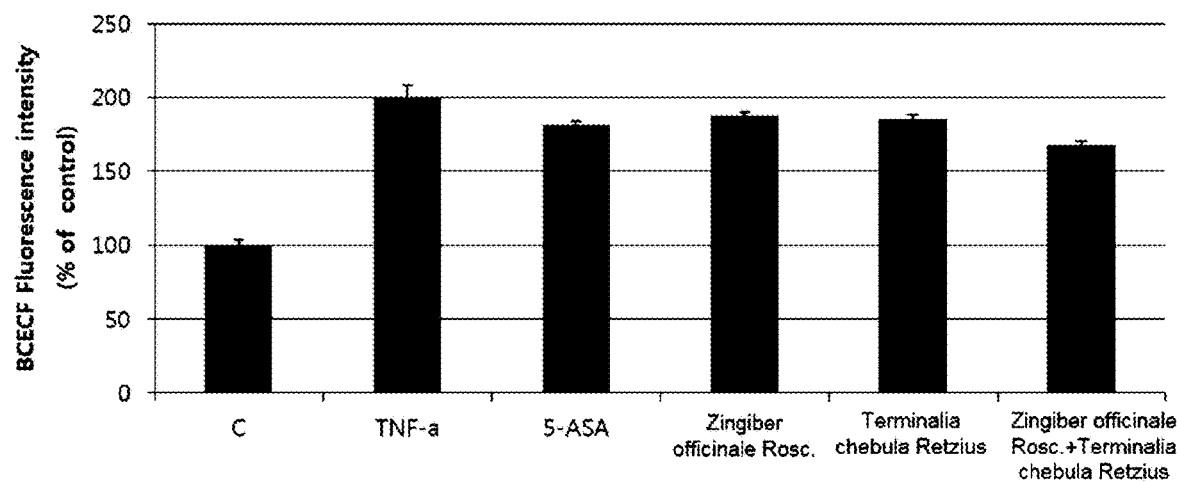
FIG. 19 shows a graph illustrating the inhibitory effect on monocyte adhesion in intestinal epithelial cells of a mixed extract containing *Zingiber officinale* Rosc. and *Terminalia chebula* Retzius.

The fluorescent-labeled U937 cell adhesion to the HT-29 intestinal epithelial cells was significantly increased by TNF-α stimulus, and the adhesion was inhibited by 18.93% by the control drug (5-ASA). In the case of a single extract of *Zingiber officinale* Rosc. or *Terminalia chebula* Retzius, the inhibitory effect was shown to be 12.35% and 14.55%, respectively. However, in the case of the mixed extract of the present invention, the inhibitory rate was 31.76% thus confirming that the mixed extracts of the present invention has an effect being equal to or higher compared to that of the control drug (Table 10, FIG. 19).

Additionally, the mixed extract of the present invention showed an excellent effect compared to single extracts of *Zingiber officinale* Rosc. or *Terminalia chebula* Retzius alone. Through these results, it was confirmed that the mixed extract can effectively inhibit the infiltration of monocytes comparable to that of the control drug.

TABLE 10

| Category | Concentration | Effect of Inhibiting Adhesion (%) |
| --- | --- | --- |
| 5-ASA (positive control) | 20 mM | 18.93 |
| *Zingiber officinale* Rosc. | 100 μg/mL | 12.35 |
| *Terminalia chebula* Retzius | 100 μg/mL | 14.55 |
| *Zingiber officinale* Rosc. + *Terminalia chebula* Retzius | 100 μg/mL | 31.76 |

3-2: Effect of Inhibiting Production of Inflammatory Cytokines

As a result of examining the IL-6 concentrations by the mixed extract of the *Zingiber officinale* Rosc. and *Terminalia chebula* Retzius of the present invention, it was confirmed that the expression levels of IL-6 were significantly reduced in the sample and the control drug-treated group compared to the group treated with LPS alone. The 5-ASA, which was used as the control drug, was shown to inhibit IL-6 production by 50.98%.

Figure 20:
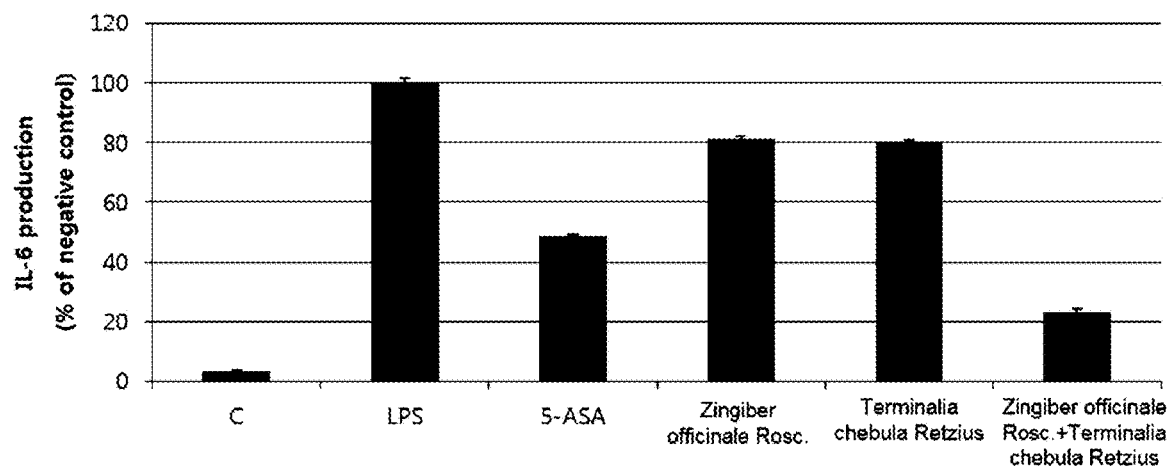
FIG. 20 shows a graph illustrating the inhibitory effect on LPS-induced production of IL-6 (i.e., an inflammatory cytokine) of a mixed extract containing *Zingiber officinale* Rosc. and *Terminalia chebula* Retzius.

Although the single extracts of *Zingiber officinale* Rosc. or *Terminalia chebula* Retzius showed an inhibitory effect of 18.87% and 19.88%, respectively, the extract of the present invention inhibited IL-6 production by 76.55% (Table 11, FIG. 20).

TABLE 11

| Category | Concentration | Effect of Inhibiging IL-6 (%) |
|---|---|---|
| 5-ASA (positive control) | 20 mM | 50.98 |
| *Zingiber officinale* Rosc. | 100 μg/mL | 18.87 |
| *Terminalia chebula* Retzius | 100 μg/mL | 19.88 |
| *Zingiber officinale* Rosc. + *Terminalia chebula* Retzius | 100 μg/mL | 76.55 |

3-3: Effect of Ameliorating Colitis in DSS Animal Model

An attempt was made to confirm the effects of a mixed extract of *Zingiber officinale* Rosc. and *Terminalia chebula* Retzius on the treatment and amelioration of colitis in an animal model of DSS inflammatory bowel disease.

Figure 21:
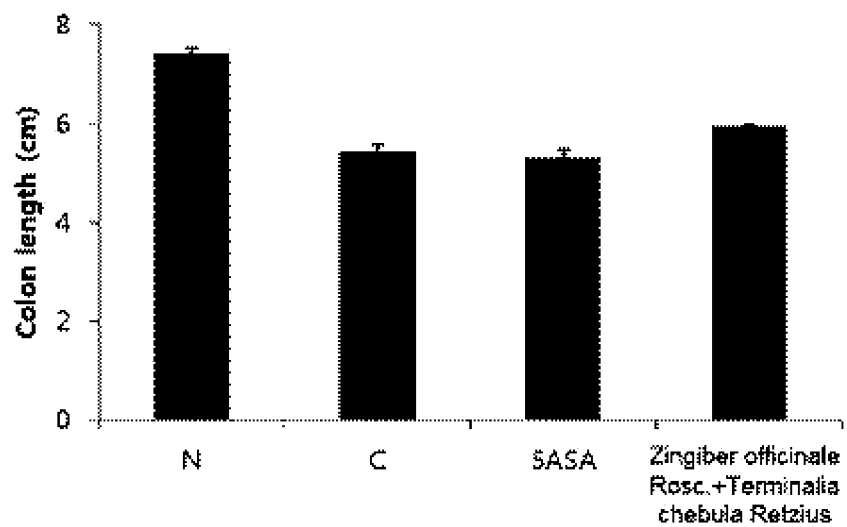
FIG. 21 shows graphs illustrating the effects of a mixed extract containing *Zingiber officinale* Rosc. and *Terminalia chebula* Retzius in an animal model of DSS-induced colitis.
Figure 21:
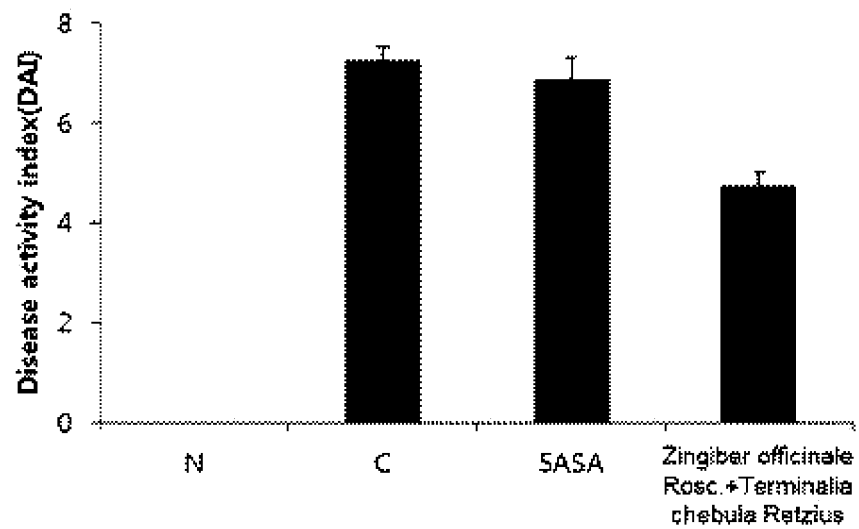
Figure 21:
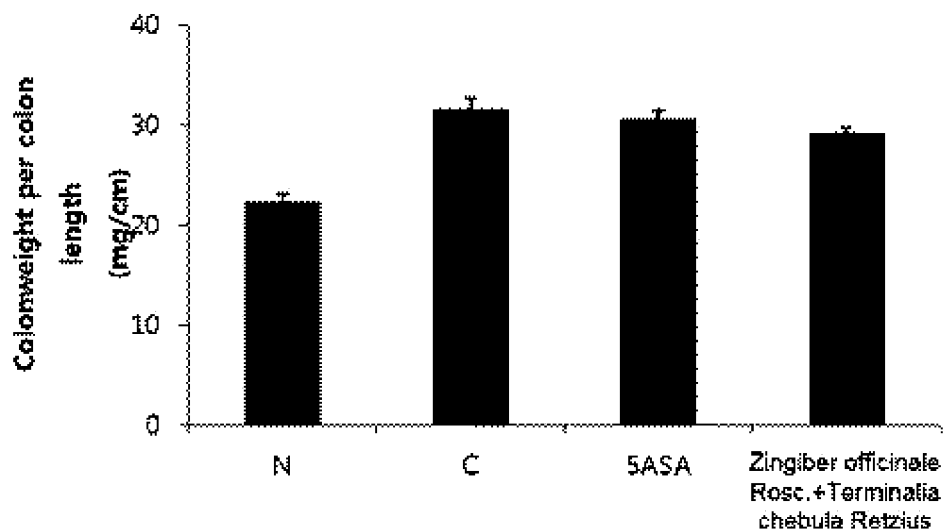

From the results of examining the colon length, it was confirmed that the colon length in a colitis-induced group was reduced by about 2 cm compared to the normal group, and when the mixed extract of the present invention was administered, the colon length was increased by about 9.2% compared to the colitis-induced group (Table 12, FIG. 21 A).

Additionally, as a result of expressing the disease activity index by observing the external appearances, diarrhea and melena were discovered in the colitis-induced group thus showing a higher score of 7.25. The group treated with the mixed extract of the present invention showed a score of 4.75 thus showing an effect of improvement (Table 12, FIG. 21 B).

Additionally, as a result of examining the weight of colon per colon length, it was confirmed that the colitis-induced group had about 32 mg/cm thus showing an increase of about 9 mg/cm compared to the normal group. The group treated with the mixed extract of the present invention, it was confirmed that the weight of colon per colon length was slightly reduced compared to colitis-induced group, and this result confirmed that the mixed extract of the present invention is effective in improving the thickened intestinal wall (Table 12, FIG. 21 C).

TABLE 12

| Category | Colon Length (cm) | DAI | Weight per Area |
|---|---|---|---|
| Normal Control Group | 7.42 ± 0.1 | 0 | 22.25 ± 0.81 |
| Colitis-induced Group | 5.44 ± 0.12 | 7.25 ± 0.25 | 31.51 ± 1.2 |
| Control drug-treated Group | 5.31 ± 0.16 | 6.88 ± 0.44 | 30.66 ± 0.76 |
| *Zingiber officinale* Rosc. + *Terminalia chebula* Retzius | 5.93 ± 0.4 | 4.75 ± 0.25 | 29.12 ± 0.55 |

3-4: Effect of Ameliorating Crohn's Disease in TNBS Animal Model

ICR female mice (17 g to 19 g, 6-week old, DBL Co., Ltd. (Eumseong, Korea), 5-aminosalicylic acid (5-ASA), and 2,4,6-trinitro-benzene sulfonic acid (TNBS) were used.

The effect of mixed extract of *Zingiber officinale* Rosc. and *Terminalia chebula Retzius* of the present invention on the treatment and amelioration of Crohn's disease in an animal model of TNBS Crohn's disease was confirmed.

Figure 22:
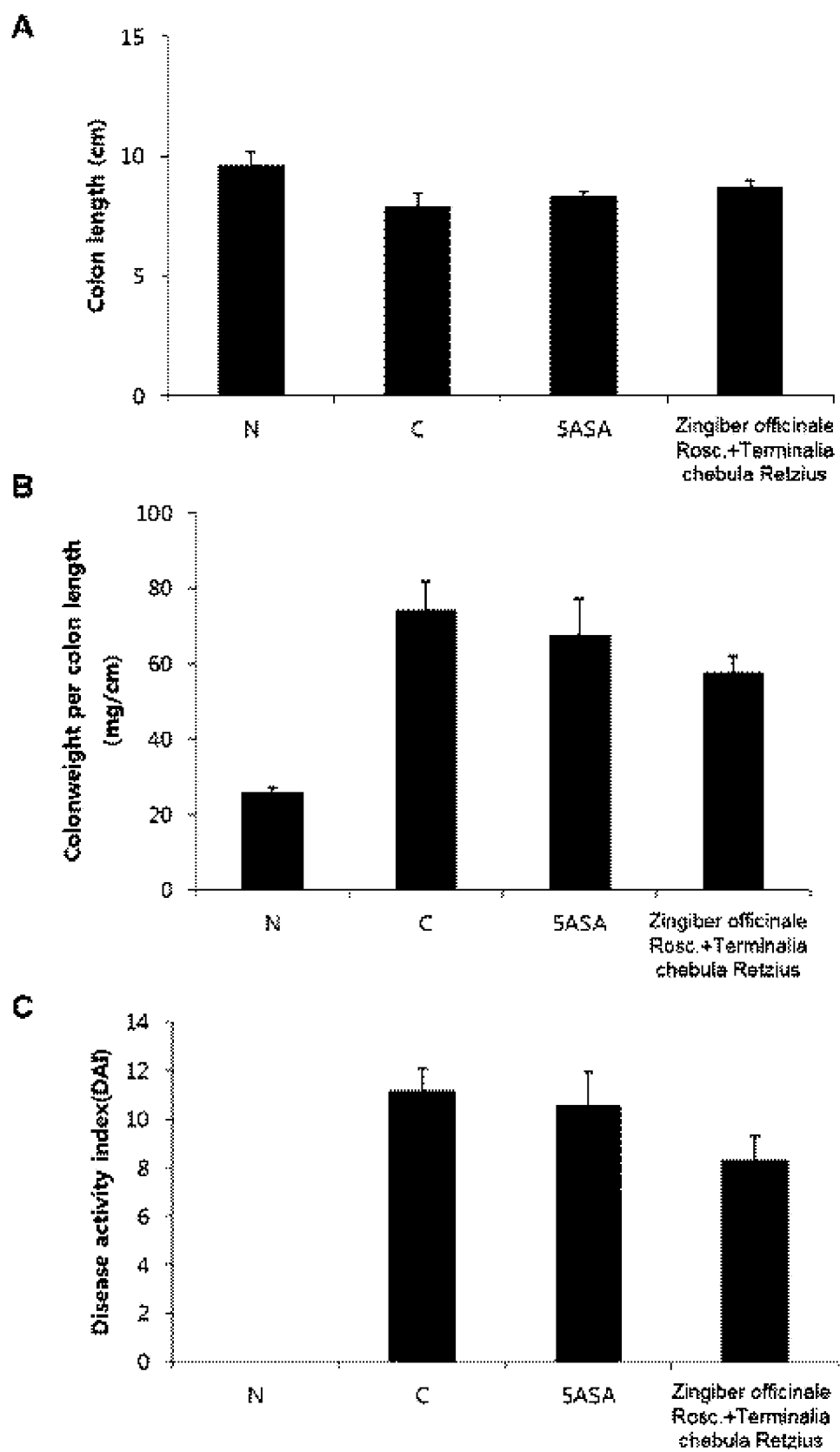
FIG. 22 shows graphs illustrating the effects of a mixed extract containing *Zingiber officinale* Rosc. and *Terminalia chebula* Retzius in an animal model of TNBS-induced Crohn's disease.

As a result of examining the colon length, it was confirmed that the colon length was increased in the group treated with the mixed extract of the present invention compared to the Crohn's disease-induced group (Table 13, FIG. 22 A).

Additionally, as a result of examining the colon weight per colon length, it was confirmed that the colon length in the Crohn's disease-induced group was about 74 mg/cm thus showing an increase of about 49 mg/cm compared to the normal group. The control-drug treated group showed a difference of about 6.5 mg/cm compared to that of the Crohn's disease-induced group, and this suggests that the control drug is slightly effective in reducing the thickened intestinal wall.

In contrast, the group treated with a mixed extract of *Zingiber officinale* Rosc. and *Terminalia chebula* Retzius of the present invention showed a decrease of about 23% compared to the Crohn's disease-induced group, and this confirmed that the mixed extracts of the present invention is effective in improving the thickened intestinal wall due to Crohn's disease (Table 13, FIG. 22 B).

Additionally, as a result of expressing the disease activity index by observing the external appearances, diarrhea and melena were discovered in the Crohn's disease-induced group thus showing a higher score of about 11, whereas the control drug-treated group showed an effect of improvement by an insignificant level of 9% compared to the Crohn's disease-induced group. In contrast, the group treated with the mixed extract of the present invention showed an effect of improvement by about 27% thus showing a significantly higher effect than the control drug-treated group (Table 13, FIG. 22C).

TABLE 13

| Category | Colon Length (cm) | DAI | Weight per Area |
|---|---|---|---|
| Normal Control Group | 9.64 ± 0.54 | 0 | 25.75 ± 1.51 |
| Colitis-induced Group | 7.92 ± 0.56 | 11.20 ± 0.89 | 74.12 ± 7.71 |
| Control drug-treated Group | 8.33 ± 0.22 | 10.56 ± 1.40 | 67.67 ± 9.30 |
| *Zingiber officinale* Rosc. + *Terminalia chebula* Retzius | 8.75 ± 0.25 | 8.33 ± 0.97 | 57.49 ± 4.46 |

Through these results, it was confirmed that the mixed extract of *Zingiber officinale* Rosc. and *Terminalia chebula* Retzius of the present invention shows an excellent anti-inflammatory effect and an effect of ameliorating Crohn's disease, and thus can be effectively used for the prevention or treatment of inflammatory bowel disease.

Example 4: Confirmation of Effect of Mixed Extract of *Aucklandia lappa* Decne, *Terminalia Chebula Retzius*, and *Zingiber officinale* Rosc Furthermore, the present inventors mixed the 3 kinds (i.e., *Aucklandia lappa* Decne, *Terminalia chebula* Retzius, and *Zingiber officinale* Rosc.) according to the blending ratios of Nos. 1 to 5 in Table 14, added 7 volumes of 50% aqueous ethanol solution relative to the sample weight, and performed reflux extraction at 80° C. for 3 hours, and filtered and freeze-dried the thus-obtained extract, and stored in the refrigerator in a power form and used as a sample for the experiment.

TABLE 14

| No. | Aucklandia lappa Decne:Terminalia chebula Retzius:Zingiber officinale Rosc. | Amount of 50% Aqueous Ethanol |
|---|---|---|
| 1 | 100 g:100 g:100 g | 2,100 mL |
| 2 | 200 g:200 g:100 g | 3,500 mL |
| 3 | 200 g:100 g:100 g | 2,800 mL |
| 4 | 100 g:200 g:100 g | 2,800 mL |
| 5 | 100 g:100 g:200 g | 2,800 mL |

4-1: Inhibitory Effect on Monocyte Adhesion in Intestinal Epithelial Cells

The fluorescent-labeled U937 cell adhesion to the HT-29 intestinal epithelial cells was significantly increased by TNF-α stimulus, and the adhesion was inhibited by about 25% by the control drug (5-ASA).

Figure 23:
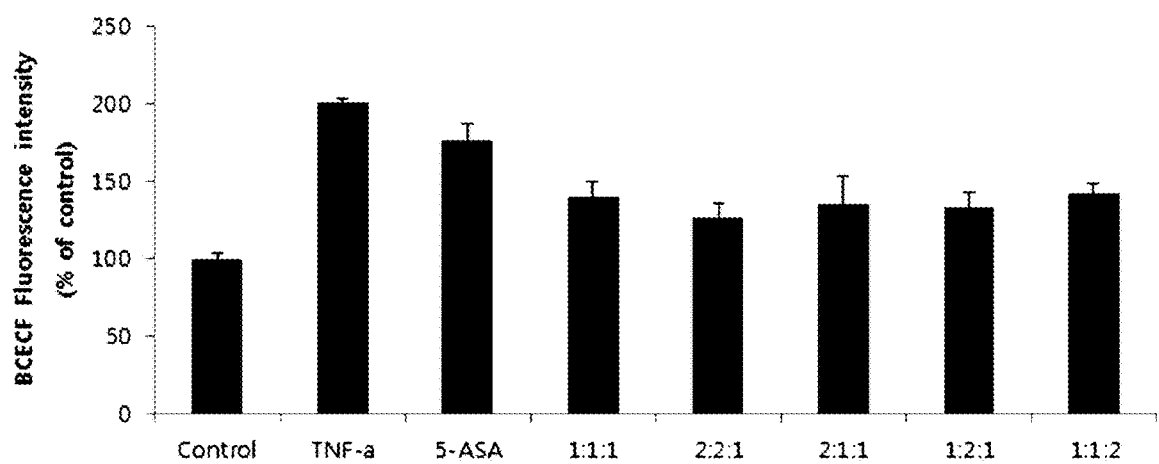
FIG. 23 shows a graph illustrating the inhibitory effect of a mixed extract containing *Aucklandia lappa* Decne, *Terminalia chebula* Retzius, and *Zingiber officinale* Rosc. on monocyte adhesion in intestinal epithelial cells.

In the case of a mixed sample of Aucklandia lappa Decne, Terminalia chebula Retzius, and Zingiber officinale Rosc. of Nos. 1 to 5, it showed an excellent inhibitory effect of about 60% to 70% compared to the control group, and in particular, in the case of the mixed sample, in which Aucklandia lappa Decne:Terminalia chebula Retzius:Zingiber officinale Rosc. was mixed in a ratio of 2:2:1, the extract was shown to have the most excellent effect of inhibiting the adhesion activity (Table 15, FIG. 23).

TABLE 15

| Category | Concentration | Effect of Inhibiting Adhesion (%) |
|---|---|---|
| control | — | — |
| TNF-α (negative control group) | 100 ng/ml | — |
| 5ASA (positive control group) | 20 mM | 24.48 |
| Aucklandia lappa Decne:Terminalia chebula Retzius:Zingiber officinale Rosc. = 1:1:1 | 100 μg/mL | 59.66 |
| Aucklandia lappa Decne:Terminalia chebula Retzius:Zingiber officinale Rosc. = 2:2:1 | 100 μg/mL | 73.27 |
| Aucklandia lappa Decne:Terminalia chebula Retzius:Zingiber officinale Rosc. = 2:1:1 | 100 μg/mL | 64.97 |
| Aucklandia lappa Decne:Terminalia chebula Retzius:Zingiber officinale Rosc. = 1:2:1 | 100 μg/mL | 66.82 |
| Aucklandia lappa Decne:Terminalia chebula Retzius:Zingiber officinale Rosc. = 1:1:2 | 100 μg/mL | 58.13 |

4-2: Effect of Inhibiting IL-6 Production (Inflammatory Cytokine)

Figure 24:
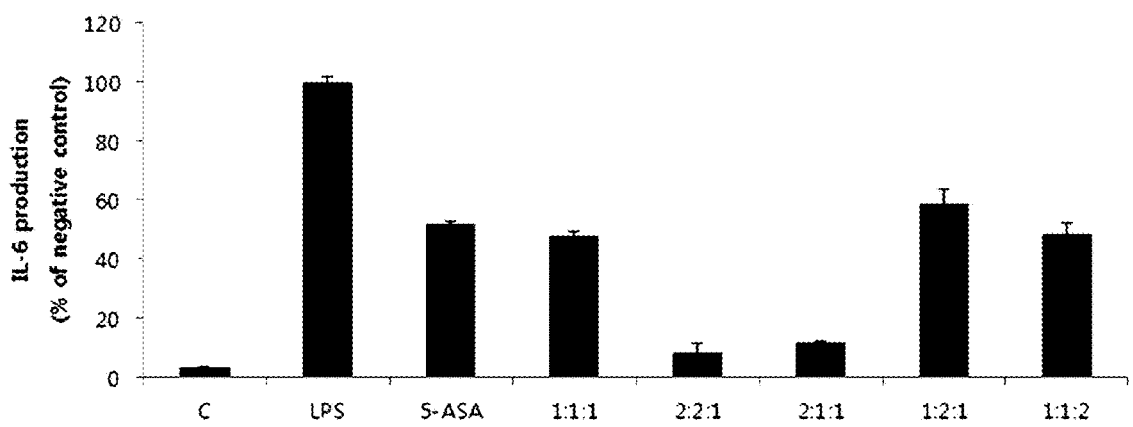
FIG. 24 shows a graph illustrating the inhibitory effect of a mixed extract containing *Aucklandia lappa* Decne, *Terminalia chebula* Retzius, and *Zingiber officinale* Rosc. on LPS-induced production of IL-6 (i.e., an inflammatory cytokine).

As a result of examining the concentrations of the mixed sample of Aucklandia lappa Decne, Terminalia chebula Retzius, and Zingiber officinale Rosc. of Nos. 1 to 5, it was confirmed that the expression levels of IL-6 were significantly reduced, and in particular, when the mixing ratio of the mixed sample of Aucklandia lappa Decne:Terminalia chebula Retzius:Zingiber officinale Rosc. was 2:2:1 or 2:1:1, the effect of inhibiting IL-6 was most excellent (Table 16, FIG. 24).

TABLE 16

| Category | Concentration | Effect of Inhibiting IL-6 Production (%) |
|---|---|---|
| 5ASA | 20 mM | 49.89 |
| Aucklandia lappa Decne:Terminalia chebula Retzius:Zingiber officinale Rosc. = 1:1:1 | 50 μg/mL | 54.30 |
| Aucklandia lappa Decne:Terminalia chebula Retzius:Zingiber officinale Rosc. = 2:2:1 | 50 μg/mL | 94.92 |
| Aucklandia lappa Decne:Terminalia chebula Retzius:Zingiber officinale Rosc. = 2:1:1 | 50 μg/mL | 91.15 |
| Aucklandia lappa Decne:Terminalia chebula Retzius:Zingiber officinale Rosc. = 1:2:1 | 50 μg/mL | 42.94 |
| Aucklandia lappa Decne:Terminalia chebula Retzius:Zingiber officinale Rosc. = 1:1:2 | 50 μg/mL | 53.56 |

4-3: Effect of Ameliorating Colitis in DSS Animal Model

An attempt was made to confirm the effect of mixed extract of Aucklandia lappa Decne, Terminalia chebula Retzius, and Zingiber officinale Rosc. of the present invention on the treatment and amelioration of colitis in an animal model of DSS inflammatory bowel disease.

Figure 25:
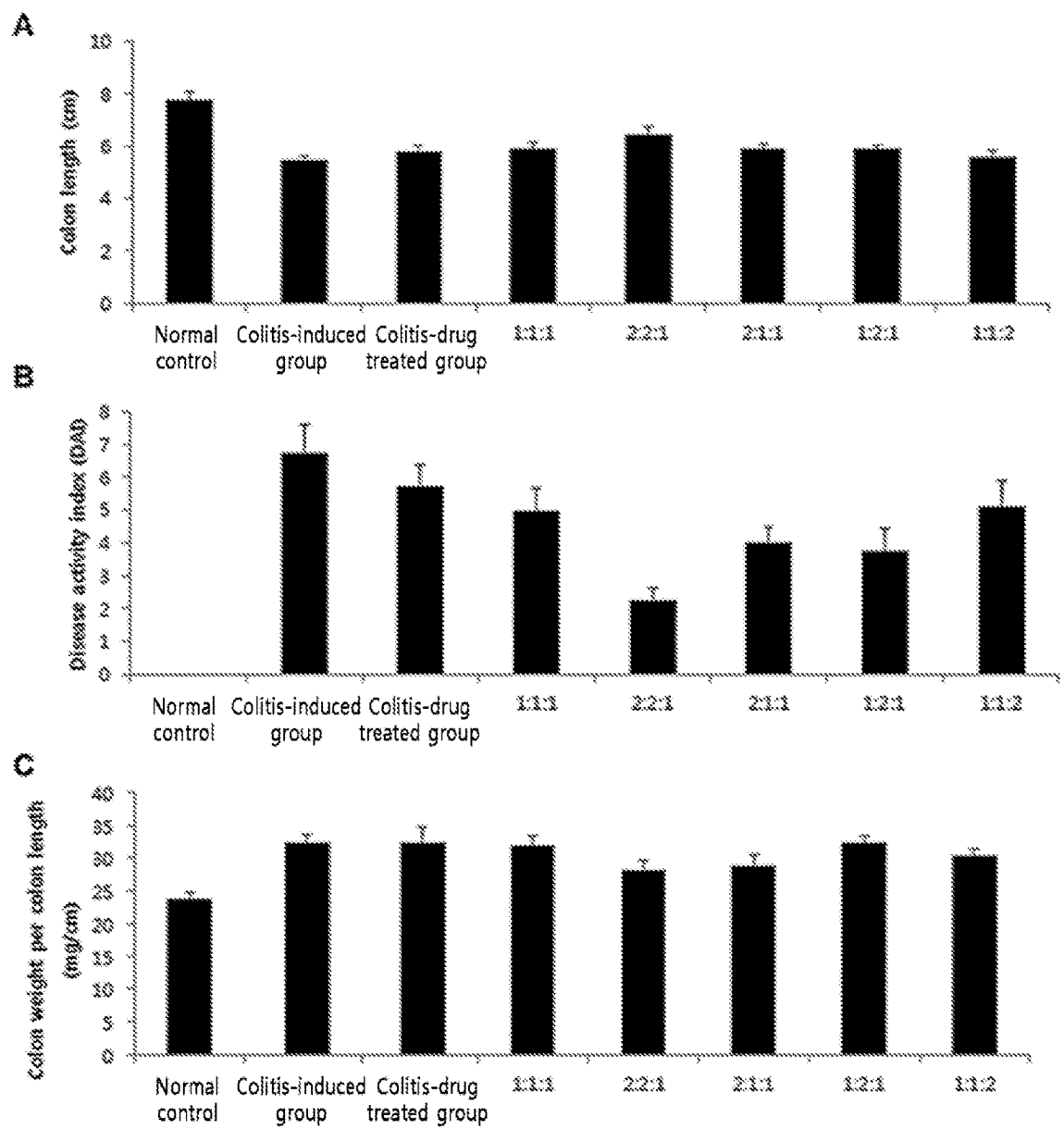
FIG. 25 shows graphs illustrating the effects of a mixed extract containing *Aucklandia lappa* Decne, *Terminalia chebula* Retzius, and *Zingiber officinale* Rosc. according to their mixing ratio in an animal model of DSS-induced colitis.

As a result of examining the colon length, it was confirmed that the colon length in the group treated with the mixed extracts of the present invention was increased compared to that in the colitis-induced group. In particular, when the mixing ratio of Aucklandia lappa Decne:Terminalia chebula Retzius:Zingiber officinale Rosc. was 2:2:1, the colon length was shown to be longest (Table 17, FIG. 25 A).

Additionally, as a result of expressing the disease activity index by observing the external appearances, diarrhea and melena were discovered in the colitis-induced group thus showing a higher score of 6.75, whereas the group treated with the mixed extract of the present invention showed an effect of improvement by having all of DAI of 5.13 or below. In particular, when the mixing ratio of Aucklandia lappa Decne:Terminalia chebula Retzius:Zingiber officinale Rosc. was 2:2:1, the DAI was 2.25 thereby showing the most distinguished effect of improvement (Table 17, FIG. 25 B).

Additionally, as a result of examining the colon weight per colon length, it was confirmed that the colon weight per colon length in the colitis-induced group was about 32 mg/cm thus showing an increase of about 9 mg/cm compared to the normal group. The group treated with a mixed extract of the present invention showed a slight decrease compared to that of the colitis-induced group, and this suggests that the mixed extract of the present invention is effective in reducing the thickened intestinal wall. In particular, when the mixing ratio of Aucklandia lappa Decne:Terminalia chebula Retzius:Zingiber officinale Rosc. was 2:2:1, the effect of reducing the intestinal wall was shown to be most significant (Table 17, FIG. 25 C).

TABLE 17

| Category | Colon Length | DAI | Weight per Area |
|---|---|---|---|
| Normal Control Group | 7.8 | 0 | 23.87 |
| Colitis-induced Group | 5.44 | 6.75 | 32.36 |
| Control drug-treated Group | 5.77 | 5.75 | 32.52 |
| Aucklandia lappa Decne:Terminalia chebula Retzius:Zingiber | 5.91 | 5.00 | 32.07 |

TABLE 17-continued

| Category | Colon Length | DAI | Weight per Area |
|---|---|---|---|
| officinale Rosc. = 1:1:1 | | | |
| Aucklandia lappa Decne:Terminalia chebula Retzius:Zingiber officinale Rosc. = 2:2:1 | 6.48 | 2.25 | 28.27 |
| Aucklandia lappa Decne:Terminalia chebula Retzius:Zingiber officinale Rosc. = 2:1:1 | 5.88 | 4.00 | 28.91 |
| Aucklandia lappa Decne:Terminalia chebula Retzius:Zingiber officinale Rosc. = 1:2:1 | 5.88 | 3.75 | 32.41 |
| Aucklandia lappa Decne:Terminalia chebula Retzius:Zingiber officinale Rosc. = 1:1:2 | 5.55 | 5.13 | 30.35 |

4-4: Effect of Ameliorating Crohn's Disease in TNBS Animal Model

Similarly to the colitis model above, the effect of mixed extract of *Aucklandia lappa* Decne, *Terminalia chebula* Retzius, and *Zingiber officinale* Rosc. of the present invention on the treatment and amelioration of Crohn's disease was confirmed in an animal model with TNBS Crohn's disease.

From the results of examining the colon length, it was confirmed that the group treated with the mixed extract of the present invention showed an increase in the colon length compared to that of the Crohn's disease-induced group. In particular, when the mixing ratio of *Aucklandia lappa* Decne:*Terminalia chebula* Retzius:*Zingiber officinale* Rosc. was 2:2:1, the colon length was shown to be longest (Table 18, FIG. 26 A).

Figure 26:
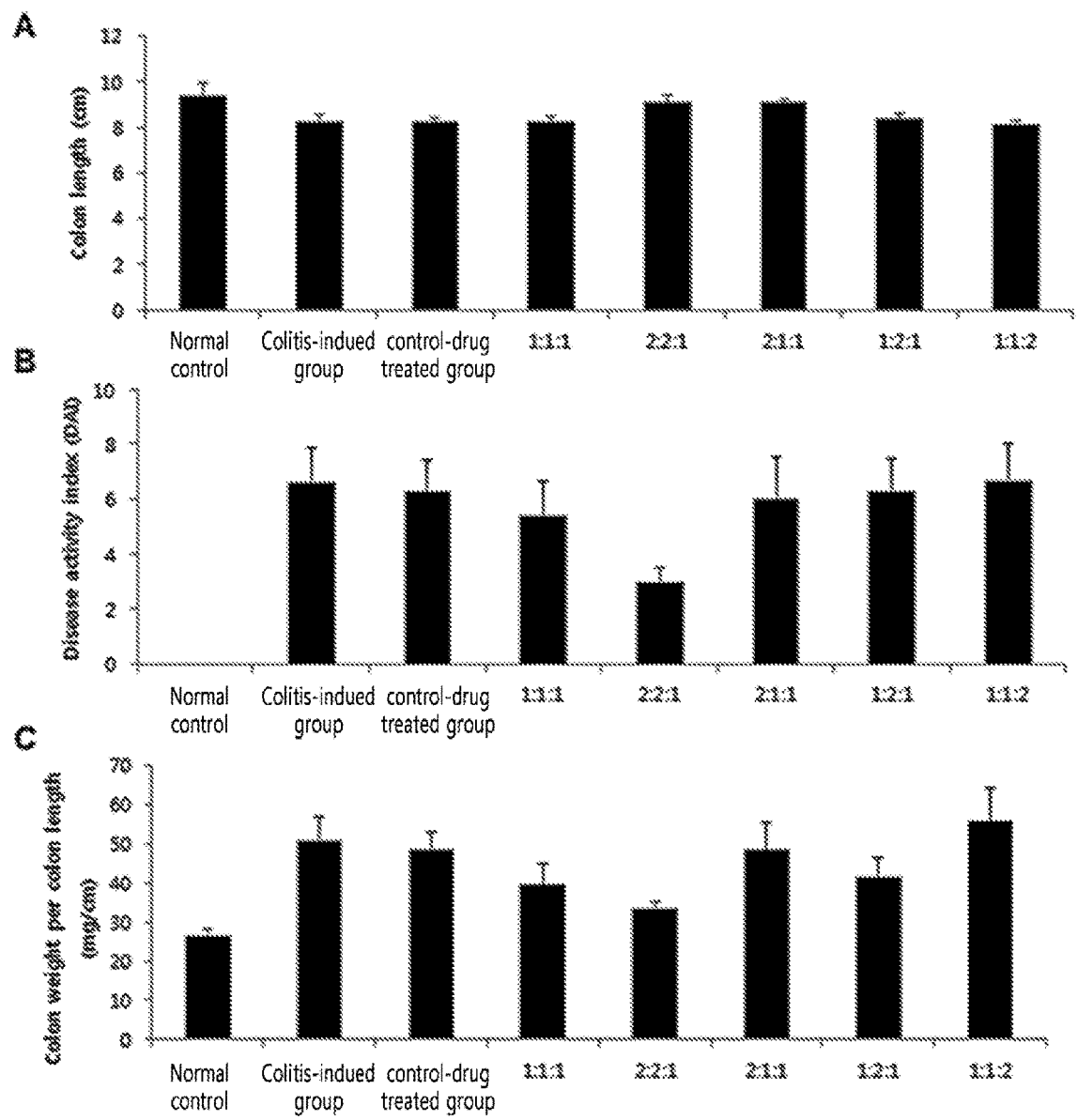
FIG. 26 shows graphs illustrating the effects of a mixed extract containing *Aucklandia lappa* Decne, *Terminalia chebula* Retzius, and *Zingiber officinale* Rosc. according to their mixing ratio in an animal model of TNBS-induced Crohn's disease.

Additionally, when examining the disease activity index by observing the external appearances, the group treated with the mixed extract of the present invention, all of them showed an effect of improvement, and in particular, when the mixing ratio of *Aucklandia lappa* Decne:*Terminalia chebula* Retzius:*Zingiber officinale* Rosc. was 2:2:1, it resulted in having a significant effect of improvement by having DAI 3 (Table 18, FIG. 26 B).

Additionally, as a result of examining the colon weight per colon length, it was confirmed that the group treated with the mixed extract of the present invention was effective in improving the thickened intestinal wall, and in particular, when the mixing ratio of *Aucklandia lappa* Decne:*Terminalia chebula* Retzius:*Zingiber officinale* Rosc. was 2:2:1, it resulted in the most significant effect of reducing the thickness (Table 18, FIG. 26 C).

TABLE 18

| Category | Colon Length | DAI | Weight per Area |
|---|---|---|---|
| Normal Control Group | 9.38 | 0 | 26.48 |
| Crohn's disease-induced group | 8.28 | 6.60 | 50.70 |
| control-drug treated group | 8.27 | 6.30 | 48.66 |
| Aucklandia lappa Decne:Terminalia chebula Retzius:Zingiber officinale Rosc. = 1:1:1 | 8.26 | 5.43 | 39.66 |
| Aucklandia lappa Decne:Terminalia chebula Retzius:Zingiber officinale Rosc. = 2:2:1 | 9.13 | 3.00 | 33.32 |
| Aucklandia lappa Decne:Terminalia chebula Retzius:Zingiber officinale Rosc. = 2:1:1 | 9.11 | 6.00 | 48.56 |
| Aucklandia lappa Decne:Terminalia chebula Retzius:Zingiber officinale Rosc. = 1:2:1 | 8.40 | 6.29 | 41.51 |

TABLE 18-continued

| Category | Colon Length | DAI | Weight per Area |
|---|---|---|---|
| Aucklandia lappa Decne:Terminalia chebula Retzius:Zingiber officinale Rosc. = 1:1:2 | 8.13 | 6.67 | 55.64 |

From these results, it was confirmed that since the mixed extract of *Aucklandia lappa* Decne, *Terminalia chebula* Retzius, and *Zingiber officinale* Rosc. has an excellent anti-inflammatory effect, an effect of ameliorating colitis, and an effect of ameliorating Crohn's disease, and thus can be effective used for the prevention or treatment of inflammatory bowel disease.

Example 5: Confirmation of Effect of Mixed Extract of *Aucklandia lappa* Decne, *Terminalia Chebula Retzius*, and *Zingiber officinale* Rosc. According to Extraction Solvent Furthermore, the present inventors mixed the 3 kinds (i.e., *Aucklandia lappa* Decne, *Terminalia chebula* Retzius, and *Zingiber officinale* Rosc.) in a mixing ratio of *Aucklandia lappa* Decne:*Terminalia chebula* Retzius:*Zingiber officinale* Rosc.=200 g:200 g:100 g, added 7 volumes of extraction solvents of Nos. 1 to 3 in Table 19 relative to the weight of the sample, and performed reflux extraction at 80° C. for 3 hours, respectively, and filtered and freeze-dried the thus-obtained extract, and stored in the refrigerator in a powder form and used as a sample for the experiment.

TABLE 19

| No. | Extraction Solvent | Amount of Extraction Solvent |
|---|---|---|
| 1 | 30% Ethanol | 3,500 mL |
| 2 | 50% Ethanol | 3,500 mL |
| 3 | 70% Ethanol | 3,500 mL |

5-1: Inhibitory Effect on Monocyte Adhesion in Intestinal Epithelial Cells

The fluorescent-labeled U937 cell adhesion to the HT-29 intestinal epithelial cells was significantly increased by TNF-α stimulus, and the adhesion was inhibited by 25% by the control drug (5-ASA).

Figure 27:
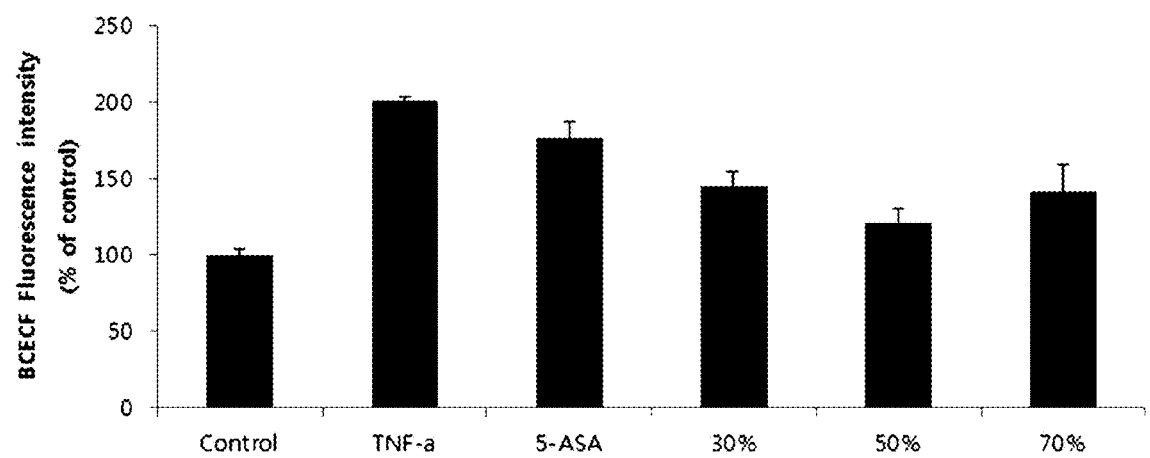
FIG. 27 shows a graph illustrating the inhibitory effect of a mixed extract containing *Aucklandia lappa* Decne, *Terminalia chebula* Retzius, and *Zingiber officinale* Rosc. on monocyte adhesion in intestinal epithelial cells according to extraction solvents.

In the case of mixed samples extracted with 30% ethanol, 50% ethanol, and 70% ethanol, all of them showed excellent inhibitory effects of about 60% to about 80% compared to the control group, and in particular, the extraction with 50% ethanol showed the most excellent inhibitory effect against adhesion (Table 20, FIG. 27).

TABLE 20

| Category | Concentration | Effect of Inhibiting Adhesion (%) |
|---|---|---|
| 5ASA (positive control group) | 20 mM | 24.48 |
| 30% Ethanol | 100 μg/mL | 55.22 |
| 50% Ethanol | 100 μg/mL | 79.24 |
| 70% Ethanol | 100 μg/mL | 59.19 |

5-2: Effect of Inhibiting Production of IL-6 (Inflammatory Cytokine)

Figure 28:
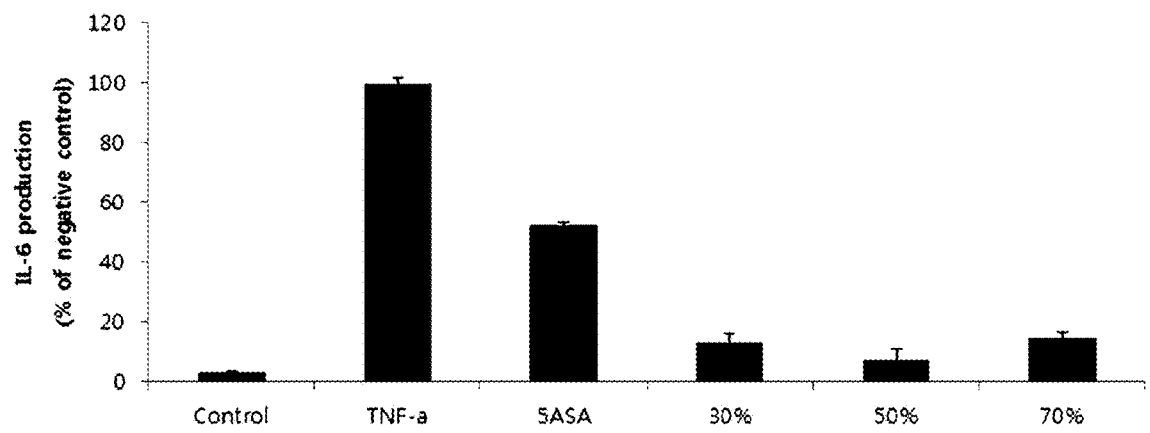
FIG. 28 shows a graph illustrating the inhibitory effect of a mixed extract containing *Aucklandia lappa* Decne, *Terminalia chebula* Retzius, and *Zingiber officinale* Rosc. on the production of IL-6 (i.e., an inflammatory cytokine) according to extraction solvents.

In the cases of mixed samples of *Aucklandia lappa* Decne, *Terminalia chebula* Retzius, and *Zingiber officinale* Rosc. Extracted with 30% ethanol, 50% ethanol, and 70% ethanol, as a result of examining the concentration of IL-6, the expression levels of IL-6 were significantly reduced, and in particular, the extraction with 50% ethanol as an extraction solvent most effectively inhibited the production of IL-6 (Table 21, FIG. 28).

TABLE 21

| Category | Concentration | Effect of Inhibiting IL-6 Production (%) |
|---|---|---|
| 5ASA | 20 mM | 49.35 |
| 30% ethanol | 50 µg/mL | 89.96 |
| 50% ethanol | 50 µg/mL | 95.93 |
| 70% ethanol | 50 µg/mL | 88.65 |

5-3: Effect of Ameliorating Colitis in DSS Animal Model

An attempt was made to confirm the effect of mixed extract of *Aucklandia lappa* Decne, *Terminalia chebula* Retzius, and *Zingiber officinale* Rosc. of the present invention on the treatment and amelioration of colitis in an animal model of DSS inflammatory bowel disease.

Figure 29:
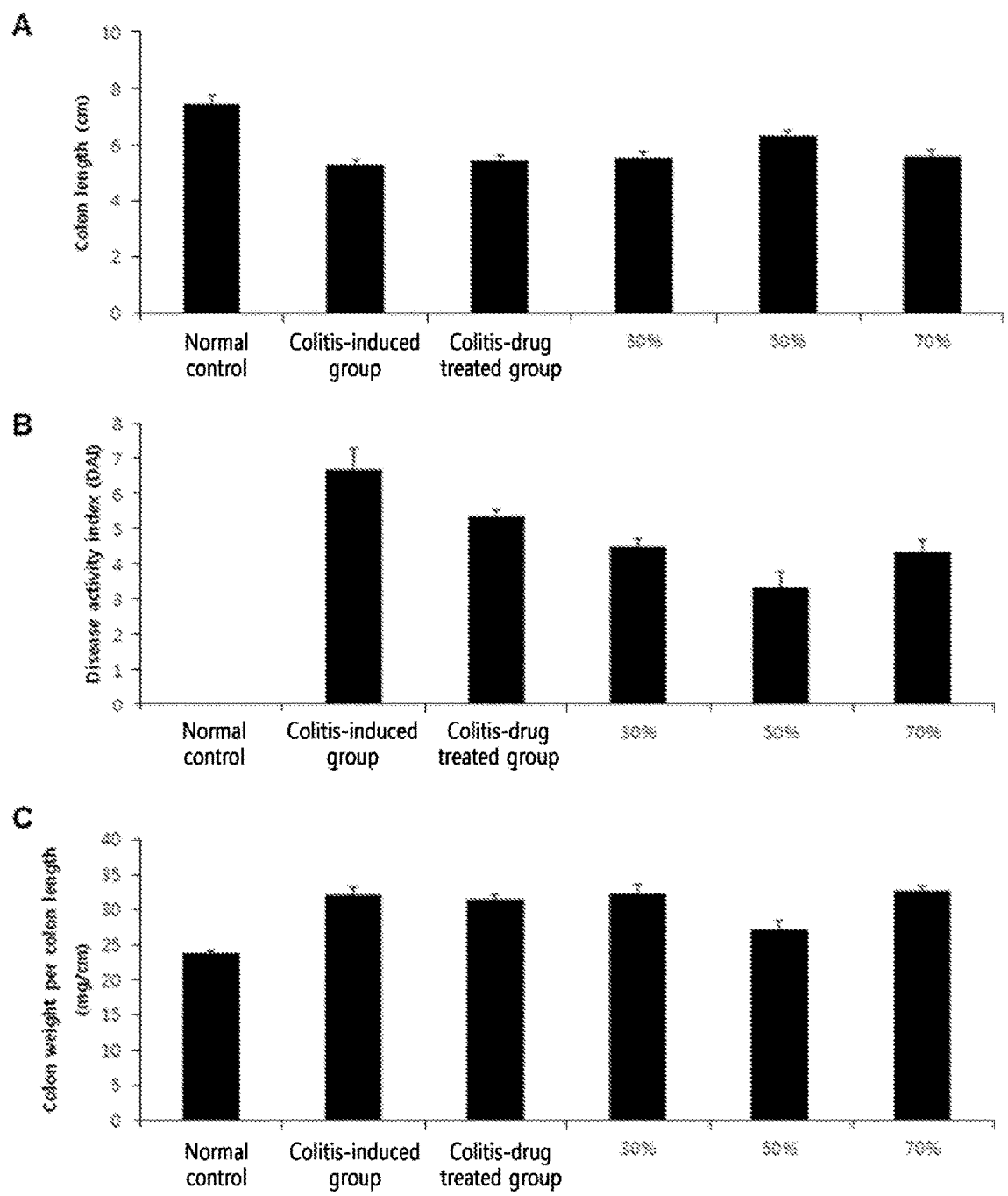
FIG. 29 shows graphs illustrating the effects of a mixed extract containing *Aucklandia lappa* Decne, *Terminalia chebula* Retzius, and *Zingiber officinale* Rosc. according to extraction solvents in an animal model of DSS-induced Crohn's disease.

From the results of examining the colon length, it was confirmed that the group treated with mixed extract of the present invention showed an increase in the colon length compared to that of the colitis-induced group. In particular, when the extraction was performed using 50% ethanol, the colon length was shown to be longest (Table 22, FIG. 29 A).

Additionally, as a result of expressing the disease activity index by observing the external appearances, diarrhea and melena were discovered in the colitis-induced group thus showing a higher score of 6.67, whereas the group treated with the extract obtained using an aqueous ethanol solution as an extraction solvent of the present invention, all showed an improvement by having a DAI of 4.5 or below. In particular, in the case of extracts obtained with 50% ethanol, the effect of improvement was shown to be most significant (Table 22, FIG. 29 B).

Additionally, as a result of examining the colon weight per colon length, it was confirmed that the colitis-induced group had the colon weight per colon length of about 32 mg/cm thus showing an increase of about 9 mg/cm compared to the normal group. In the case of the group treated with the mixed extract of the present invention, it was confirmed that the colon weight was slightly decreased compared to the colitis-induced group (about 27 mg/cm) and thus the mixed extract of the present invention were shown to be effective in improving the thickened intestinal wall (Table 22, FIG. 29 C).

TABLE 22

| Category | Colon Length | DAI | Weight per Area |
|---|---|---|---|
| Normal Control Group | 7.45 | 0 | 23.80 |
| Colitis-induced Group | 5.31 | 6.67 | 32.10 |
| Control drug-treated Group | 5.45 | 5.33 | 31.42 |
| 30% Ethanol | 5.51 | 4.50 | 32.35 |
| 50% Ethanol | 6.30 | 3.33 | 27.15 |
| 70% Ethanol | 5.60 | 4.33 | 32.69 |

5-4: Effect of Ameliorating Crohn's Disease in TNBS Animal Model

Similarly to the colitis model above, the effect of mixed extract of *Aucklandia lappa* Decne, *Terminalia chebula* Retzius, and *Zingiber officinale* Rosc. of the present invention on the treatment and amelioration of Crohn's disease was confirmed in an animal model with TNBS Crohn's disease.

From the results of examining the colon length, it was confirmed that the group treated with the mixed extract of the present invention showed an increase in the colon length compared to that of the Crohn's disease-induced group. In particular, when the extraction was performed using 50% ethanol, the colon length was shown to be longest (Table 23, FIG. 30 A).

Figure 30:
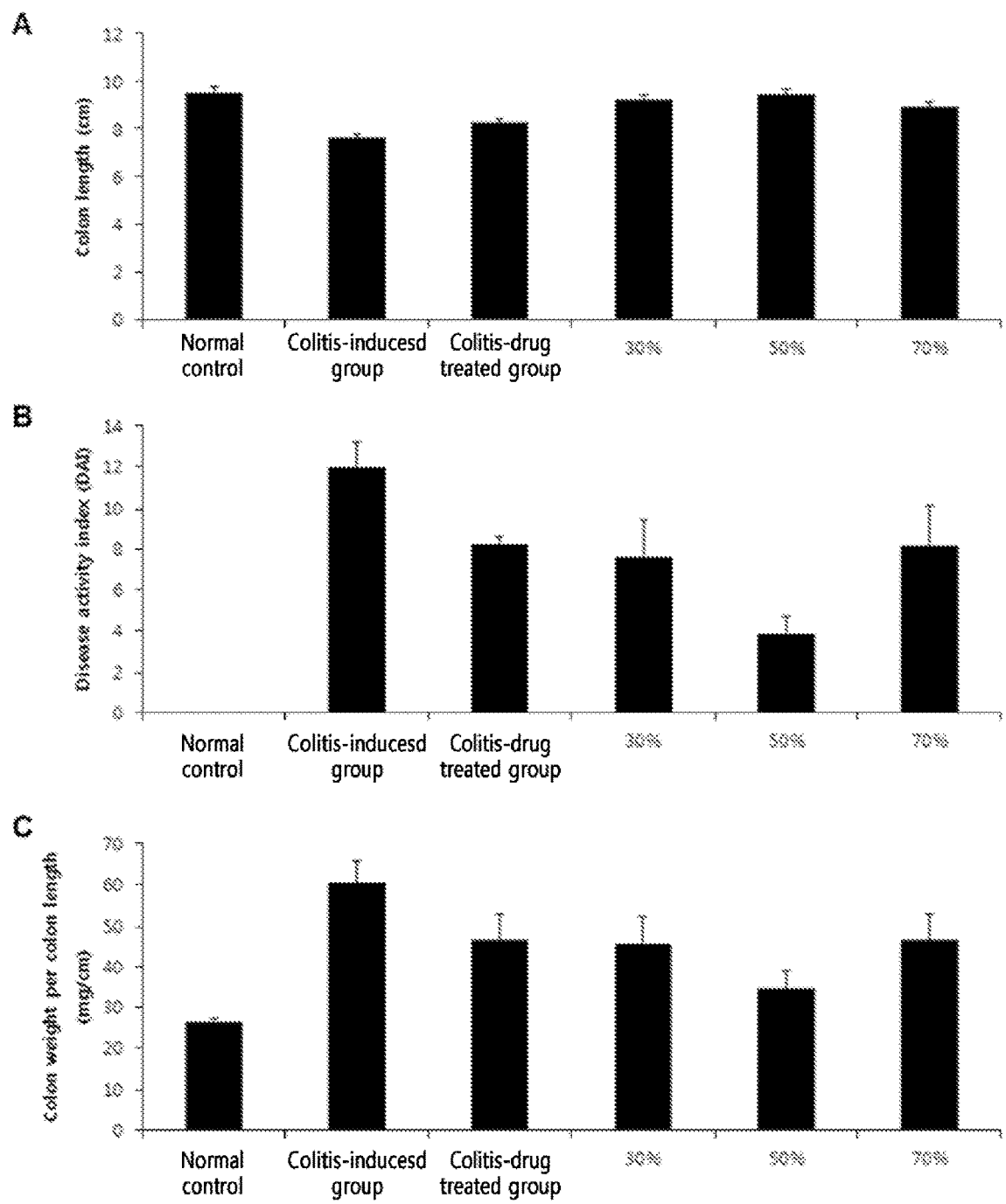
FIG. 30 shows graphs illustrating the effects of a mixed extract containing *Aucklandia lappa* Decne, *Terminalia chebula* Retzius, and *Zingiber officinale* Rosc. according to extraction solvents in an animal model of TNBS-induced Crohn's disease.

Additionally, when examining the disease activity index by observing the external appearances, the group treated with the mixed extract of the present invention, all of them showed an effect of improvement, and in particular, when the extraction was performed using 50% ethanol as a solvent, the improvement was most significant by having a DAI of 3 (Table 23, FIG. 30 B).

Additionally, as a result of examining the colon weight per colon length, it was confirmed that the Crohn's disease-induced group had the colon weight per colon length of about 60 mg/kg thus showing an increase of about 34 mg/kg compared to the normal group, and the group treated with the mixed extract of the present invention showed a significant decrease compared to the Crohn's disease-induced group, and in particular, when the extraction was performed using 50% ethanol as a solvent, the colon weight per colon length was significantly reduced to about 34 mg/kg. From these results, it was confirmed that the mixed extract of the present invention are effective in improving the thickened intestinal wall (Table 23, FIG. 30 C).

TABLE 23

| Category | Colon Length | DAI | Weight per Area |
|---|---|---|---|
| Normal control group | 9.50 | 0 | 26.48 |
| Crohn's disease-induced Group | 7.63 | 12.00 | 60.58 |
| Control drug-treated Group | 8.28 | 8.20 | 46.55 |
| 30% Ethanol | 9.22 | 7.63 | 45.41 |
| 50% Ethanol | 9.44 | 3.88 | 34.68 |
| 70% Ethanol | 8.93 | 8.13 | 46.49 |

Through these results, it was confirmed that the mixed extract containing at least two of *Aucklandia lappa* Decne, *Terminalia chebula* Retzius, and *Zingiber officinale* Rosc. of the present invention has shown excellent anti-inflammatory effect and an effect of improving Crohn's disease, and in particular when the extraction was performed with 50% ethanol, these extracts were shown to have most excellent anti-inflammatory effect, an effect of ameliorating colitis, and an effect of ameliorating Crohn's disease, and thus the mixed extract of the present invention can be effectively used for the prevention or treatment of inflammatory bowel disease.

Example 6: Confirmation of Effect of Mixed Extracts of *Aucklandia lappa* Decne, *Terminalia Chebula Retzius*, and *Zingiber officinale* Rosc. According to Administration Dose Furthermore, the present inventors mixed the 3 kinds (i.e., *Aucklandia lappa* Decne, *Terminalia chebula* Retzius, and *Zingiber officinale* Rosc.) in a mixing ratio of *Aucklandia lappa* Decne:*Terminalia chebula* Retzius:*Zingiber officinale* Rosc.=200 g:200 g:100 g, added 7 volumes of 50% ethanol relative to the weight of the sample, and performed reflux extraction at 80° C. for 3 hours, respectively, and filtered and freeze-dried the thus-obtained extract, and stored in the refrigerator in a powder form and used as a sample for the experiment.

6-1: Effect of Ameliorating Colitis in DSS Animal Model

An attempt was made to confirm the effect of the mixed extract of *Aucklandia lappa* Decne, *Terminalia chebula* Retzius, and *Zingiber officinale* Rosc. of the present invention on the treatment and amelioration of colitis according to a administration dose in an animal model of DSS inflammatory bowel disease.

The mixed extract was administered at a concentration of 50 mg/kg, 100 mg/kg, 200 mg/kg, 400 mg/kg, respectively, and the effect of treatment and amelioration of colit was confirmed.

Figure 31:
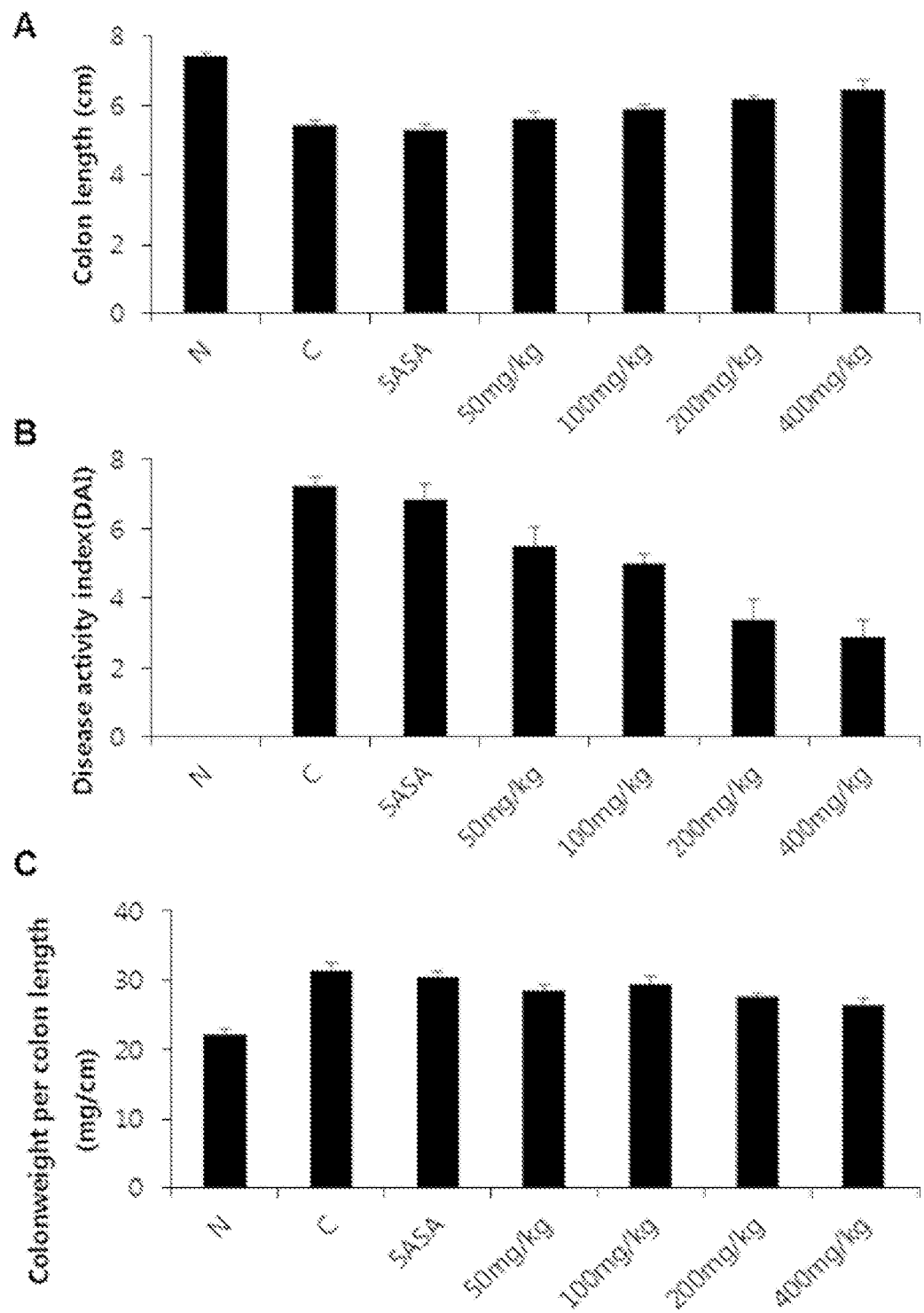
FIG. 31 shows graphs illustrating the effects of a mixed extract containing *Aucklandia lappa* Decne, *Terminalia chebula* Retzius, and *Zingiber officinale* Rosc. according to administration doses in an animal model of DSS-induced colitis.

From the results of examining the colon length, it was confirmed that the group treated with the mixed extract of the present invention showed an increase in the colon length compared to that of the colitis-induced group. In particular, when the mixed extract of the present invention was administered at a dose of 400 mg/kg, the colon length was shown to be longest (Table 24, FIG. 31 A).

Additionally, as a result of expressing the disease activity index by observing the external appearances, diarrhea and melena were discovered in the colitis-induced group thus showing a higher score of 7.25, whereas the group treated with mixed extract of the present invention all showed an improvement by having a DAI of 5.5 or below. In particular, when the mixed extract of the present invention was administered at a dose of 400 mg/kg, the improvement was shown to be most significant by having a DAI of 2.88 (Table 24, FIG. 31 B).

Additionally, as a result of examining the colon weight per colon length, it was confirmed that the colitis-induced group had the colon weight per colon length of about 31 mg/kg thus showing an increase of about 9 mg/kg compared to the normal group, and the group treated with the mixed extract of the present invention showed a slight decrease compared to the colitis-induced group, and in particular, when the mixed extract of the present invention was administered at a dose of 400 mg/kg, the colon weight per colon length was significantly reduced to about 26 mg/kg. From these results, it was confirmed that the mixed extract of the present invention are effective in improving the thickened intestinal wall (Table 24, FIG. 31 C).

TABLE 24

| Category | Colon Length | DAI | Weight per Area |
| --- | --- | --- | --- |
| Normal Control Group | 7.42 ± 0.1 | 0 | 22.25 ± 0.81 |
| Colitis-induced Group | 5.44 ± 0.12 | 7.25 ± 0.25 | 31.51 ± 1.2 |
| Control drug-treated Group | 5.31 ± 0.16 | 6.88 ± 0.44 | 30.66 ± 0.76 |
| 50 mg/kg | 5.63 ± 0.2 | 5.5 ± 0.57 | 28.56 ± 0.88 |
| 100 mg/kg | 5.89 ± 0.15 | 5 ± 0.27 | 29.42 ± 1.25 |
| 200 mg/kg | 6.2 ± 0.08 | 3.38 ± 0.6 | 27.82 ± 0.43 |
| 400 mg/kg | 6.46 ± 0.28 | 2.88 ± 0.48 | 26.52 ± 0.94 |

6-2: Effect of Ameliorating Crohn's Disease in TNBS Animal Model

Similarly to the colitis model above, the effect of mixed extract of *Aucklandia lappa* Decne, *Terminalia chebula* Retzius, and *Zingiber officinale* Rosc. of the present invention on the treatment and amelioration of Crohn's disease according to an administration dose was confirmed in an animal model with TNBS Crohn's disease.

The mixed extract was administered at a concentration of 50 mg/kg, 100 mg/kg, 200 mg/kg, and 400 mg/kg, respectively, and the effect of treatment and amelioration of colitis was confirmed.

From the results of examining the colon length, it was confirmed that the group treated with the mixed extract of the present invention showed an increase in the colon length compared to that of the Crohn's disease-induced group. In particular, when the mixed extract was administered at a concentration of 400 mg/kg, the colon length was shown to be longest (Table 25, FIG. 32 A).

Figure 32:
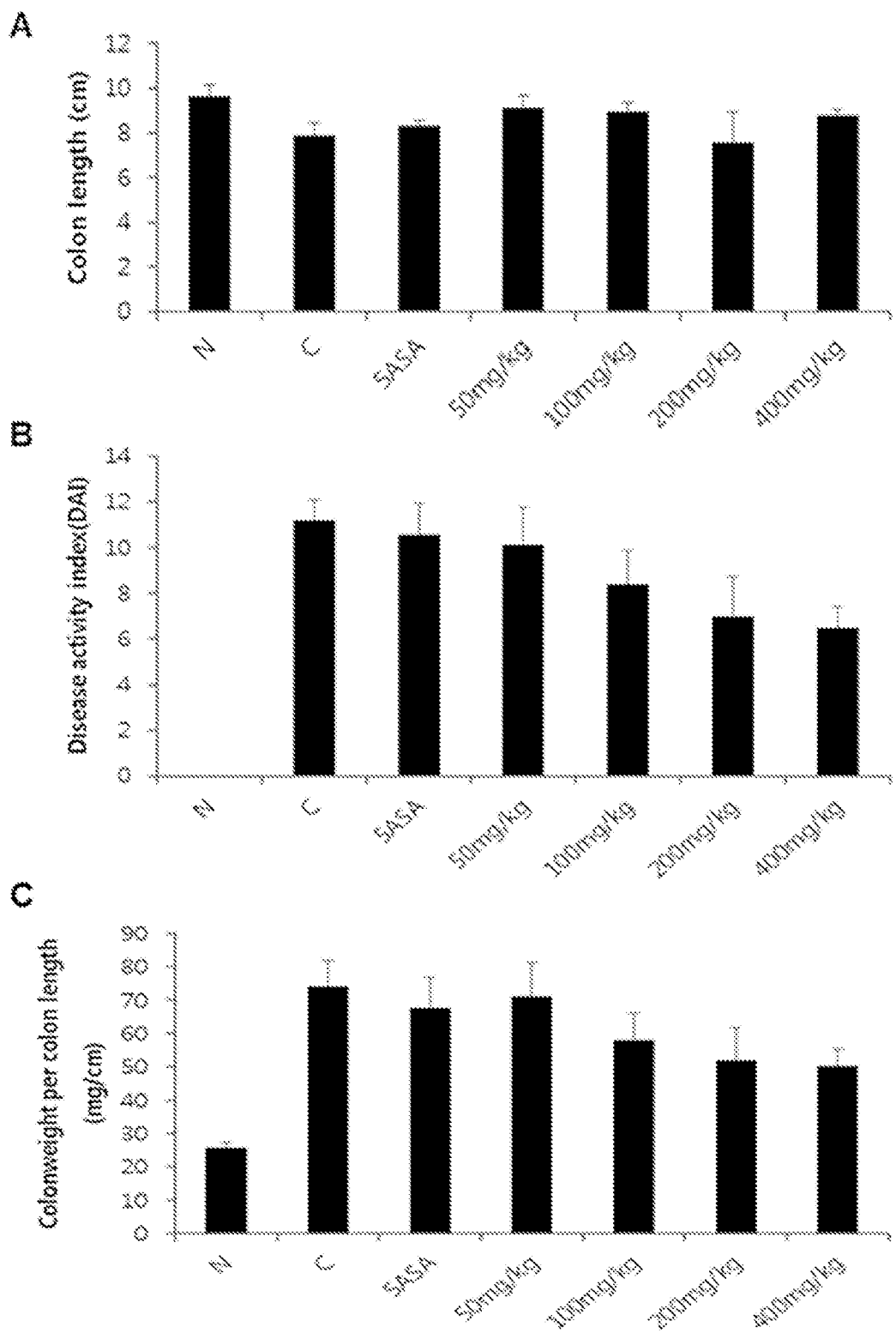
FIG. 32 shows graphs illustrating the effects of a mixed extract containing *Aucklandia lappa* Decne, *Terminalia chebula* Retzius, and *Zingiber officinale* Rosc. according to administration doses in an animal model of TNBS-induced Crohn's disease.

Additionally, when examining the disease activity index by observing the external appearances, the group treated with the mixed extract of the present invention, all of them showed an effect of improvement, and in particular, when the mixed extract was administered at a concentration of 400 mg/kg, the improvement was shown to be most significant by having a DAI of 6.5 (Table 25, FIG. 32 B).

Additionally, as a result of examining the colon weight per colon length, it was confirmed that the Crohn's disease-induced group had the colon weight per colon length of about 74 mg/cm thus showing an increase of about 49 mg/cm compared to the normal group, and the group treated with the mixed extract of the present invention showed a decrease compared to the Crohn's disease-induced group. In particular, when the mixed extract of the present invention was administered at a dose of 400 mg/kg, the colon weight per colon length was significantly reduced to 50 mg/cm, thus confirming that the mixed extracts of the present invention are effective in improving the thickened intestinal wall (Table 25, FIG. 32 C).

TABLE 25

| Category | Colon Length | DAI | Weight per Area |
| --- | --- | --- | --- |
| Normal Control Group | 9.64 ± 0.54 | 0 | 25.75 ± 1.51 |
| Crohn's disease-induced Group | 7.92 ± 0.56 | 11.20 ± 0.89 | 74.12 ± 7.71 |
| Control drug-treated Group | 8.33 ± 0.22 | 10.56 ± 1.40 | 67.67 ± 9.30 |
| 50 mg/kg | 8.76 ± 0.42 | 10.1 ± 1.69 | 71.05 ± 10.20 |
| 100 mg/kg | 8.97 ± 0.37 | 8.38 ± 1.48 | 58.08 ± 8.04 |
| 200 mg/kg | 9.1 ± 0.26 | 7 ± 1.73 | 52.06 ± 9.66 |
| 400 mg/kg | 9.34 ± 0.15 | 6.5 ± 0.9 | 50.24 ± 4.95 |

Through these results, it was confirmed that the mixed extract containing at least two of *Aucklandia lappa* Decne, *Terminalia chebula* Retzius, and *Zingiber officinale* Rosc. of the present invention has shown excellent anti-inflammatory effect and an effect of improving colitis and Crohn's disease at most of the administration doses, and in particular when the mixed extract was administered at a dose of 400 mg/kg, this extract was shown to have most excellent anti-inflammatory effect, an effect of ameliorating colitis, and an effect of ameliorating Crohn's disease, and thus the mixed extract of the present invention can be effectively used for the prevention or treatment of inflammatory bowel disease.

INDUSTRIAL APPLICABILITY

The composition containing a mixed extract of *Aucklandia lappa* Decne, *Terminalia chebula* Retzius, and *Zingiber officinale* Rosc. according to the present invention has an excellent anti-inflammatory effect and an effect of ameliorating colitis, but has almost no cytotoxicity, and thus exhibits effects of preventing and treating inflammatory diseases, in particular inflammatory bowel disease, and is thus expected to be used as an active ingredient of compositions for pharmaceutical drugs, processed foods, functional foods, food additives, functional beverages, or beverage additives, etc. for the prevention and treatment of inflammatory bowel disease.

The invention claimed is:

1. A pharmaceutical composition for preventing or treating Inflammatory bowel disease (IBD) comprising a plant extract, wherein said plant extract consists of *Aucklandia lappa* Decne extract, *Terminalia chebula* Retzius extract, and *Zingiber officinale* Roscoe extract, wherein a weight ratio of *Aucklandia lappa* Decne, *Terminalia chebula* Retzius and *Zingiber officinale* Roscoe is 2:2:1 or 2:1:1.

2. The pharmaceutical composition according to claim 1, wherein said plant extract is a 50% ethanol extract.

3. The pharmaceutical composition according to claim 1, wherein a content of said plant extract contained in the composition is 100~400 mg/kg.

4. The pharmaceutical composition according to claim 1, wherein the composition is an oral composition.

5. The pharmaceutical composition according to claim 1, wherein said plant extract inhibits any one or more of IL-6 and TNF-α production.

6. The pharmaceutical composition according to claim 1, wherein the Inflammatory bowel disease is one or more selected from the group of consisting Crohn's disease, ulcerative colitis, Intestinal Behcet's disease, intestinal tuberculosis and diarrhea.

7. A health and functional food for ameliorating Inflammatory bowel disease (IBD) comprising a plant extract, wherein said plant extract consisting only of *Aucklandia lappa* Decne extract, *Terminalia chebula* Retzius extract, and *Zingiber officinale* Roscoe extract, wherein the *Aucklandia lappa* Decne extract, *Terminalia chebula* Retzius extract and *Zingiber officinale* Roscoe extract are present in a weight ratio of 2:2:1 or 2:1:1.

8. The health and functional food according to claim 7, wherein the health and functional food is a powder, granule, tablet, capsule, syrup or beverage.

9. The health and functional food according to claim 7, wherein the Inflammatory bowel disease is one or more selected from the group of consisting Crohn's disease, ulcerative colitis, Intestinal Behcet's disease, intestinal tuberculosis and diarrhea.

10. The pharmaceutical composition according to claim 1, wherein said plant extract is a crude extract, a polar solvent soluble extract or non-polar solvent soluble extract of *Aucklandia lappa* Decne, *Terminalia chebula* Retzius and *Zingiber officinale* Roscoe.

11. The pharmaceutical composition according to claim 1, wherein said plant extract is extracted using water, a C1-C4 lower alcohol, or a mixture thereof as a solvent.

12. The pharmaceutical composition according to claim 1, wherein said plant extract is a hot water extract or an ethanol extract.

13. The health and functional food according to claim 7, wherein said plant extract is a hot water extract or an ethanol extract.

* * * * *